United States Patent
Huh et al.

(10) Patent No.: US 10,093,852 B2
(45) Date of Patent: Oct. 9, 2018

(54) ORGANIC LIGHT-EMITTING DEVICE INCLUDING A HETEROARYL COMPOUND

(71) Applicant: LG CHEM, LTD., Seoul (KR)

(72) Inventors: Jungoh Huh, Daejeon (KR); Min Woo Jung, Daejeon (KR); Dong Hoon Lee, Daejeon (KR); Boonjae Jang, Daejeon (KR); Minyoung Kang, Daejeon (KR); Dong Uk Heo, Daejeon (KR); Miyeon Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/559,805

(22) PCT Filed: Mar. 29, 2016

(86) PCT No.: PCT/KR2016/003182
§ 371 (c)(1),
(2) Date: Sep. 19, 2017

(87) PCT Pub. No.: WO2016/171406
PCT Pub. Date: Oct. 27, 2016

(65) Prior Publication Data
US 2018/0066180 A1    Mar. 8, 2018

(30) Foreign Application Priority Data
Apr. 24, 2015    (KR) .................. 10-2015-0057830

(51) Int. Cl.
*C09K 11/06*    (2006.01)
*C07D 251/12*    (2006.01)
*H01L 51/50*    (2006.01)
*H01L 51/52*    (2006.01)

(52) U.S. Cl.
CPC ............ *C09K 11/06* (2013.01); *C07D 251/12* (2013.01); *H01L 51/50* (2013.01); *H01L 51/5056* (2013.01); *H01L 51/5088* (2013.01); *H01L 51/5203* (2013.01); *C09K 2211/1018* (2013.01)

(58) Field of Classification Search
CPC ............ C09K 11/06; C09K 2211/1018; C07D 251/12; H01L 51/5056; H01L 51/5203; H01L 51/5088
See application file for complete search history.

(56) References Cited

U.S. PATENT DOCUMENTS

| | | |
|---|---|---|
| 2012/0280613 A1 | 11/2012 | Kang et al. |
| 2014/0077175 A1 | 3/2014 | Jung et al. |
| 2015/0214491 A1 | 7/2015 | Ikeda et al. |
| 2016/0046563 A1 | 2/2016 | Stoessel et al. |

FOREIGN PATENT DOCUMENTS

| | | |
|---|---|---|
| EP | 2161272 A1 | 3/2010 |
| JP | 2012019174 A | 1/2012 |
| JP | 2013258381 A | 12/2013 |
| JP | 2014075556 A | 4/2014 |
| KR | 20110018195 A | 2/2011 |
| KR | 20120078302 A | 7/2012 |
| KR | 20140037391 A | 3/2014 |
| WO | 2014038677 A | 3/2014 |
| WO | 2014146750 A1 | 9/2014 |

*Primary Examiner* — John P Dulka
(74) *Attorney, Agent, or Firm* — Dentons US LLP

(57) ABSTRACT

The present specification relates to an organic light emitting device.

14 Claims, 1 Drawing Sheet

[Figure 1]
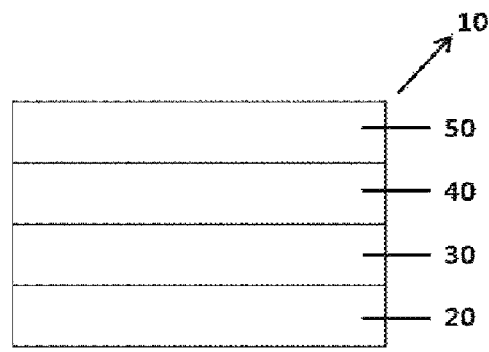
[Figure 2]
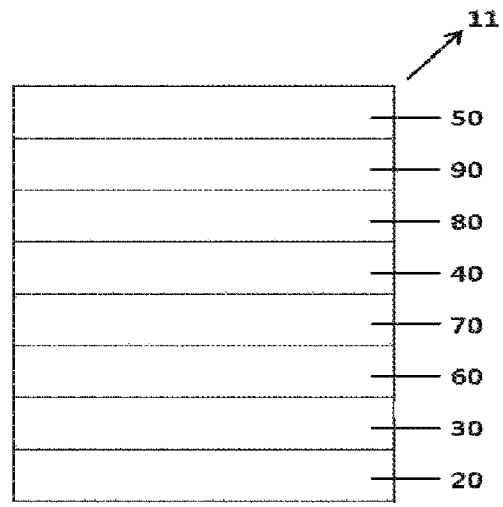

ORGANIC LIGHT-EMITTING DEVICE INCLUDING A HETEROARYL COMPOUND

TECHNICAL FIELD

This application is a National Stage Application of International Application No. PCT/KR2016/003182, filed Mar. 29, 2016, and claims the benefit of Korean Patent Application No. 10-2015-0057830, filed Apr. 24, 2015, contents of which are incorporated herein by reference in their entirety for all purposes as if fully set forth below.

The present specification relates to an organic light emitting device.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. WO2003-012890

DISCLOSURE

Technical Problem

The present specification provides an organic light emitting device.

Technical Solution

An exemplary embodiment of the present specification provides an organic light emitting device including: a first electrode; a second electrode provided to face the first electrode; and one or more organic material layers provided between the first electrode and the second electrode, in which one or more layers of the organic material layers include a compound represented by the following Chemical Formula 1.

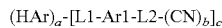  [Chemical Formula 1]

In Chemical Formula 1,
a to c are each an integer of 1 to 3,
when a to c are each 2 or more, two or more structures in the parenthesis are the same as or different from each other,
L1 and L2 are the same as or different from each other, and are each independently a substituted or unsubstituted divalent to tetravalent aromatic ring group, Ar1 is a direct bond; or a substituted or unsubstituted arylene group, and
HAr is a substituted or unsubstituted heteroaryl group.

Advantageous Effects

An organic light emitting device including the compound according to the present specification as a material for an organic material layer has low driving voltage, high efficiency and/or long service life characteristics.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides an organic light emitting device including: a first electrode; a second electrode provided to face the first electrode; and one or more organic material layers provided between the first electrode and the second electrode, in which one or more layers of the organic material layers include the compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with the another member, but also a case where still another member is present between the two members.

Examples of the substituents in the present specification will be described below, but the substituents are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a binding portion.

In the present specification, the halogen group may be fluorine, chlorine, bromine, or iodine.

In the present specification, the number of carbon atoms of the imide group is not particularly limited, but is preferably 1 to 30. Specifically, the imide group may be a compound having the following structures, but is not limited thereto.

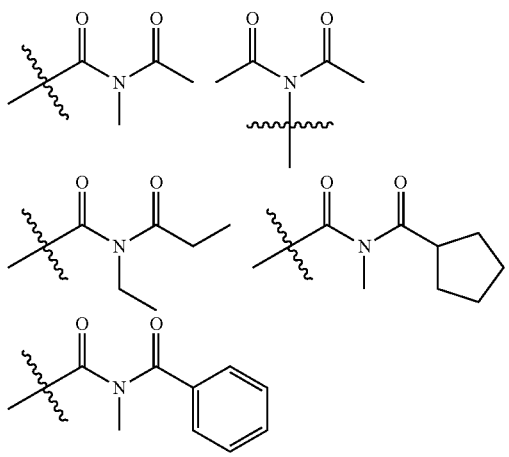

In the present specification, in the amide group, the nitrogen of the amide group may be substituted with hydrogen, a straight-chained, branched, or cyclic alkyl group having 1 to 30 carbon atoms, or an aryl group having 6 to 30 carbon atoms. Specifically, the amide group may be a compound having the following structural formulae, but is not limited thereto.

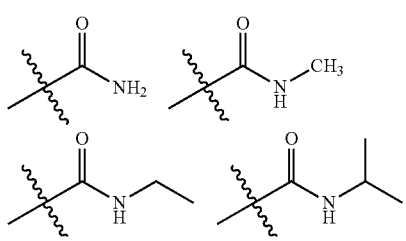

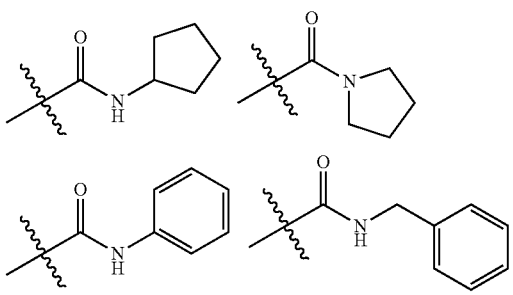

In the present specification, the number of carbon atoms of the carbonyl group is not particularly limited, but is preferably 1 to 30. Specifically, the carbonyl group may be a compound having the following structures, but is not limited thereto.

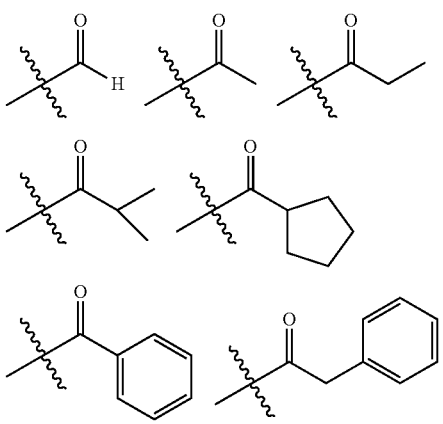

In the present specification, in the ester group, the oxygen of the ester group may be substituted with a straight-chained, branched, or cyclic alkyl group having 1 to 25 carbon atoms, or an aryl group having 6 to 30 carbon atoms. Specifically, the ester group may be a compound having the following structural formulae, but is not limited thereto.

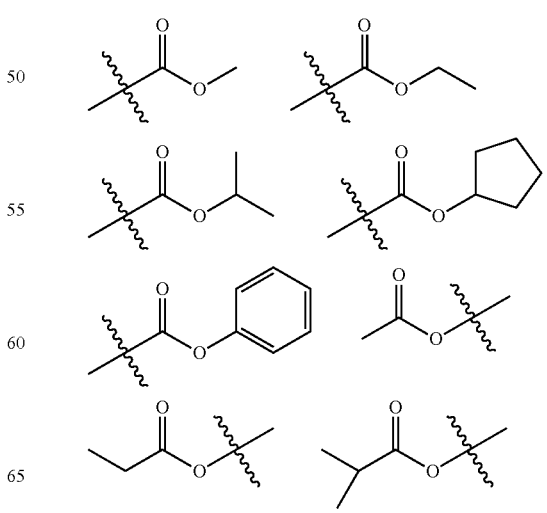

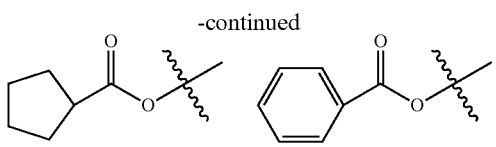

In the present specification, the alkyl group may be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but the number of carbon atoms thereof is preferably 3 to 30, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the amine group may be selected from the group consisting of —NH$_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, the N-alkylarylamine group means an amine group in which an alkyl group and an aryl group are substituted with N of the amine group. In the present specification, the N-arylheteroarylamine group means an amine group in which an aryl group and a heteroaryl group are substituted with N of the amine group. In the present specification, the N-alkylheteroarylamine group means an amine group in which an alkyl group and a heteroarylamine group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples thereof are not limited thereto.

In the present specification, the alkenyl group may be straight-chained or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be —BR100R101, and R100 and R101 are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group include a diphenylphosphine oxide group, a dinaphthylphosphine oxide group, and the like, but are not limited thereto.

In the present specification, the aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

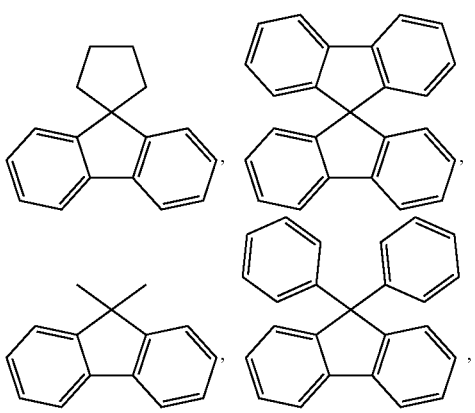

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples thereof are not limited thereto. In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. Two or more arylamine groups which the aryl group includes may include a monocyclic aryl group, a polycyclic aryl group, or both a monocyclic aryl group and a polycyclic aryl group. For example, the aryl group in the arylamine group may be selected from the above-described examples of the aryl group.

In the present specification, the heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 60, and the heteroaryl group may be monocyclic or polycyclic.

Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, an aziridyl group, an azaindolyl group, an isoindolyl group, an indazolyl group, a purine group (purine), a pteridyl group (pteridine), a beta-carboline group, a naphthyridyl group (naphthyridine), a ter-pyridyl group, a phenazinyl group, an imidazopyridyl group, a pyropyridyl group, an azepine group, a pyrazolyl group, a dibenzofuranyl group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. Two or more heteroarylamine groups which the heteroaryl group includes may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the N-arylheteroarylamine group and the N-alkylheteroarylamine group are the same as the above-described examples of the heteroaryl group.

In the present specification, the heterocyclic group may be monocyclic or polycyclic, may be an aromatic ring, an aliphatic ring, or a condensed ring of the aromatic ring and the aliphatic ring, and may be selected from the examples of the heteroaryl group.

In the present specification, an aromatic ring group may be monocyclic or polycyclic, and may be selected from the examples of the aryl group.

In the present specification, a divalent to tetravalent aromatic ring group may be monocyclic or polycyclic, and means that there are two bonding positions in the aryl group, that is, a divalent to tetravalent group. The above-described description on the aryl group may be applied, except that the aromatic ring groups are each a divalent to tetravalent group.

In the present specification, the arylene group means that there are two bonding positions in an aryl group, that is, a divalent group. The above-described description on the aryl group may be applied, except that the arylene groups are each a divalent group.

In the present specification, in a substituted or unsubstituted ring formed by combining adjacent groups with each other, the "ring" means a substituted or unsubstituted hydrocarbon ring; or a substituted or unsubstituted hetero ring.

In the present specification, a hydrocarbon ring may be an aromatic ring, an aliphatic ring, or a condensed ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more atoms other than carbon, that is, one or more heteroatoms, and specifically, the heteroatom may include one or more atoms selected from the group consisting of O, N, Se, and S, and the like. The hetero ring may be monocyclic or polycyclic, may be an aromatic ring, an aliphatic ring, or a condensed ring of the aromatic ring and the aliphatic ring, and may be selected from the examples of the heteroaryl group, except for the hetero ring which is not monovalent.

According to an exemplary embodiment of the present specification, in Chemical Formula 1, HAr is a substituted or unsubstituted nitrogen-containing heteroaryl group.

According to an exemplary embodiment of the present specification, in Chemical Formula 1, HAr is a substituted or unsubstituted monocyclic or polycyclic nitrogen-containing heteroaryl group having 2 to 60 carbon atoms.

According to an exemplary embodiment of the present specification, in Chemical Formula 1, HAr is a substituted or unsubstituted monocyclic or polycyclic nitrogen-containing heteroaryl group having 2 to 30 carbon atoms.

According to an exemplary embodiment of the present specification, in Chemical Formula 1, HAr is a substituted or unsubstituted pyrrole group, a substituted or unsubstituted imidazolyl group, a substituted or unsubstituted pyridyl group, a substituted or unsubstituted bipyridyl group, a substituted or unsubstituted pyrimidyl group, a substituted or unsubstituted triazinyl group, a substituted or unsubstituted triazolyl group, a substituted or unsubstituted acridyl group, a substituted or unsubstituted pyridazinyl group, a substituted or unsubstituted pyrazinyl group, a substituted or unsubstituted quinolinyl group, a substituted or unsubstituted quinazolinyl group, a substituted or unsubstituted quinoxalinyl group, a substituted or unsubstituted phthalazinyl group, a substituted or unsubstituted pyridopyrimidyl group, a substituted or unsubstituted pyridopyrazinyl group, a substituted or unsubstituted pyrazinopyrazinyl group, a substituted or unsubstituted isoquinolinyl group, a substituted or unsubstituted indolyl group, a substituted or unsubstituted carbazolyl group, a substituted or unsubstituted benzimidazolyl group, a substituted or unsubstituted benzothiazolyl group, a substituted or unsubstituted benzocarbazolyl group, a substituted or unsubstituted phenanthrolinyl group (phenanthroline), a substituted or unsubstituted aziridyl group, a substituted or unsubstituted azaindolyl group, a substituted or unsubstituted isoindolyl group, a substituted or unsubstituted indazolyl group, a substituted or unsubstituted purine group (purine), a substituted or unsubstituted pteridyl group (pteridine), a substituted or unsubstituted beta-carboline group, a substituted or unsubstituted naphthyridyl group (naphthyridine), a substituted or unsubstituted ter-pyridyl group, a substituted or unsubstituted phenazinyl group, a substituted or unsubstituted imidazopyridyl group, a substituted or unsubstituted pyropyridyl group, a substituted or unsubstituted azepine group, or a substituted or unsubstituted pyrazolyl group.

According to an exemplary embodiment of the present specification, in Chemical Formula 1, HAr is a pyrrole group, an imidazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an iso-quinolinyl group, an indolyl group, a carbazolyl group, a benzimidazolyl group, a benzothiazolyl group, a benzocarbazolyl group, a phenanthrolinyl group (phenanthroline), an aziridyl group, an azaindolyl group, an isoindolyl group, an indazolyl group, a purine group (purine), a pteridyl group (pteridine), a beta-carboline group, a naphthyridyl group (naphthyridine), a ter-pyridyl group, a phenazinyl group, an imidazopyridyl group, a pyropyridyl group, an azepine group, or a pyrazolyl group.

According to an exemplary embodiment of the present specification, in Chemical Formula 1, HAr is represented by the following Chemical Formula A or B.

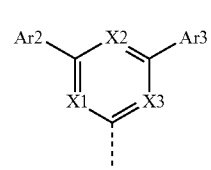

[Chemical Formula A]

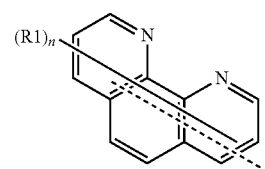

[Chemical Formula B]

In Chemical Formulae A and B,

X1 to X3 are the same as or different from each other, and are each independently N, CH or CD, at least one of X1 to X3 is N, Ar2, Ar3, and R1 are the same as or different from each other, and are each independently hydrogen; or a substituted or unsubstituted aryl group, or combine with an adjacent group to form a substituted or unsubstituted ring, n is an integer of 1 to 7, when n is 2 or more, two or more R1's are the same as or different from each other, and --- is a moiety linked to L1.

According to an exemplary embodiment of the present specification, Chemical Formula 1 is represented by the following Chemical Formula 2 or 3.

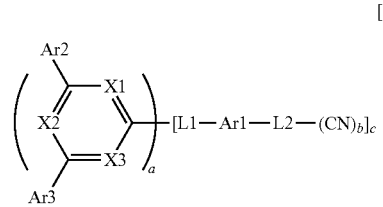

[Chemical Formula 2]

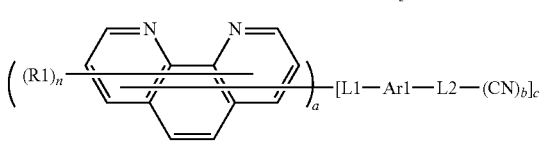

[Chemical Formula 3]

In Chemical Formulae 2 and 3, the definitions of a, b, c, L1, L2, and Ar1 are the same as those in Chemical Formula 1, the definitions of X1 to X3, Ar2, and Ar3 are the same as those in Chemical Formula A, and the definitions of R1 and n are the same as those in Chemical Formula B.

According to an exemplary embodiment of the present specification, Chemical Formula 1 is represented by any one of the following Chemical Formulae 2-1 to 2-3.

[Chemical Formula 2-1]

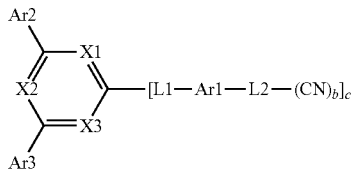

[Chemical Formula 2-2]

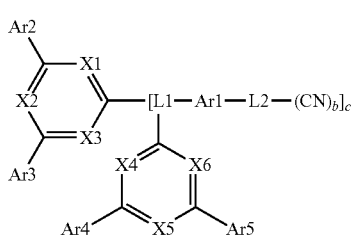

[Chemical Formula 2-3]

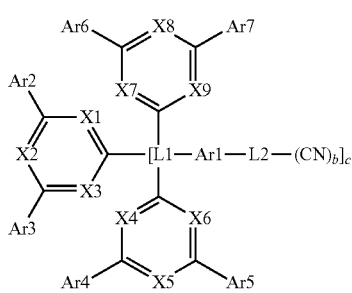

In Chemical Formulae 2-1 to 2-3, the definitions of b, c, L1, L2, and Ar1 are the same as those in Chemical Formula 1, the definitions of X1 to X3, Ar2, and Ar3 are the same as those in Chemical Formula A, X4 to X9 are the same as or different from each other, and are each independently N, CH or CD, at least one of X4 to X6 is N, at least one of X7 to X9 is N, and Ar4 to Ar7 are the same as or different from each other, and are each independently hydrogen; or a substituted or unsubstituted aryl group, or combine with an adjacent group to form a substituted or unsubstituted ring.

According to an exemplary embodiment of the present specification, Chemical Formula 1 is represented by any one of the following Chemical Formulae 3-1 to 3-3.

[Chemical Formula 3-1]

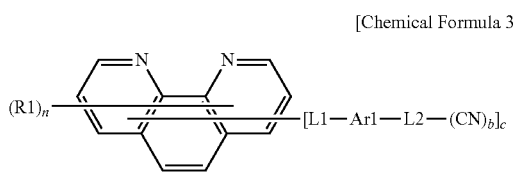

[Chemical Formula 3-2]

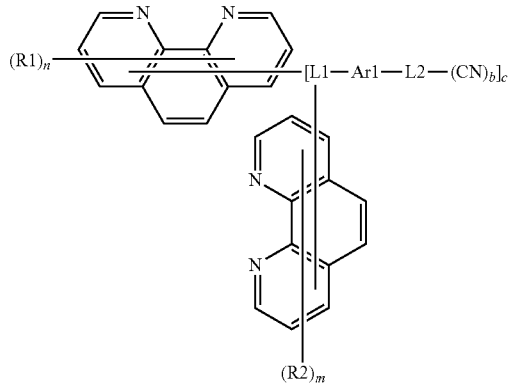

[Chemical Formula 3-3]

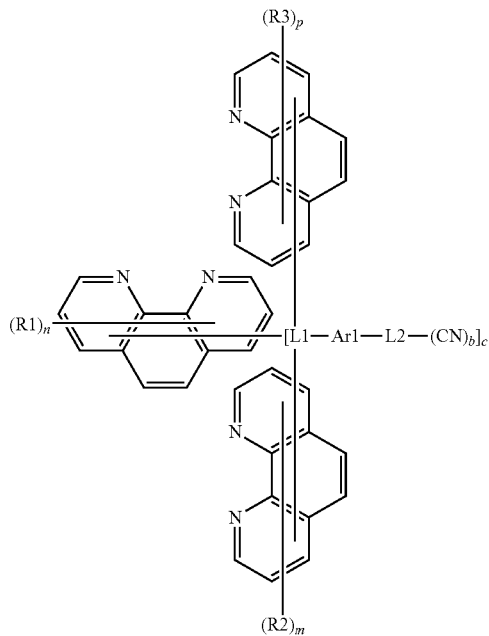

In Chemical Formulae 3-1 to 3-3, the definitions of b, c, L1, L2, and Ar1 are the same as those in Chemical Formula 1, the definitions of R1 and n are the same as those in Chemical Formula B, R2 and R3 are the same as or different from each other, and are each independently hydrogen; or a substituted or unsubstituted aryl group, or combine with an adjacent group to form a substituted or unsubstituted ring, m and p are each an integer of 1 to 7, and when m and p are each 2 or more, two or more structures in the parenthesis are the same as or different from each other.

According to an exemplary embodiment of the present specification, Chemical Formula A is represented by any one of the following Chemical Formulae A-1 to A-7.

[Chemical Formula A-1]

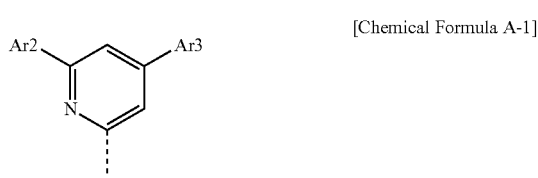

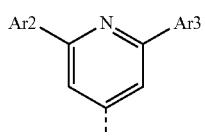
[Chemical Formula A-2]

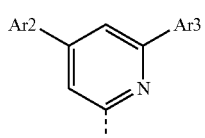
[Chemical Formula A-3]

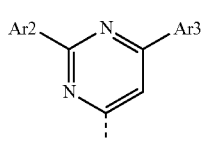
[Chemical Formula A-4]

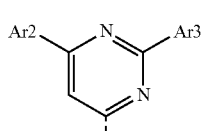
[Chemical Formula A-5]

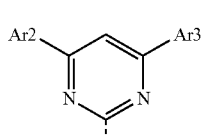
[Chemical Formula A-6]

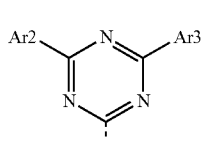
[Chemical Formula A-7]

In Chemical Formulae A-1 to A-7, the definitions of Ar2 and Ar3 are the same as those in Chemical Formula A, and --- is a moiety linked to L1.

According to an exemplary embodiment of the present specification, Chemical Formula B is represented by any one of the following Chemical Formulae B-1 to B-4.

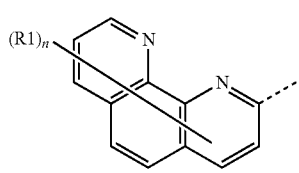
[Chemical Formula B-1]

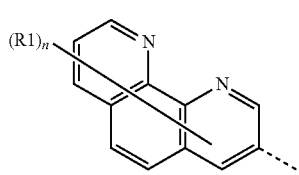
[Chemical Formula B-2]

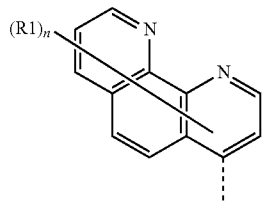
[Chemical Formula B-3]

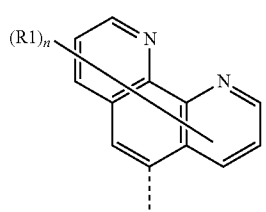
[Chemical Formula B-4]

In Chemical Formulae B-1 to B-4, the definitions of R1 and n are the same as those in Chemical Formula B, and --- is a moiety linked to L1.

According to an exemplary embodiment of the present specification, in Chemical Formula 1, L1 and L2 are the same as or different from each other, and are each independently a substituted or unsubstituted monocyclic or polycyclic divalent to tetravalent aromatic ring group having 6 to 30 carbon atoms.

According to an exemplary embodiment of the present specification, in Chemical Formula 1, L1 and L2 are the same as or different from each other, and are each independently a substituted or unsubstituted monocyclic or polycyclic divalent to tetravalent aromatic ring group having 6 to 20 carbon atoms.

According to an exemplary embodiment of the present specification, in Chemical Formula 1, L1 and L2 are the same as or different from each other, and are each independently a substituted or unsubstituted divalent to tetravalent phenyl group; a substituted or unsubstituted divalent to tetravalent biphenyl group; a substituted or unsubstituted divalent to tetravalent terphenyl group; or a substituted or unsubstituted divalent to tetravalent fluorenyl group.

According to an exemplary embodiment of the present specification, in Chemical Formula 1, L1 and L2 are the same as or different from each other, and are each independently a divalent to tetravalent phenyl group; a divalent to tetravalent biphenyl group; a divalent to tetravalent terphenyl group; or a divalent to tetravalent fluorenyl group substituted with an alkyl group.

According to an exemplary embodiment of the present specification, in Chemical Formula 1, L1 is a divalent phenyl group; a trivalent phenyl group; or a trivalent terphenyl group.

According to an exemplary embodiment of the present specification, in Chemical Formula 1, L2 is a divalent phenyl group; a trivalent phenyl group; a divalent biphenyl group; a trivalent biphenyl group; or a divalent fluorenyl group substituted with a methyl group.

According to an exemplary embodiment of the present specification, in Chemical Formula 1, Ar1 is a direct bond; or a substituted or unsubstituted monocyclic or polycyclic arylene group having 6 to 30 carbon atoms.

According to an exemplary embodiment of the present specification, in Chemical Formula 1, Ar1 is a direct bond; or a substituted or unsubstituted monocyclic or polycyclic arylene group having 6 to 20 carbon atoms.

According to an exemplary embodiment of the present specification, in Chemical Formula 1, Ar1 is a direct bond; a substituted or unsubstituted phenylene group; a substituted or unsubstituted biphenylylene group; or a substituted or unsubstituted naphthylene group.

According to an exemplary embodiment of the present specification, in Chemical Formula 1, Ar1 is a direct bond; a phenylene group; a biphenylene group; or a naphthylene group.

According to an exemplary embodiment of the present specification, in Chemical Formula A, Ar2 and Ar3 are the same as or different from each other, and are each independently a substituted or unsubstituted monocyclic or polycyclic aryl group having 6 to 30 carbon atoms.

According to an exemplary embodiment of the present specification, in Chemical Formula A, Ar2 and Ar3 are the same as or different from each other, and are each independently a substituted or unsubstituted monocyclic or polycyclic aryl group having 6 to 20 carbon atoms.

According to an exemplary embodiment of the present specification, in Chemical Formula A, Ar2 and Ar3 are the same as or different from each other, and are each independently a substituted or unsubstituted phenyl group; or a substituted or unsubstituted biphenyl group.

According to an exemplary embodiment of the present specification, in Chemical Formula A, Ar2 and Ar3 are the same as or different from each other, and are each independently a phenyl group; or a biphenyl group.

According to an exemplary embodiment of the present specification, in Chemical Formula A-2, Ar4 and Ar5 are the same as or different from each other, and are each independently a substituted or unsubstituted monocyclic or polycyclic aryl group having 6 to 30 carbon atoms.

According to an exemplary embodiment of the present specification, in Chemical Formula A-2, Ar4 and Ar5 are the same as or different from each other, and are each independently a substituted or unsubstituted monocyclic or polycyclic aryl group having 6 to 20 carbon atoms.

According to an exemplary embodiment of the present specification, in Chemical Formula A-2, Ar4 and Ar5 are the same as or different from each other, and are each independently a substituted or unsubstituted phenyl group.

According to an exemplary embodiment of the present specification, in Chemical Formula A-2, Ar4 and Ar5 are a phenyl group.

According to an exemplary embodiment of the present specification, in Chemical Formula 1, b is 1 or 2.

According to an exemplary embodiment of the present specification, Chemical Formula 1 is selected from any one of the following compounds.

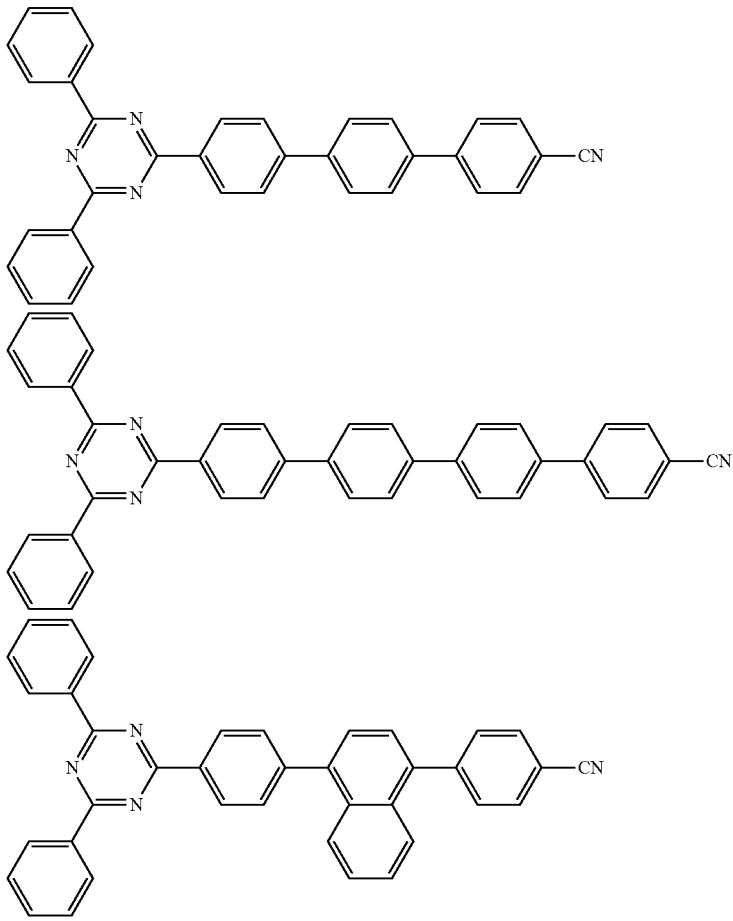

-continued
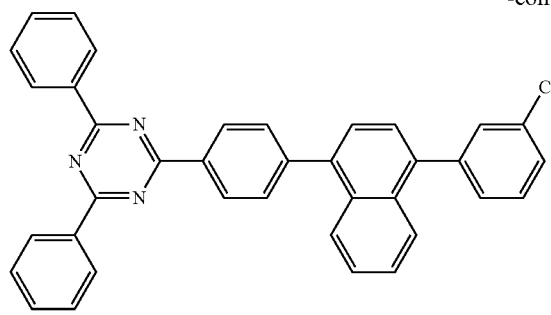
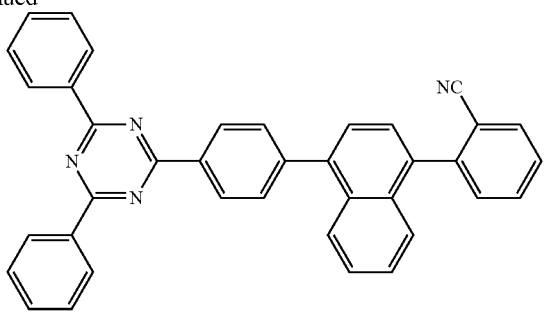
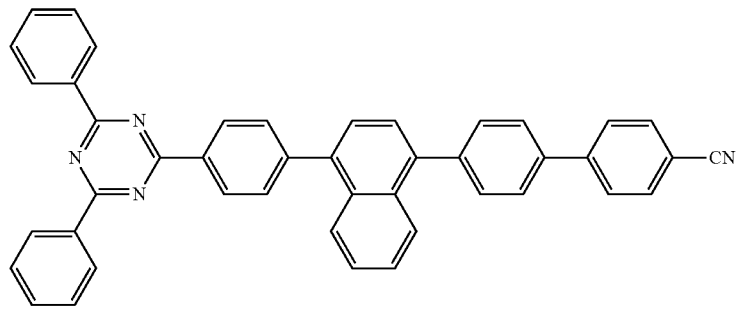
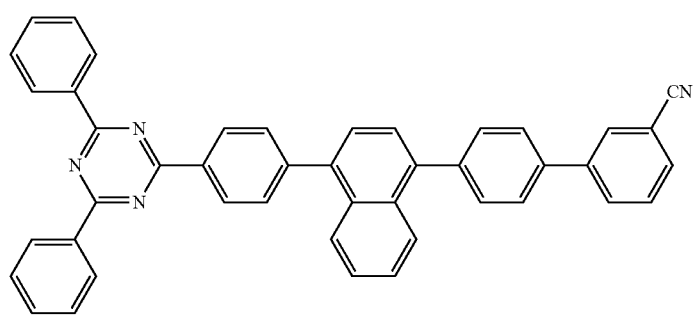
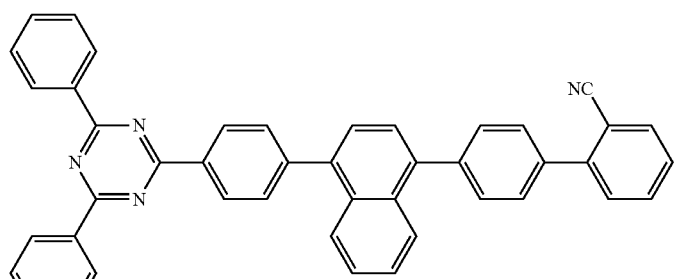
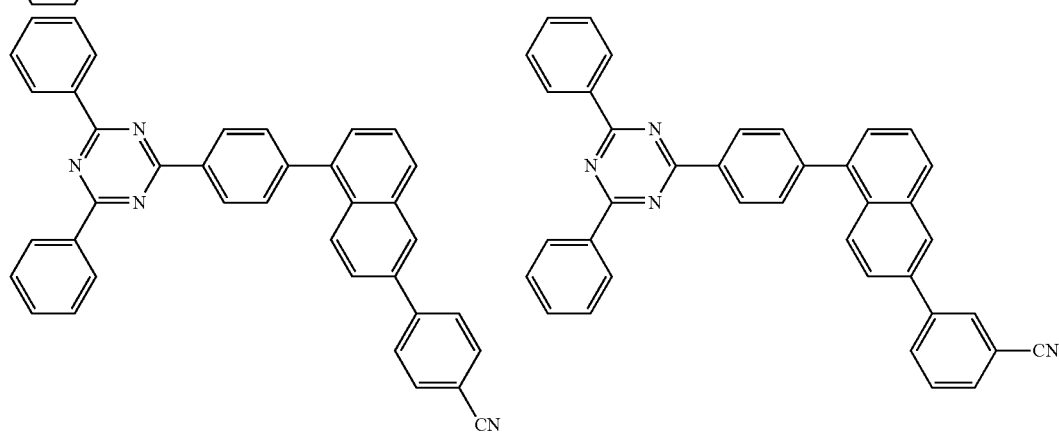

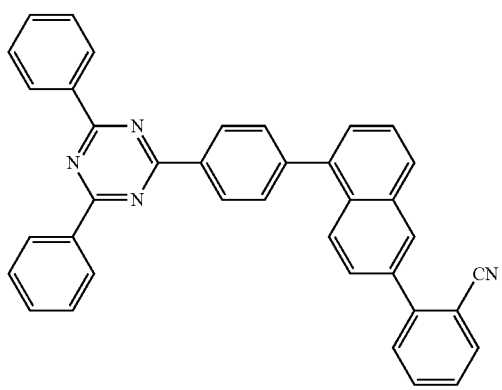
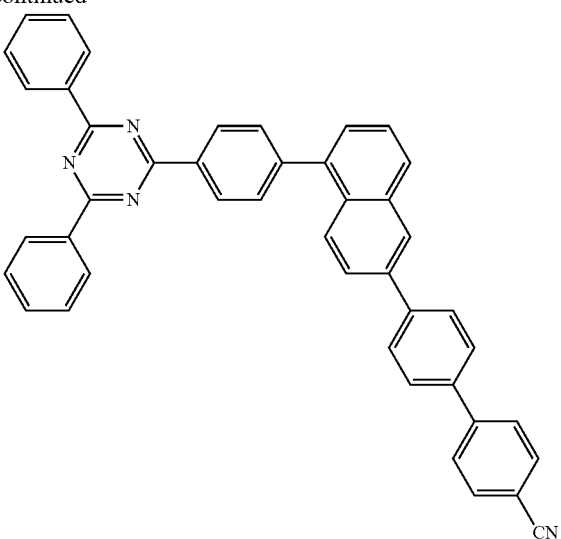
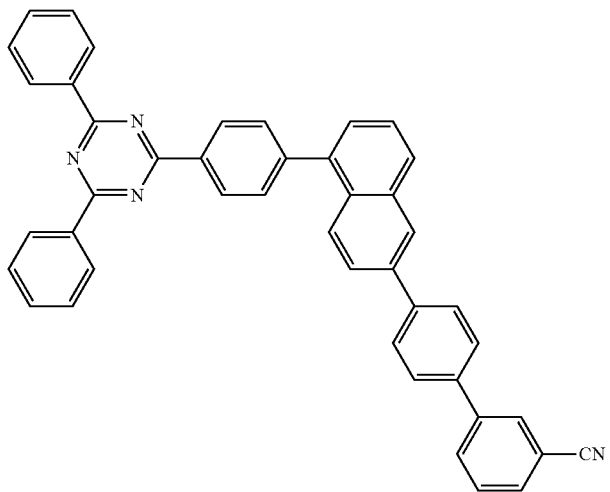
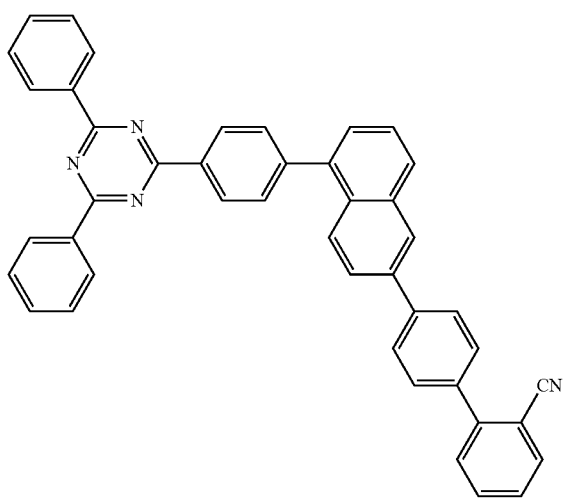

-continued
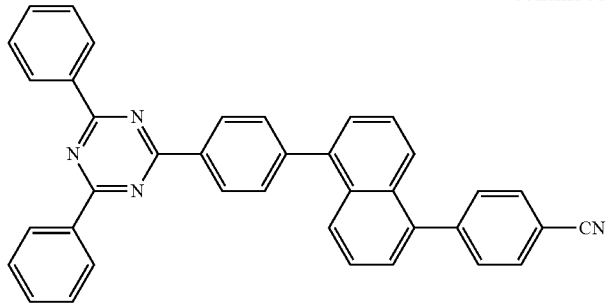
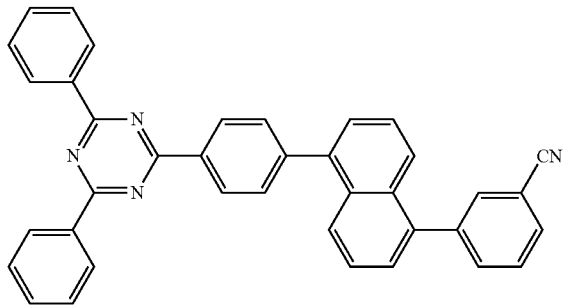
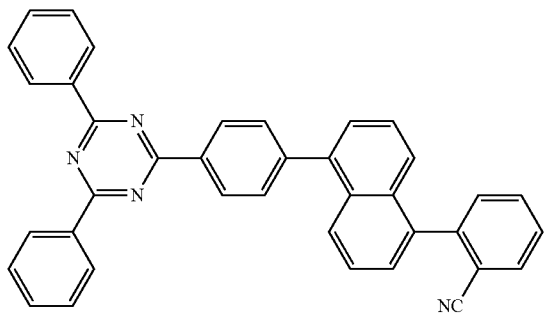
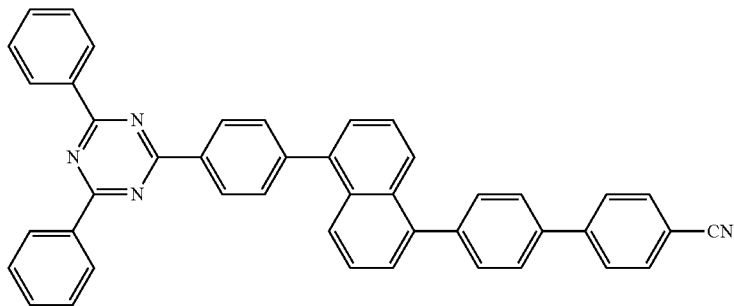
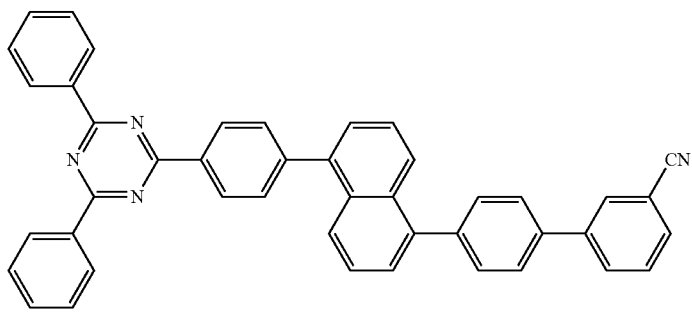

-continued
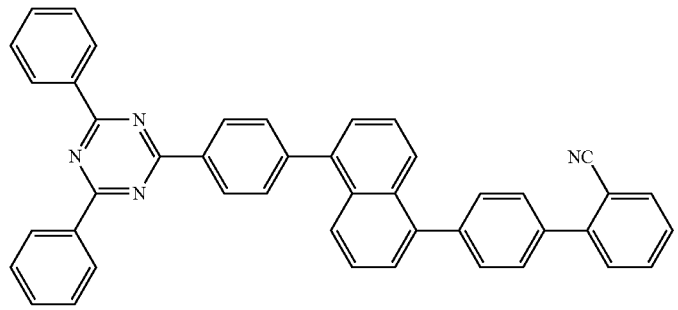
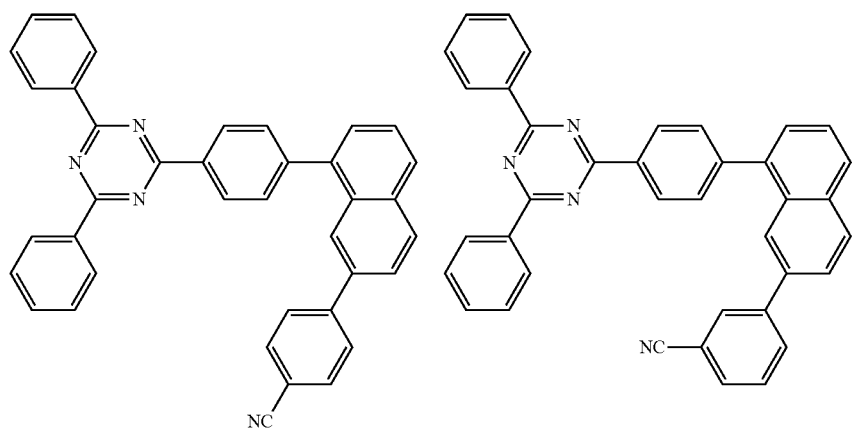
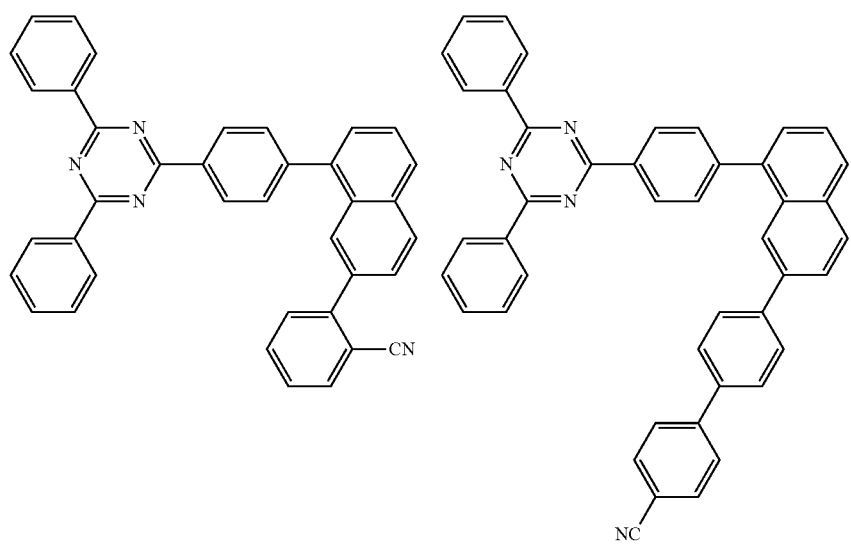

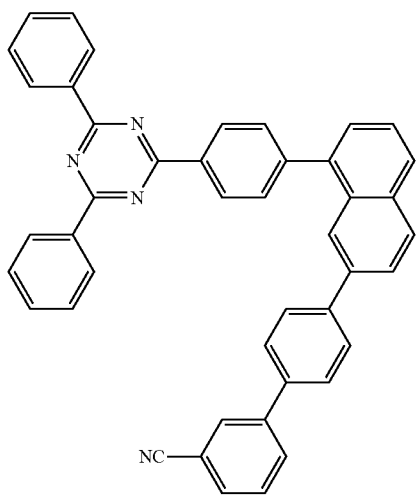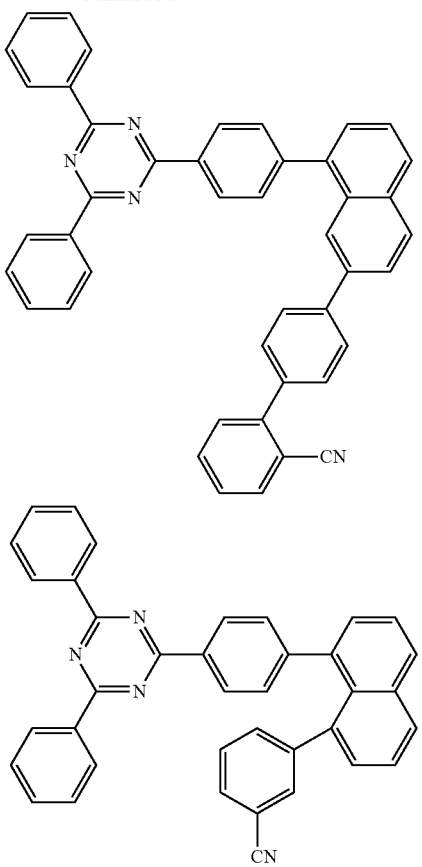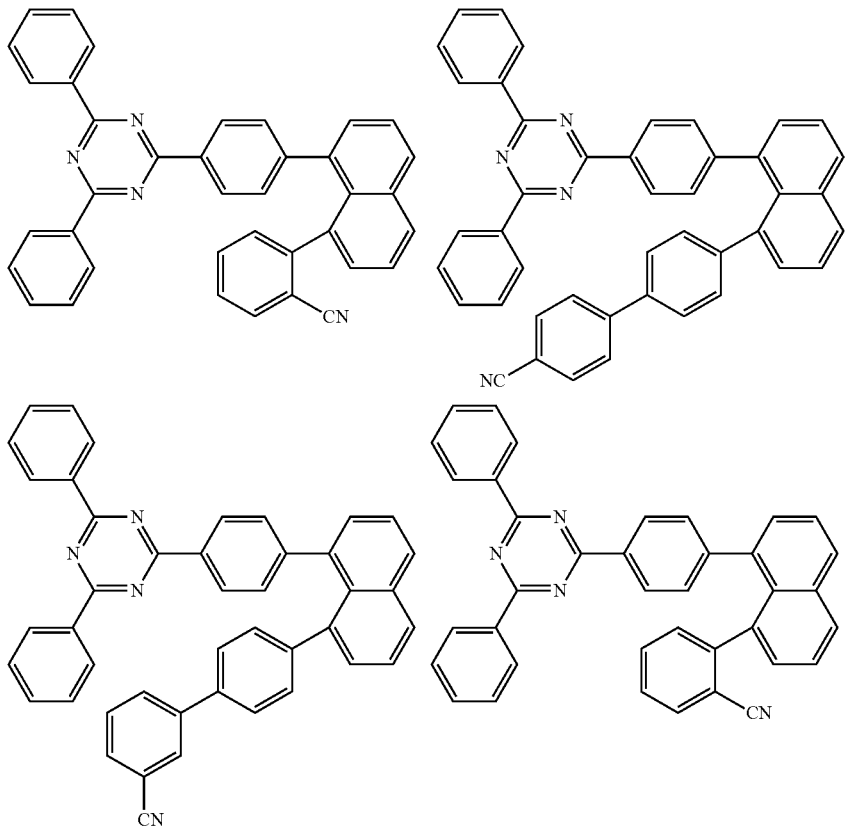

-continued
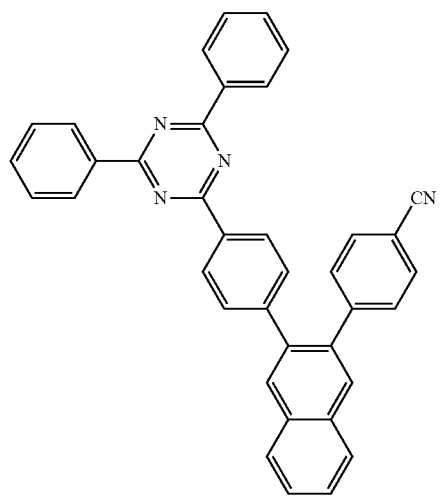
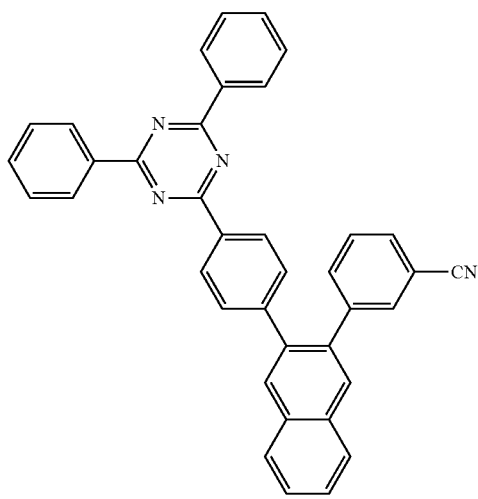
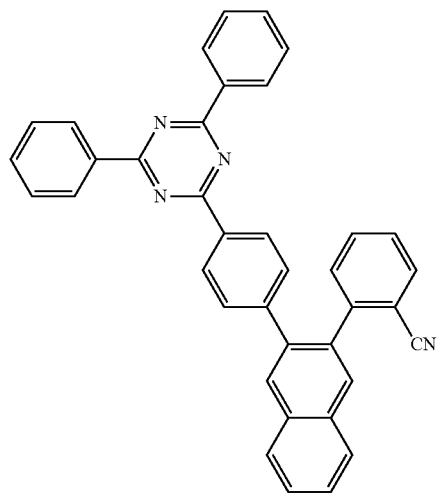
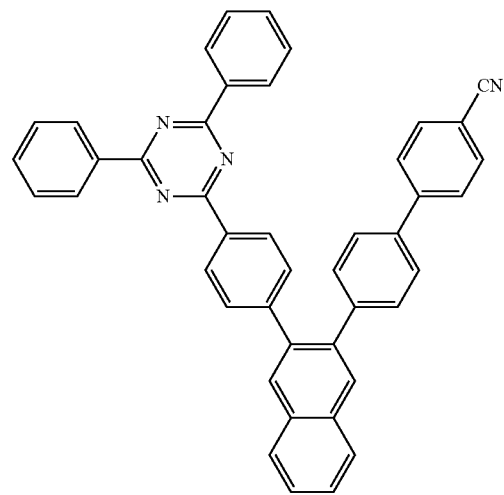
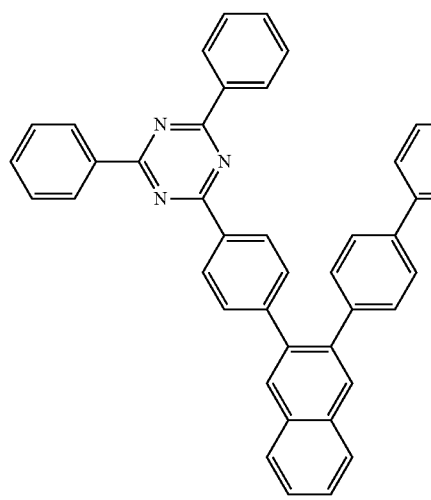
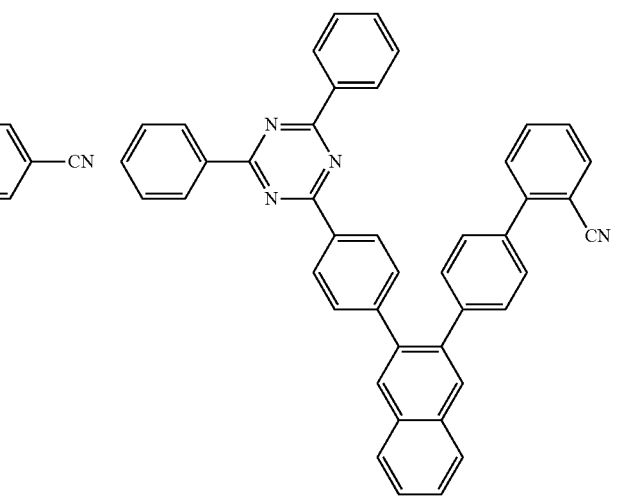

-continued
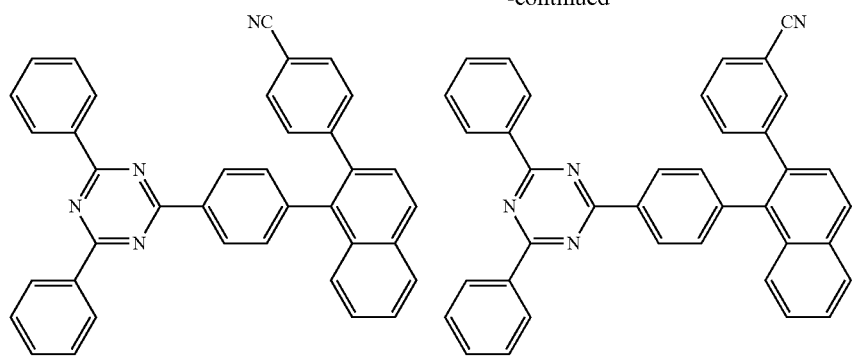
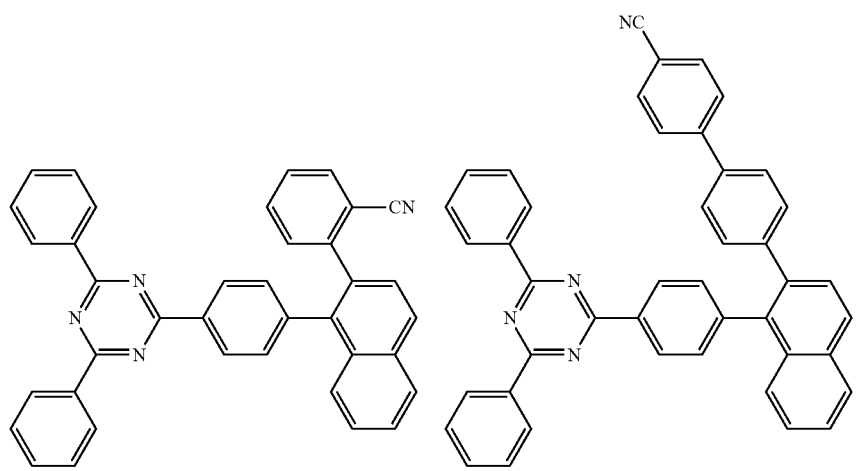
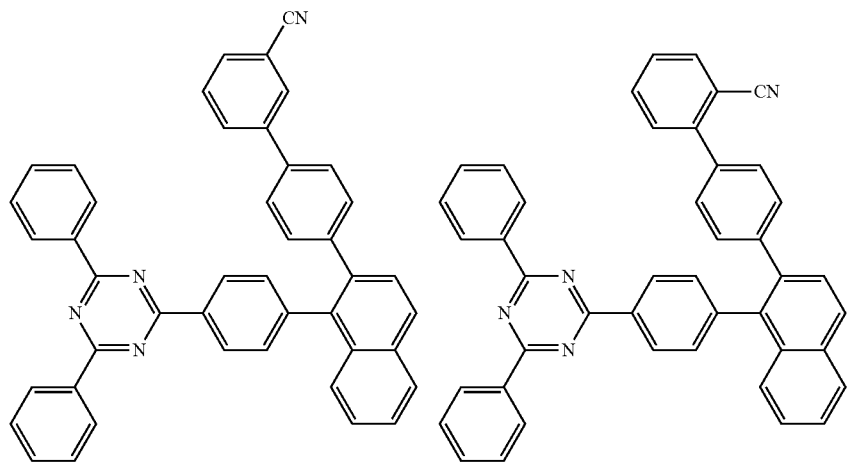

31
32
-continued
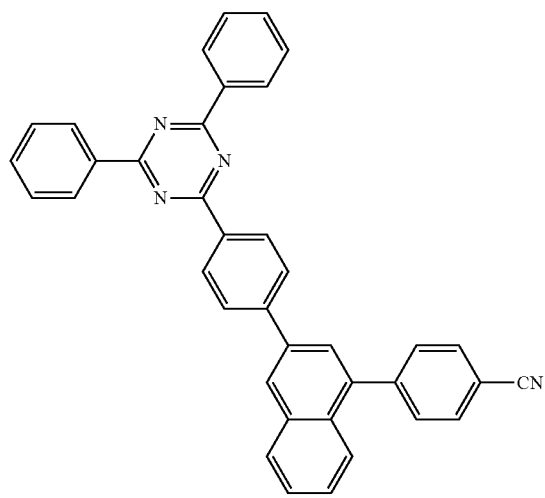
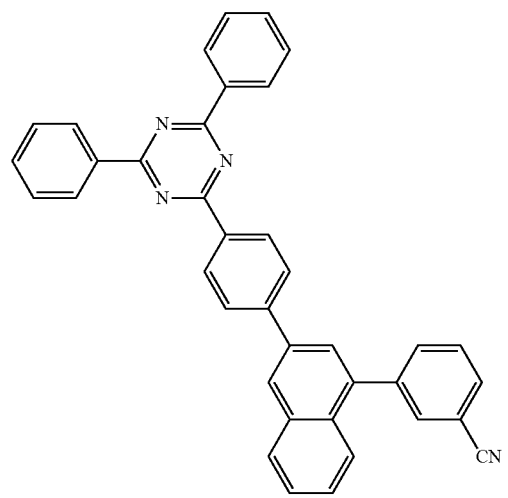
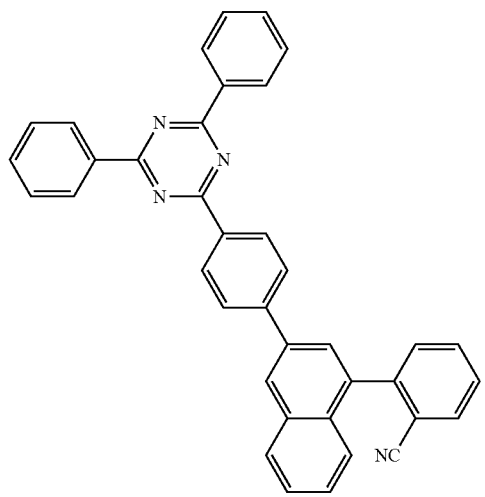
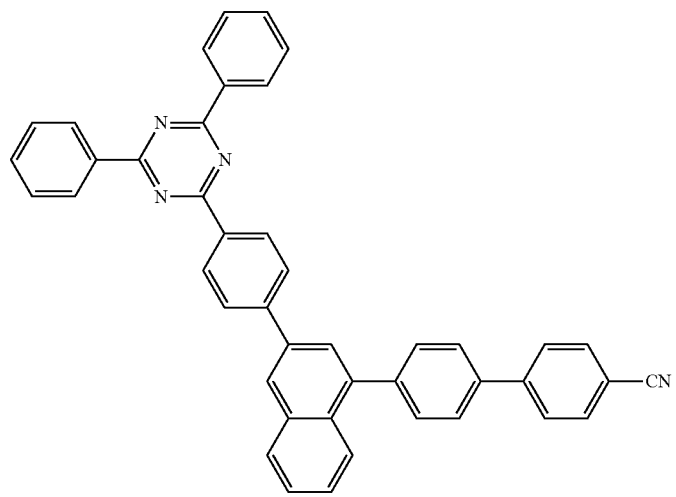
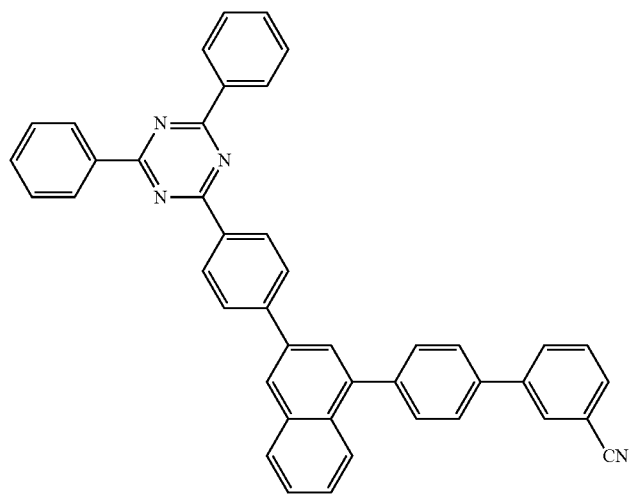

-continued
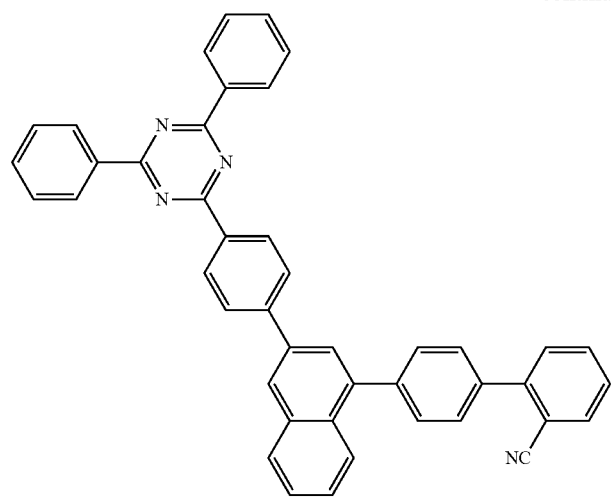
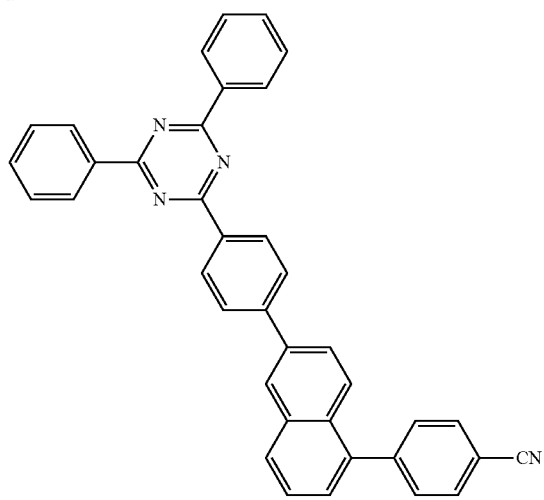
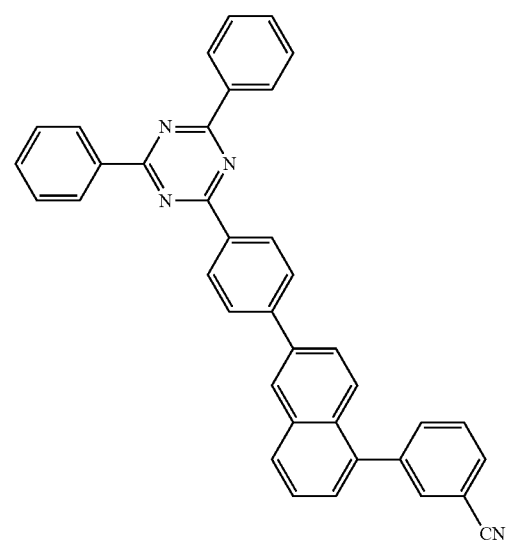
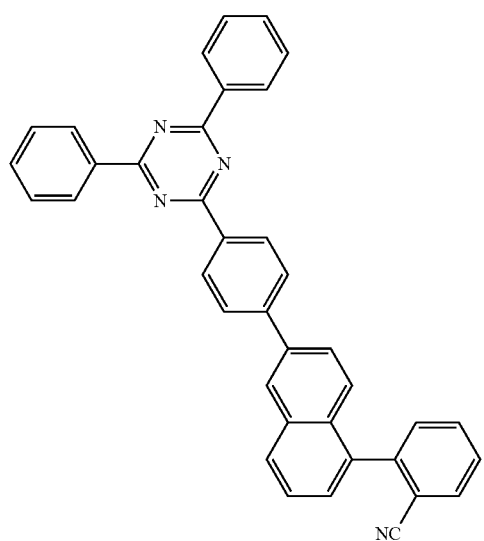
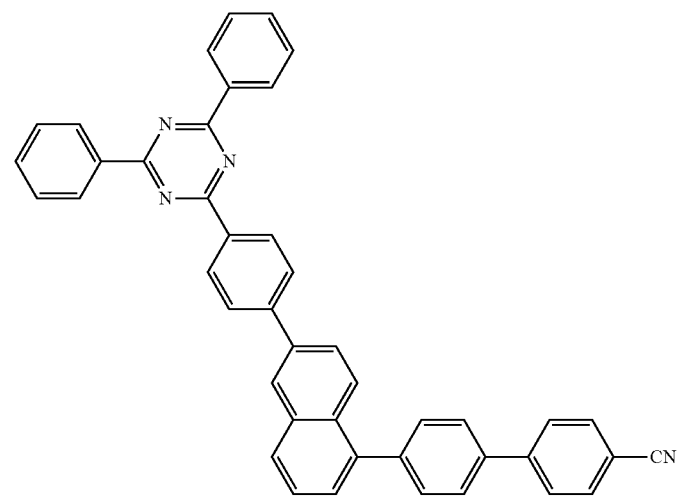

-continued
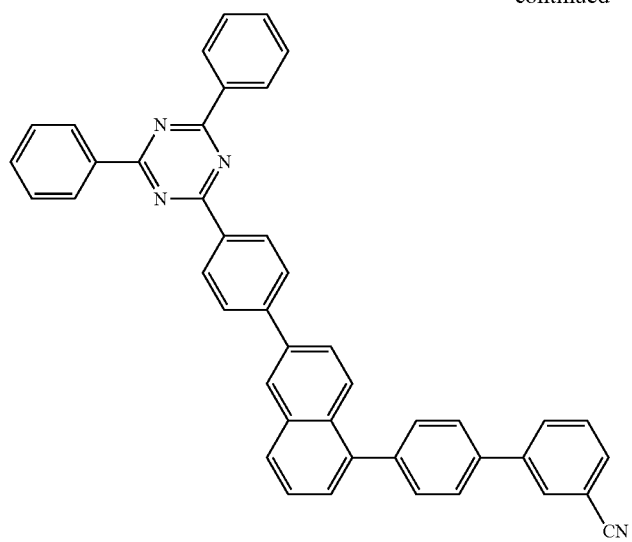
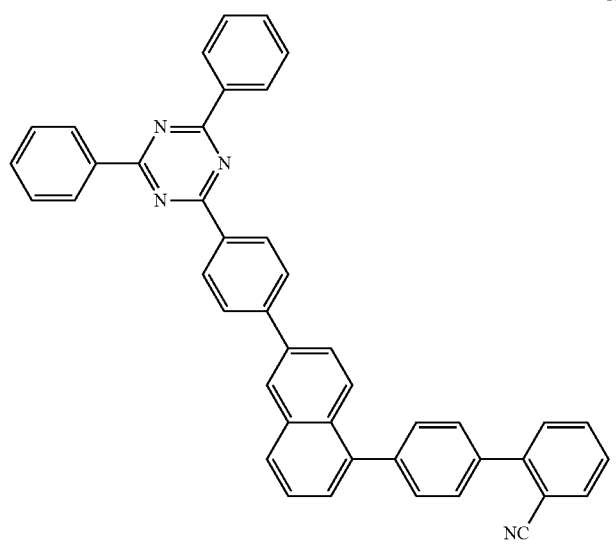
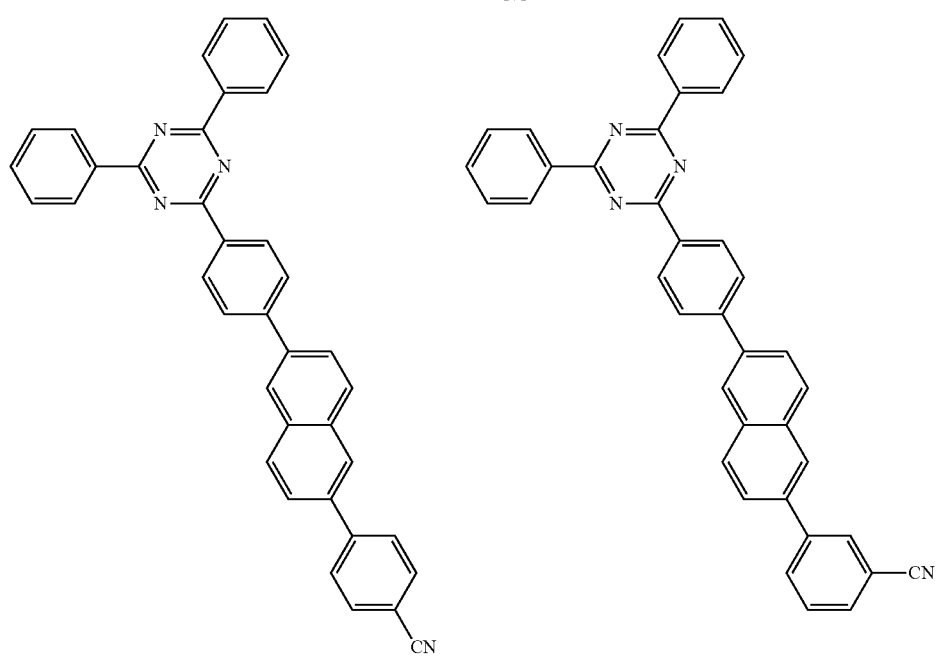

-continued
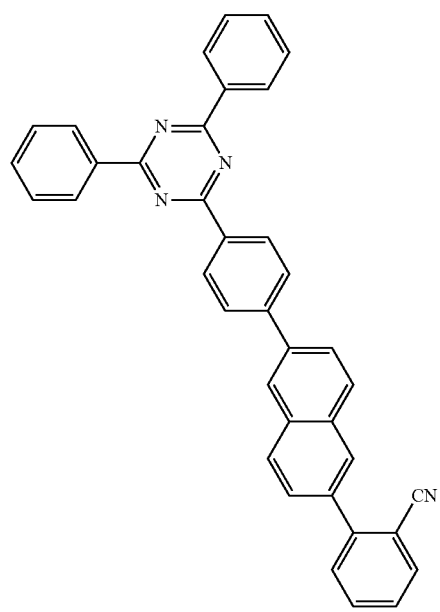
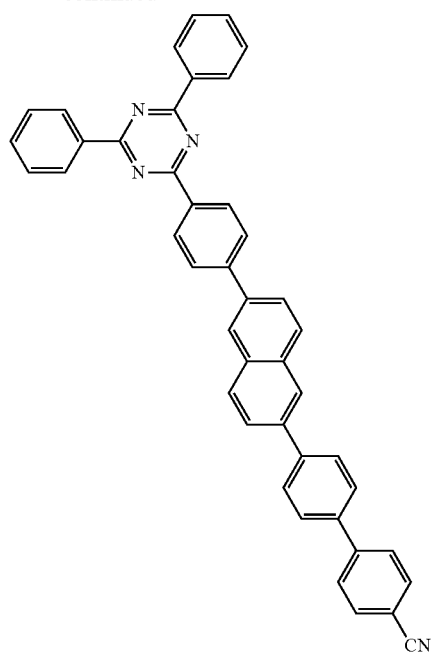
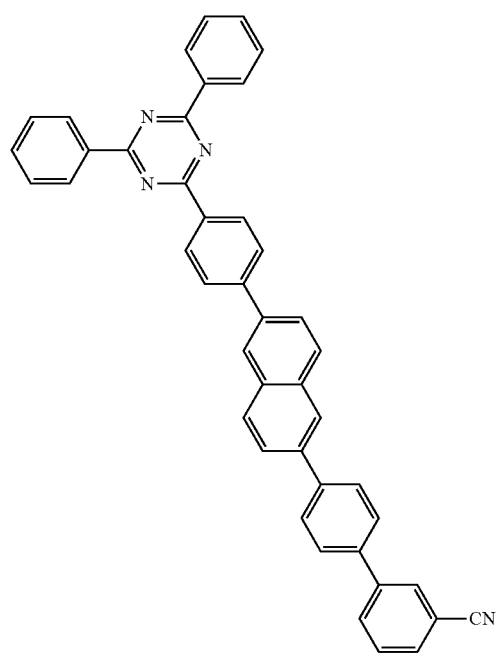
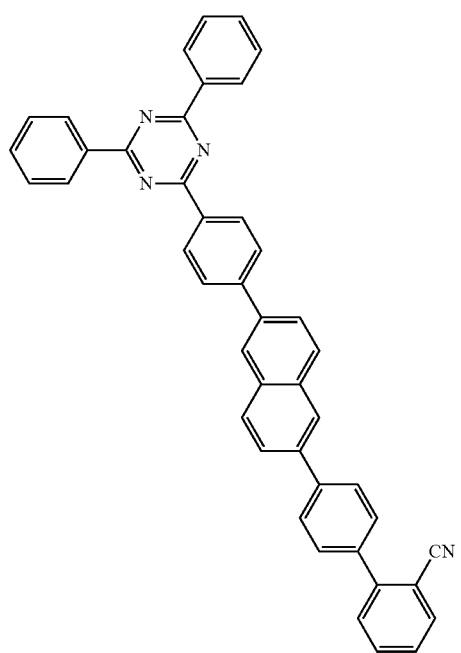

-continued
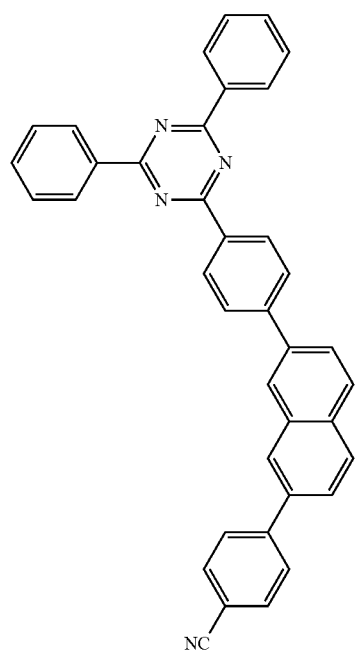
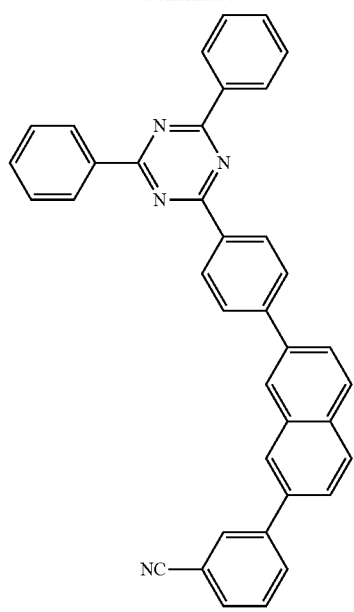
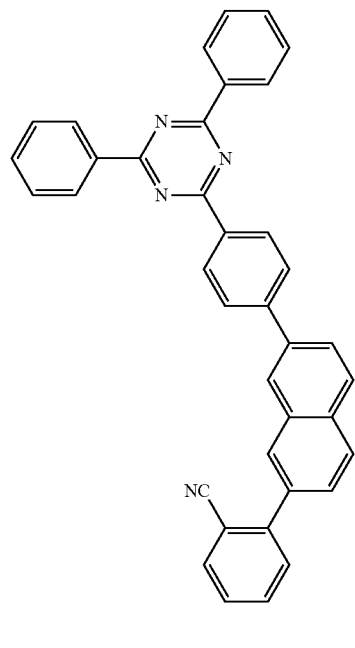

-continued
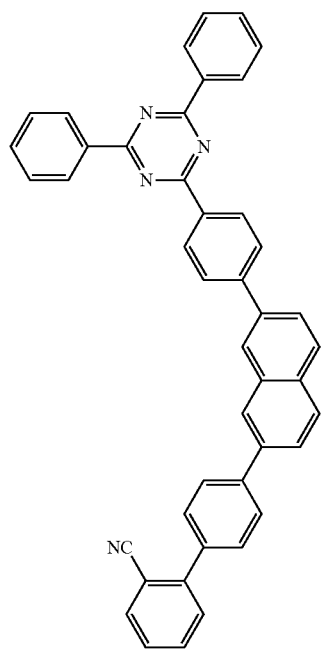
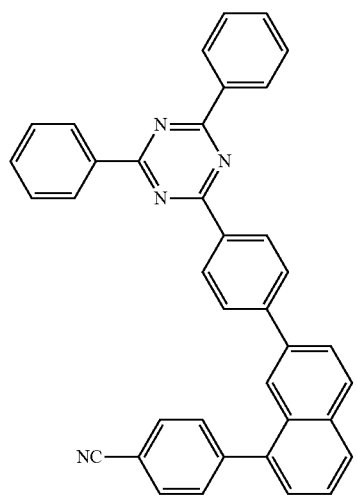
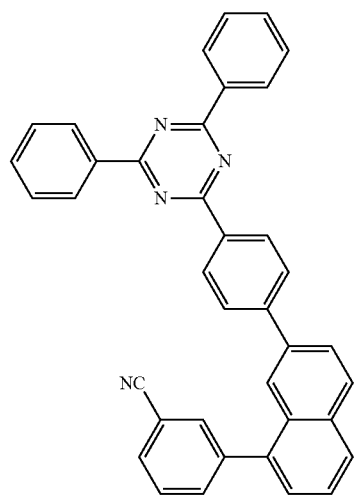
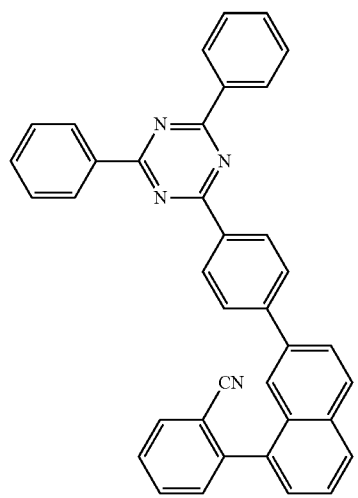
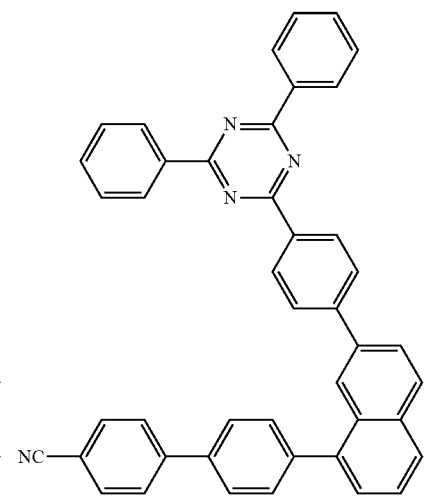
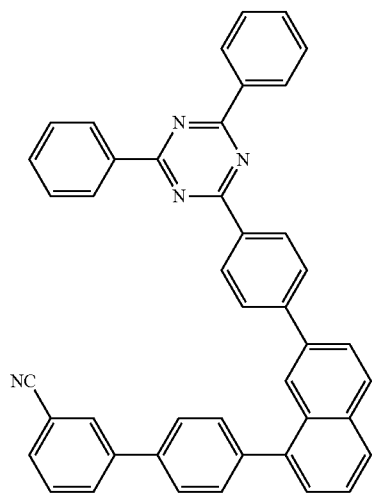
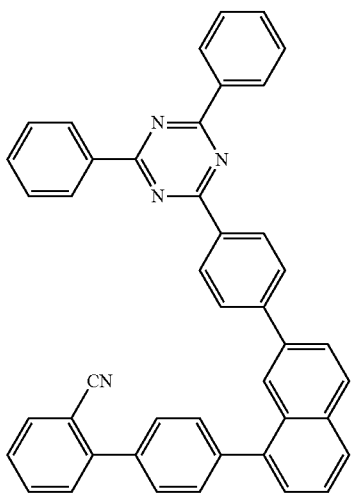
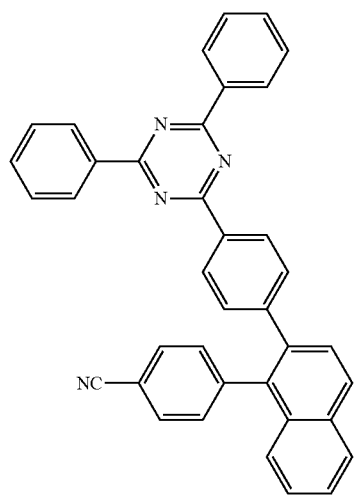

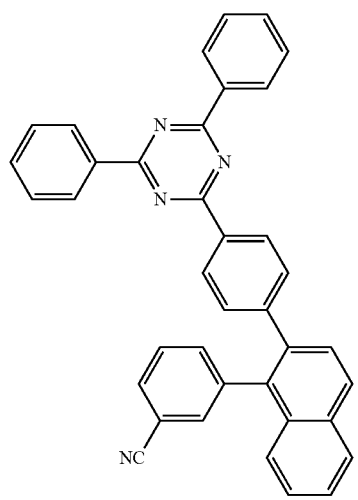
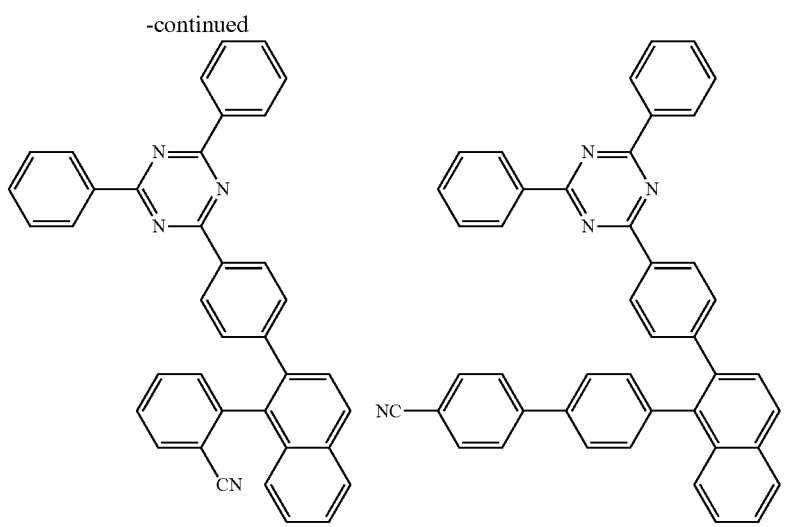
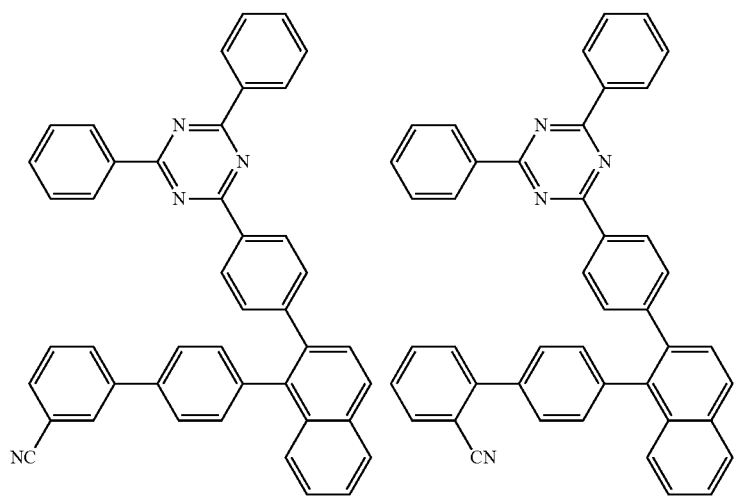
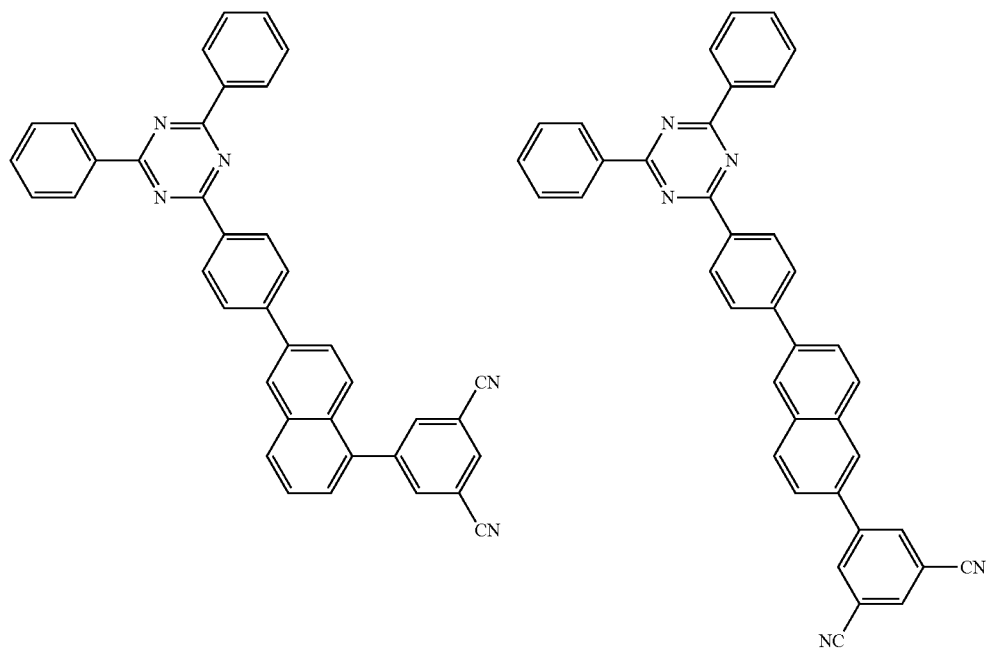

-continued
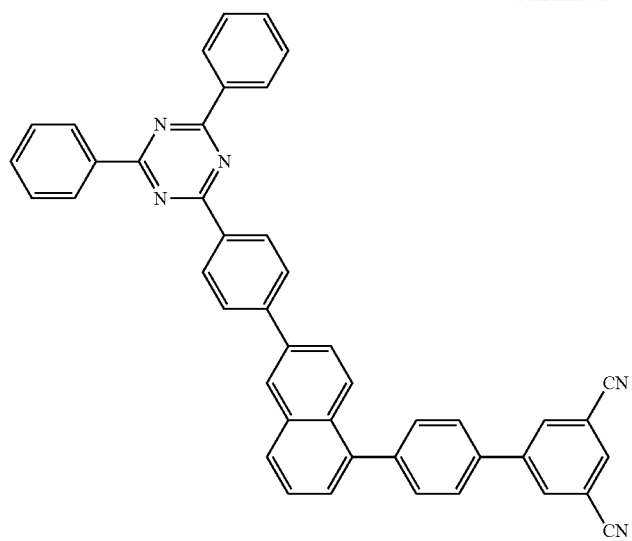
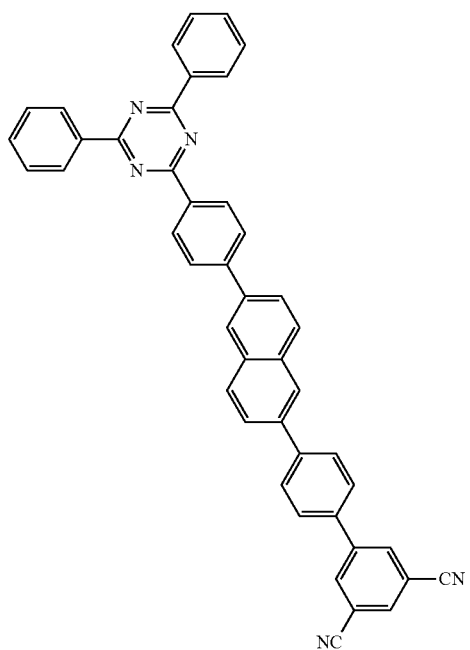
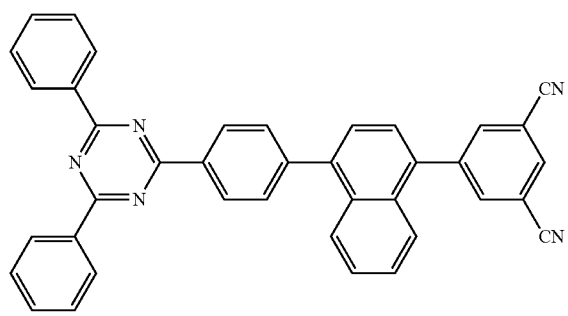
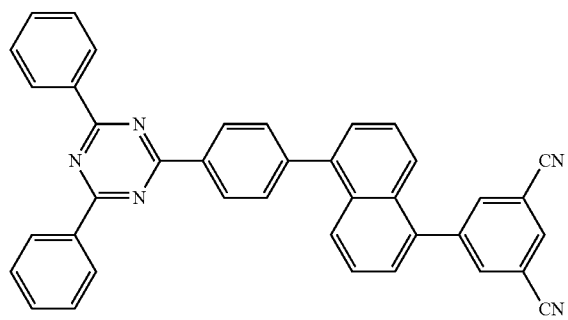
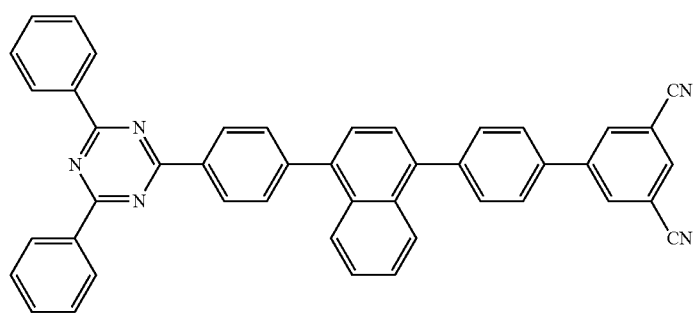

-continued
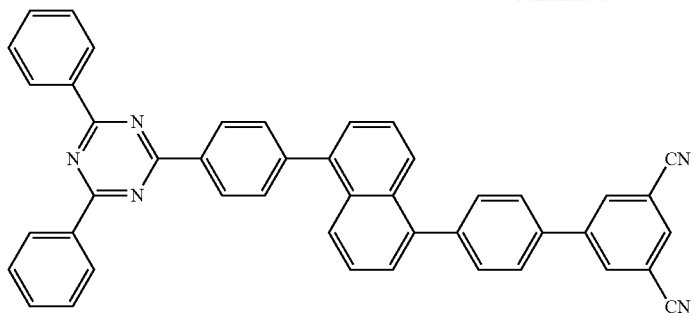
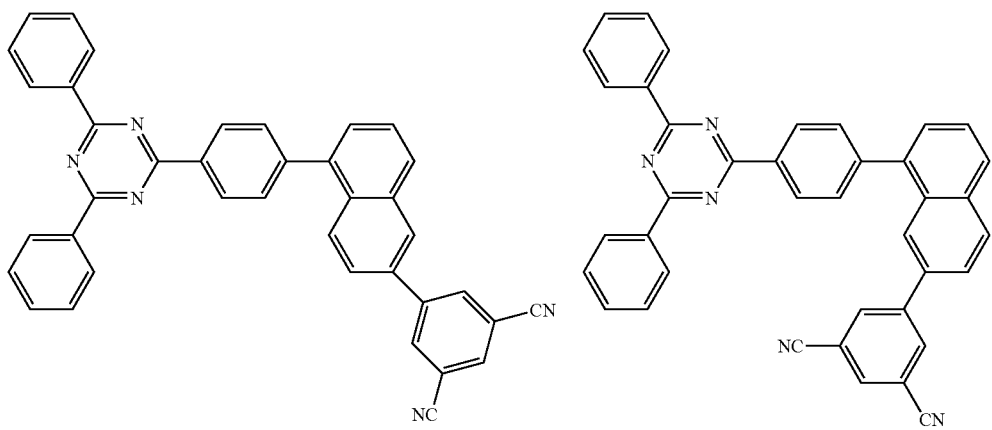
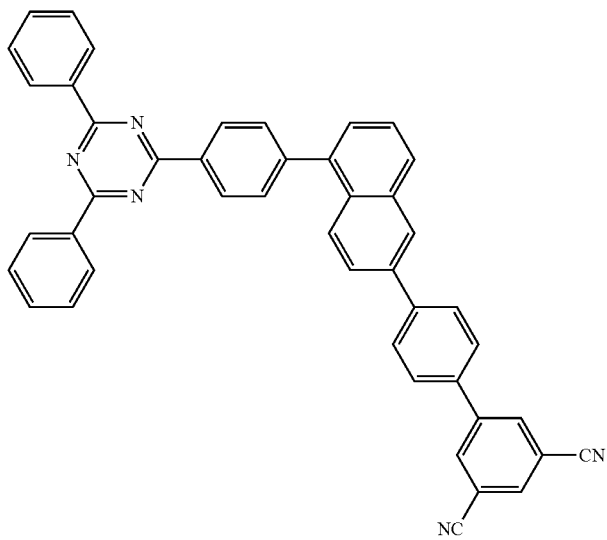

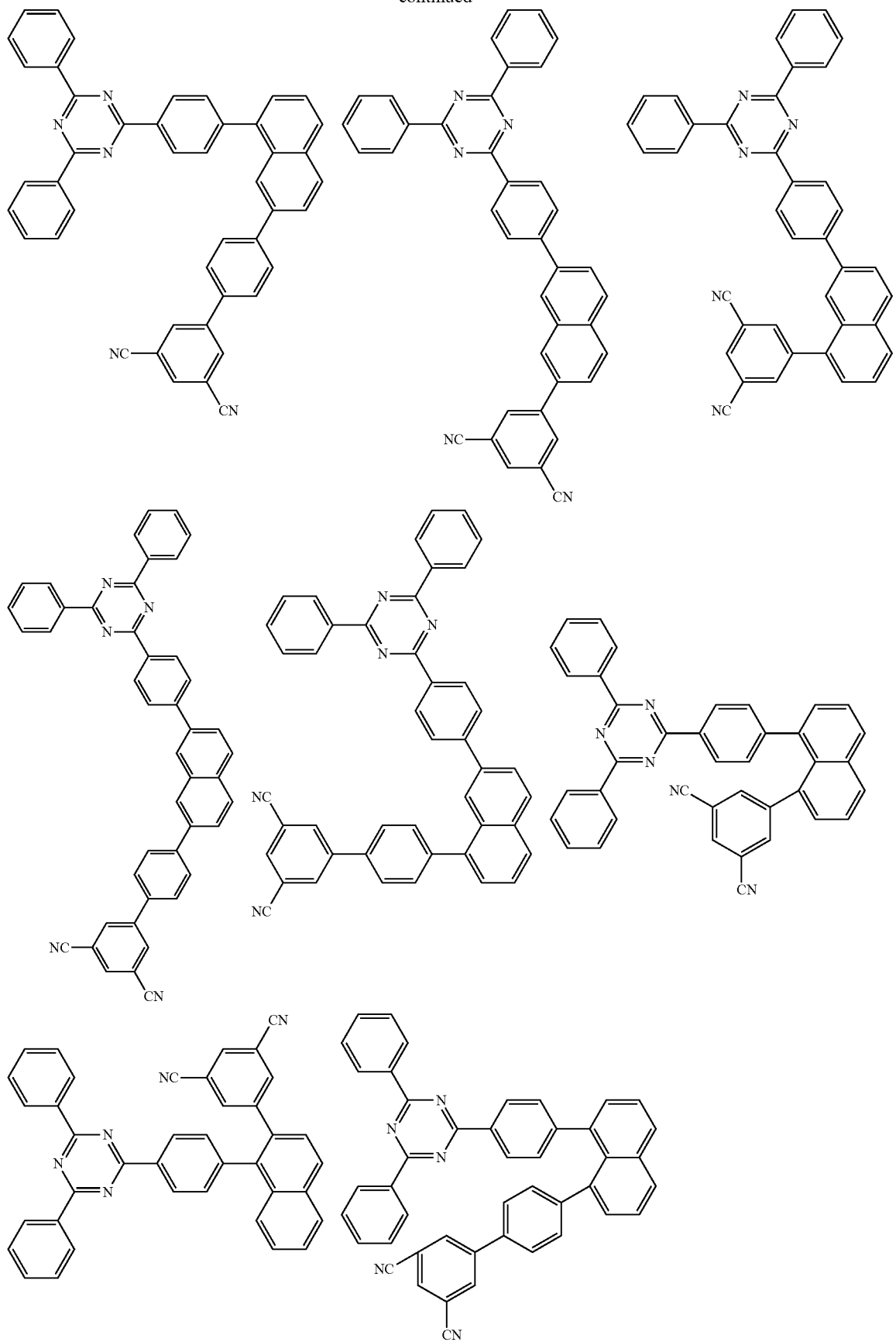

-continued
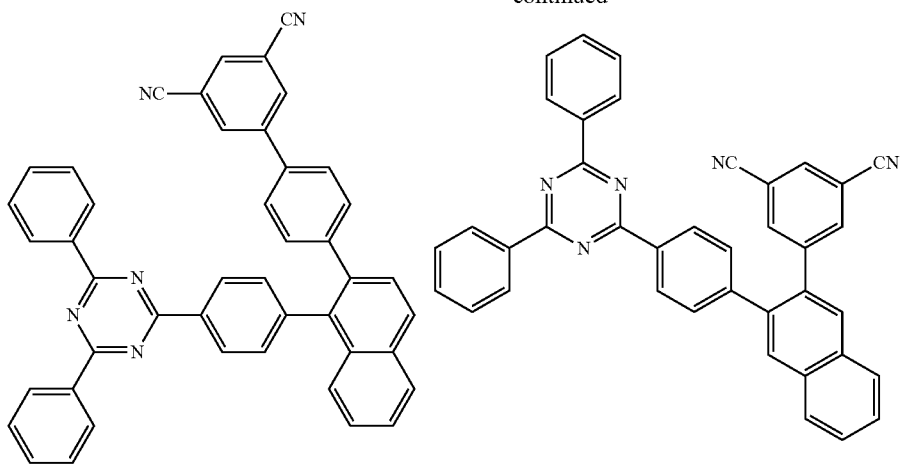
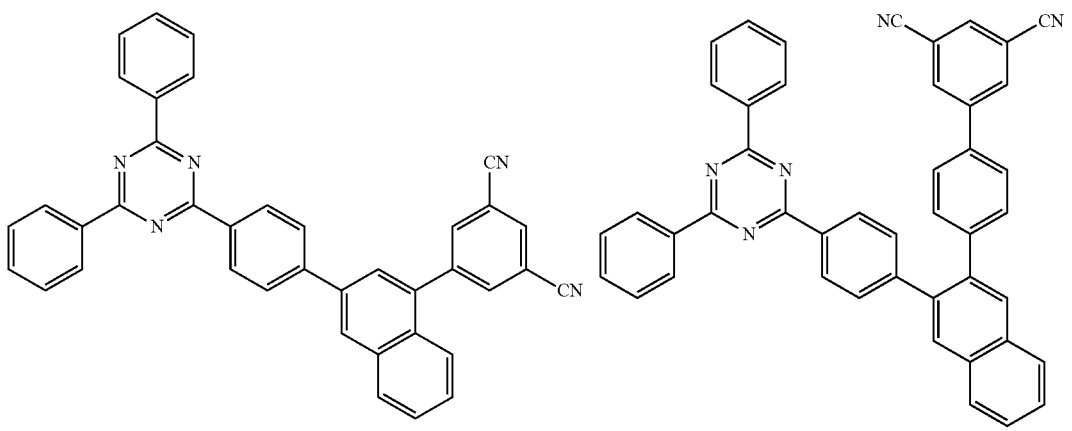
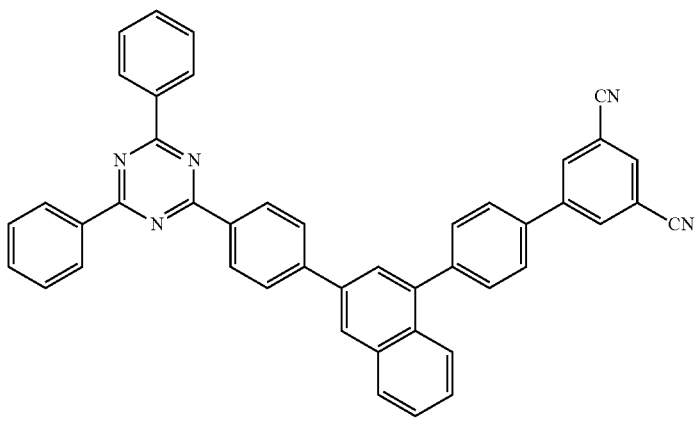

-continued
53
54
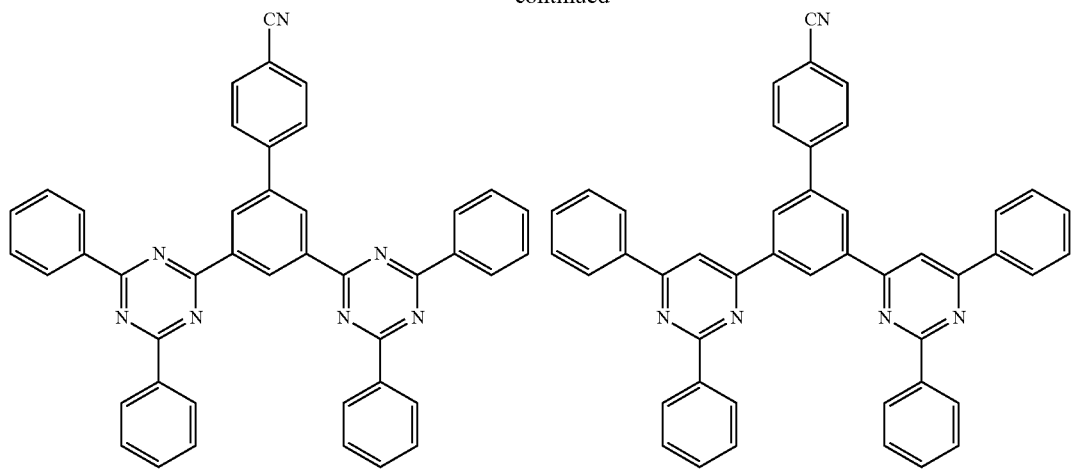
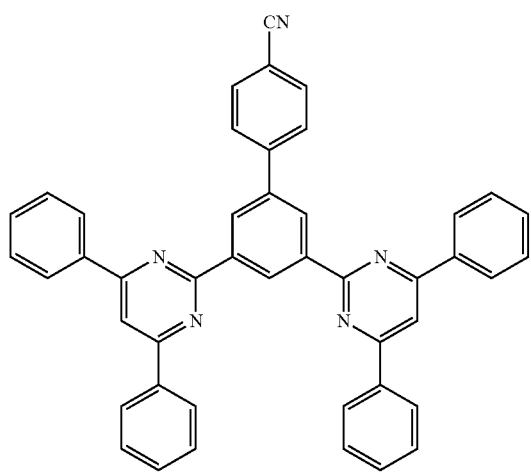
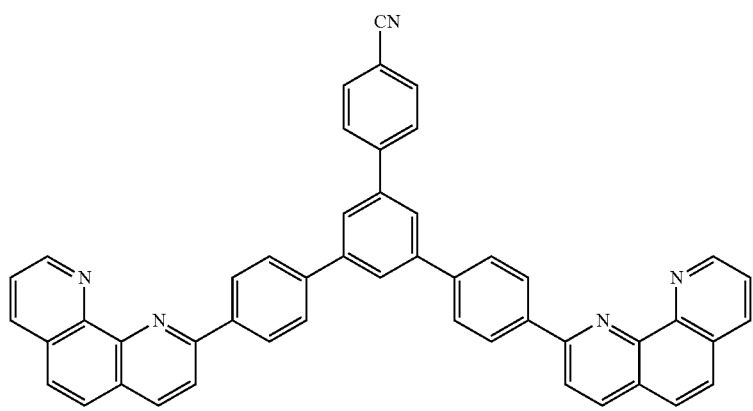

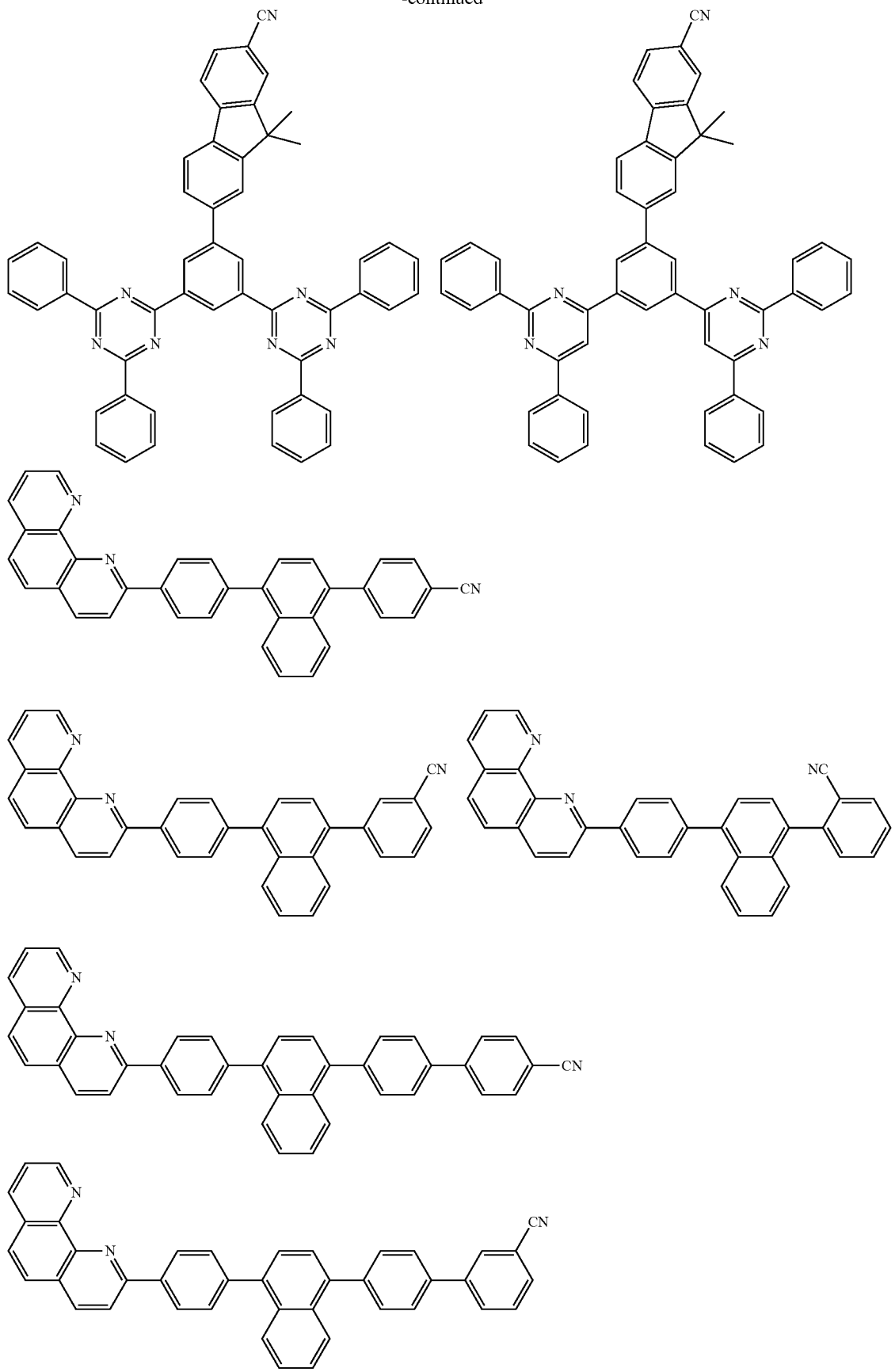

-continued
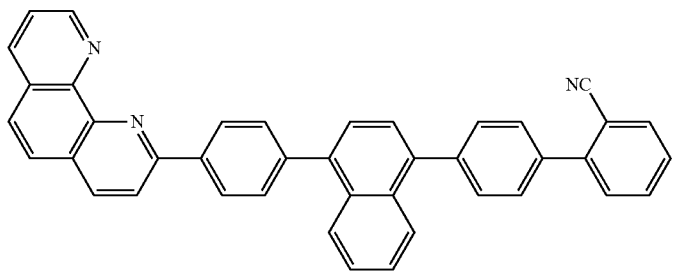
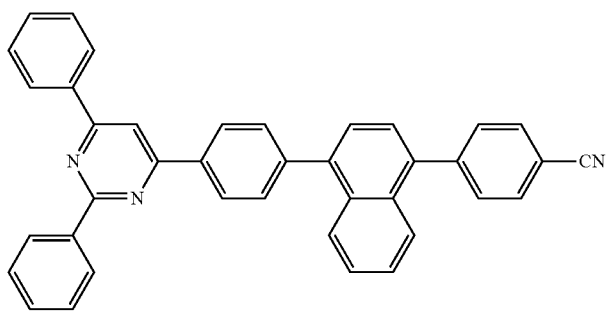
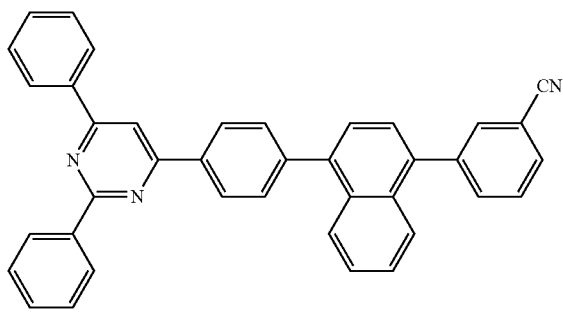
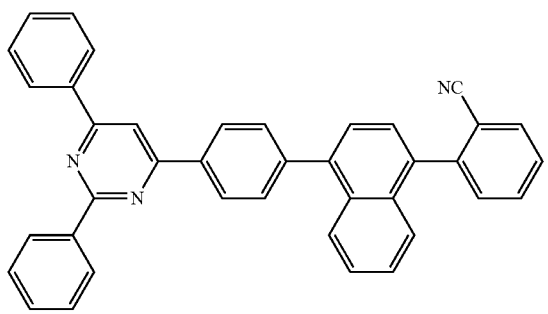
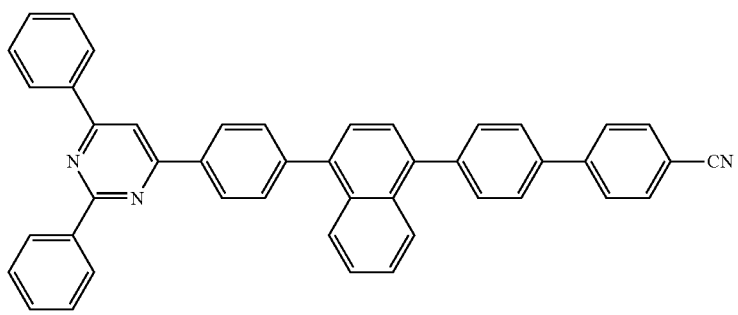

-continued
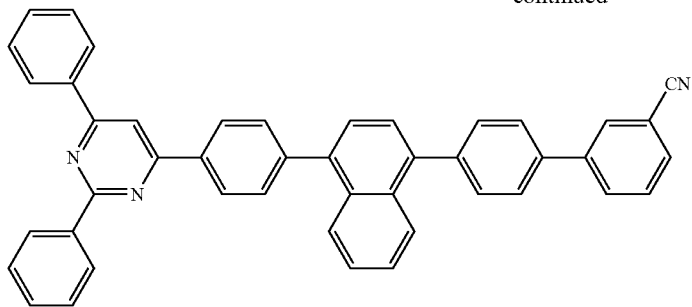
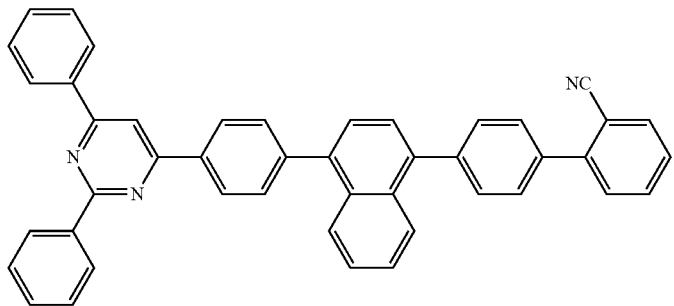
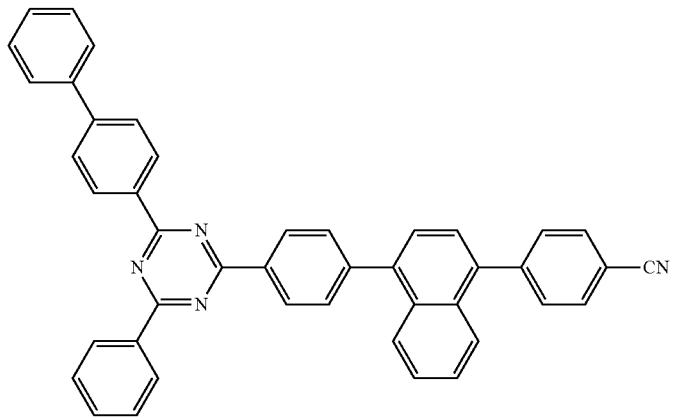
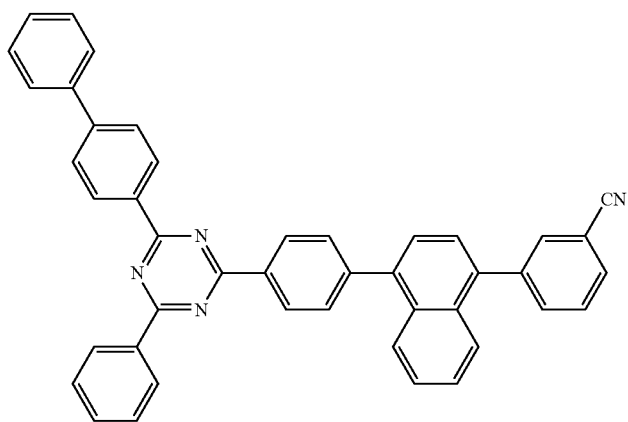

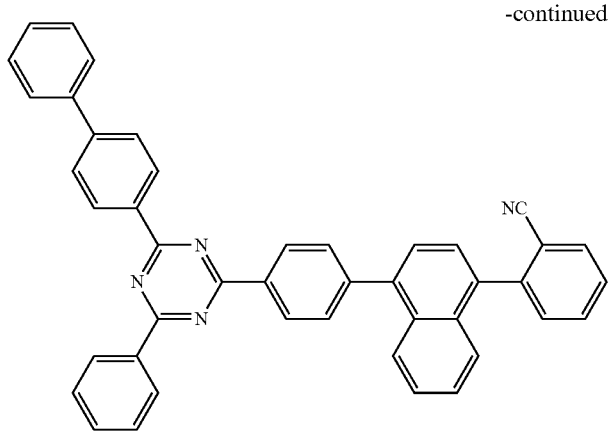
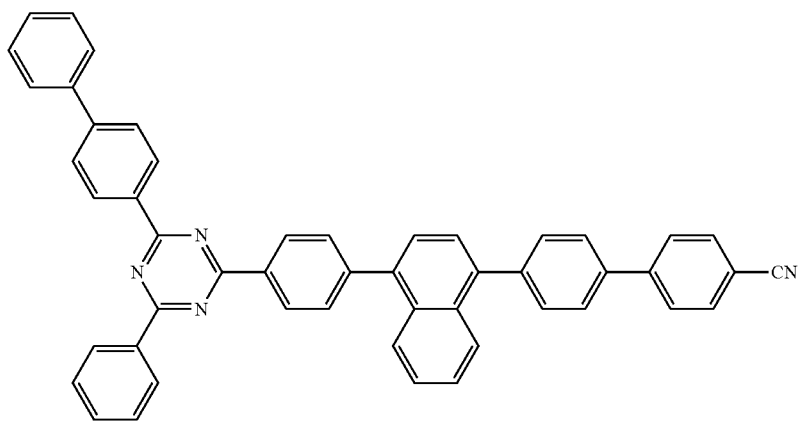
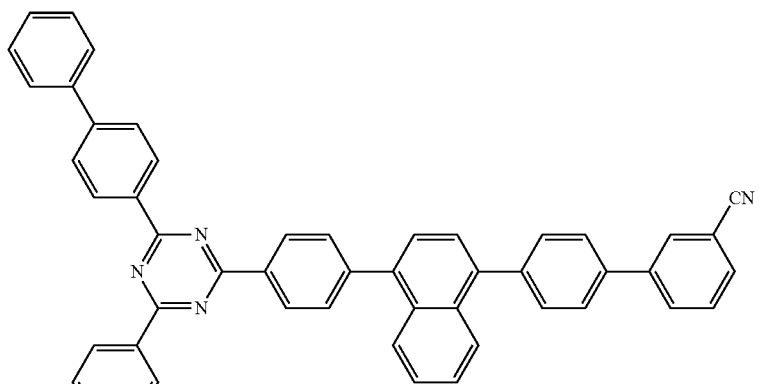
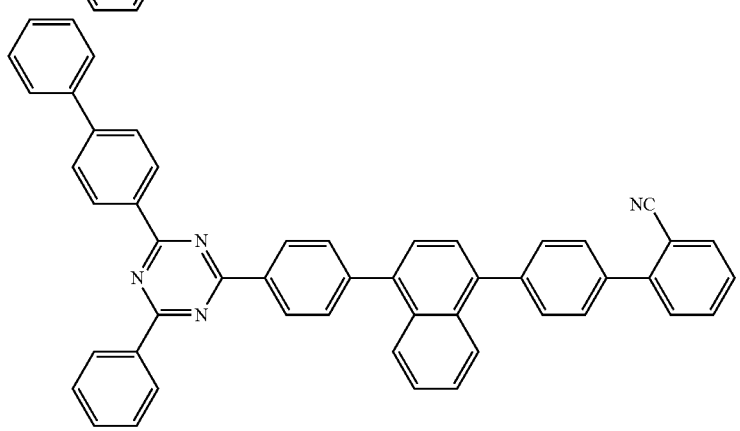

-continued
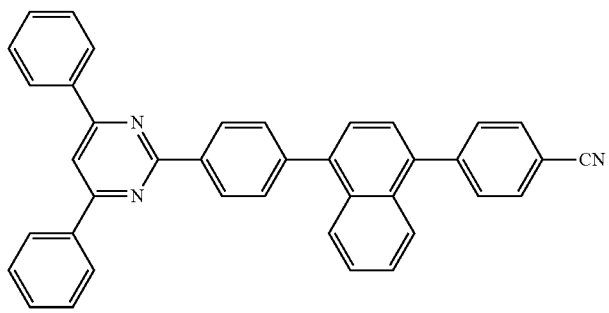
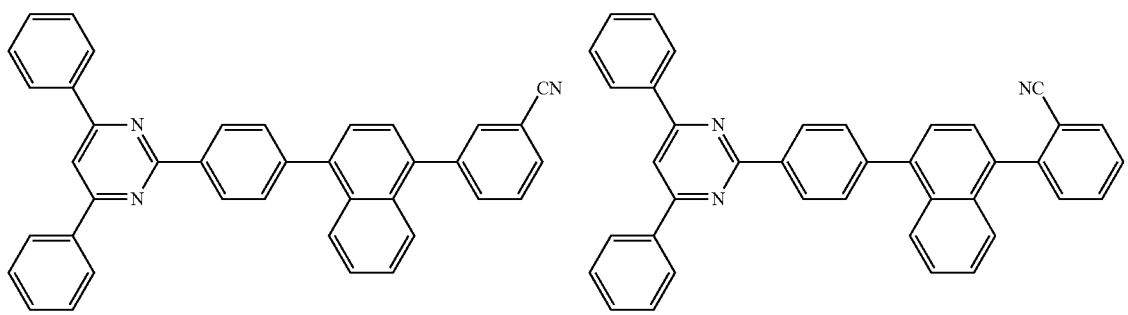
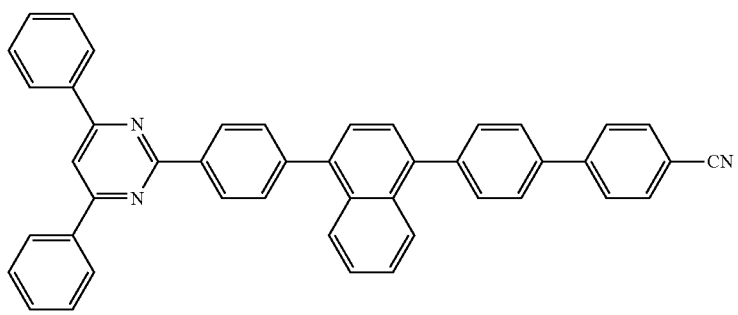
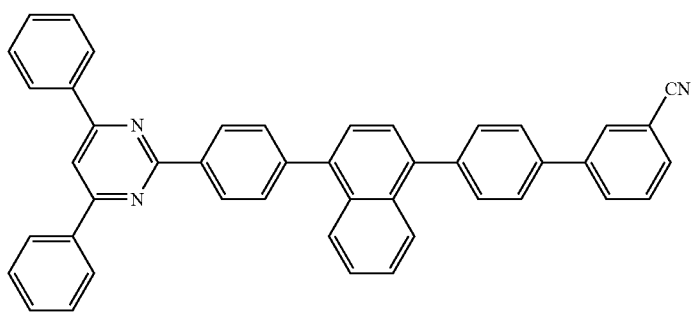
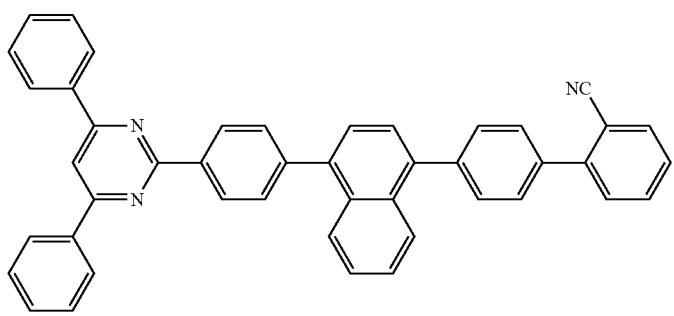

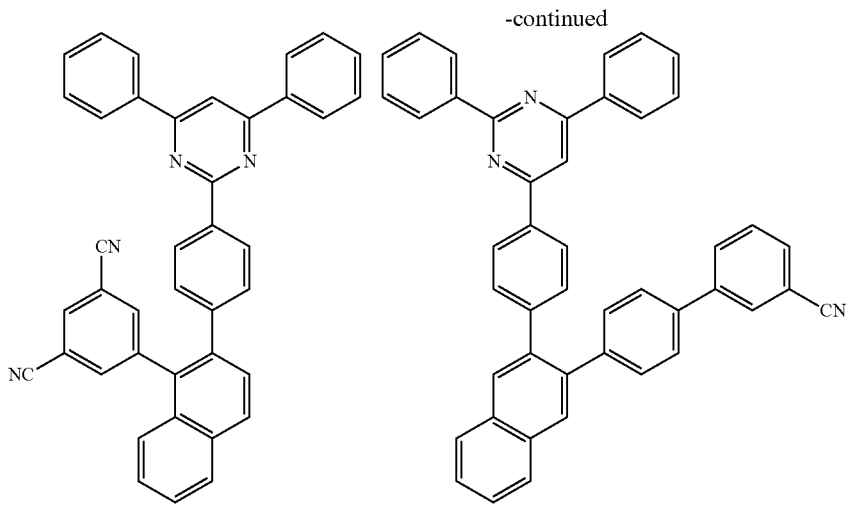

According to an exemplary embodiment of the present specification, the organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, an electron blocking layer, a light emitting layer, a hole blocking layer, an electron transporting layer, an electron injection layer, and the like as organic material layers. However, the structure of the organic light emitting device is not limited thereto, and may include fewer or more organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, a light emitting layer 40, an electron transporting layer 80, an electron injection layer 90, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes a light emitting layer, and the light emitting layer includes the compound represented by Chemical Formula 1.

According to another exemplary embodiment of the present specification, the organic material layer includes a light emitting layer, and the light emitting layer includes the compound represented by Chemical Formula 1 as a host or dopant of the light emitting layer.

According to an exemplary embodiment of the present specification, the organic material layer includes a hole blocking layer, and the hole blocking layer includes the compound represented by Chemical Formula 1.

According to an exemplary embodiment of the present specification, the organic material layer includes an electron transporting layer, an electron injection layer, or a layer which simultaneously transports and injects electrons, and the electron transporting layer, the electron injection layer, or the layer which simultaneously transports and injects electrons includes the compound represented by Chemical Formula 1.

According to an exemplary embodiment of the present specification, the organic material layer may further include one or more layers selected from the group consisting of a hole injection layer, a hole transporting layer, a light emitting layer, an electron transporting layer, and an electron injection layer.

The organic light emitting device of the present specification may be manufactured by the materials and methods known in the art, except that one or more layers of the organic material layers include the compound of the present specification, that is, the compound represented by Chemical Formula 1.

When the organic light emitting device includes a plurality of organic material layers, the organic material layer may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a second electrode, thereon. In addition to the method described above, an organic light emitting device may be made by sequentially depositing a second electrode material, an organic material layer, and a first electrode material on a substrate. Further, the compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from the hole injection layer and transports holes to the light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The electron blocking layer is a layer which may improve the service life and efficiency of the device by preventing electrons injected from an electron injection layer from passing through a light emitting layer and entering a hole injection layer, and may be formed at an appropriate portion between the light emitting layer and the hole injection layer using publicly-known materials, if necessary.

The light emitting material for the light emitting layer is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto. Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The hole blocking layer is a layer which may improve the service life and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

The electron transporting layer is a layer which receives electrons from an electron injection layer and transports the electrons to a light emitting layer, and an electron transporting material for the electron transporting layer is a material which may inject electrons well from a negative electrode and transfer the electrons to a light emitting layer, and is suitably a material which has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transporting layer may be used with any desired cathode material, as used according to the related art. In particular, examples of an appropriate cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a positive electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

In addition, the organic light emitting device according to the present specification may be a normal type in which a lower electrode is an anode and an upper electrode is a cathode, and may also be an inverted type in which a lower electrode is a cathode and an upper electrode is an anode.

According to an exemplary embodiment of the present specification, the compound represented by Chemical Formula 1 may be included in an organic solar cell or an organic transistor in addition to the organic light emitting device.

Hereinafter, the present specification will be described in detail with reference to the Examples for specifically describing the present specification. However, the Examples according to the present specification may be modified in various forms, and it is not interpreted that the scope of the present specification is limited to the Examples described below in detail. The Examples of the present specification are provided for more completely explaining the present specification to the person with ordinary skill in the art.

Preparation Example 1. Preparation of Compound 2-1-1

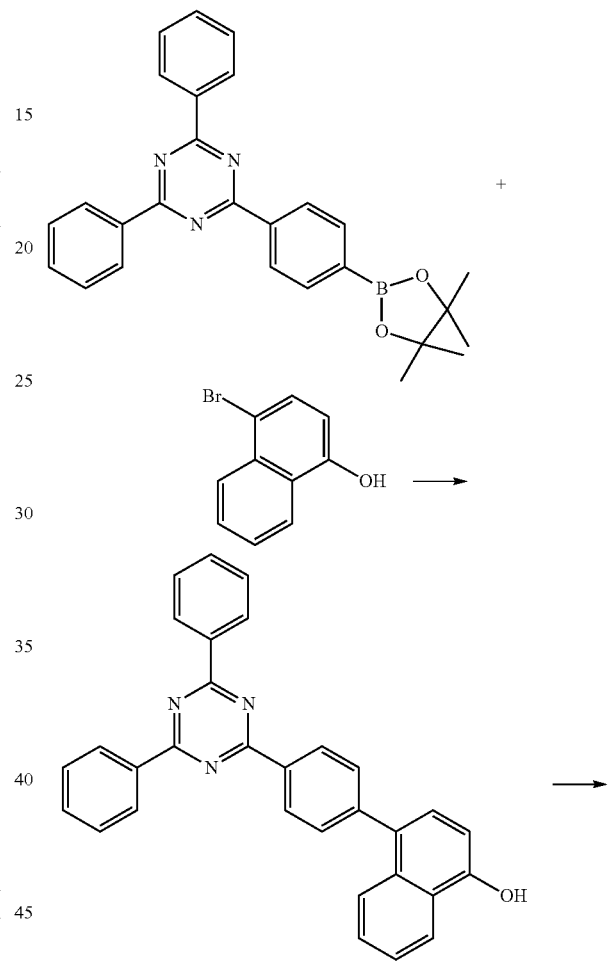

[Compound 1A]

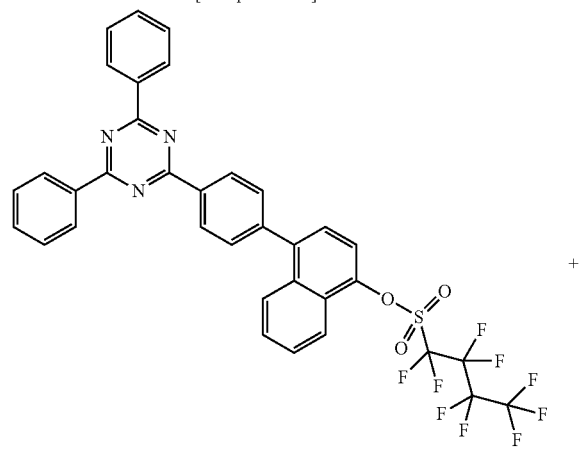

[Compound 1B]

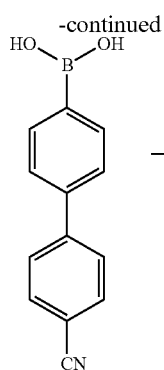

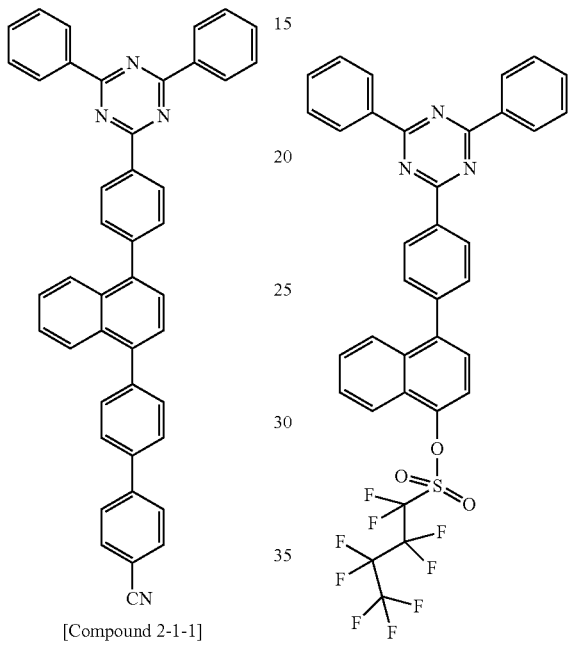

[Compound 2-1-1]

1) Preparation of Compound 1A

Triazine boronic acid (20 g, 45.9 mmol), 1-bromo-4-naphthol (10.2 g, 45.9 mol), and potassium carbonate ($K_2CO_3$)(19 g, 138 mmol) were dissolved in tetrahydrofuran (THF) (500 mL) and $H_2O$ (150 ml), and the resulting solution was heated to 90° C. Tetrakis(triphenylphosphine) palladium ($Pd(PPh_3)_4$) (1.06 g, 0.92 mmol) was added thereto, and then the resulting mixture was refluxed for 4 hours. The mixture was cooled to room temperature, and then the aqueous layer was removed. Magnesium sulfate ($MgSO_4$) was put into the organic layer, and then the resulting product was filtered. The filtrate was concentrated, and then purified by column chromatography to obtain Compound 1A (20 g, yield 97%).

MS: $[M+H]^+=451$

2) Preparation of Compound 1B

Compound 1A (20 g, 44.3 mmol), perfluorobutanesulfonic acid (53 mmol), and potassium carbonate ($K_2CO_3$) (18 g, 133 mmol) were dissolved in acetonitrile (500 mL), and the resulting solution was heated to 50° C., and then refluxed for 4 hours. The resulting product was cooled to room temperature, and then water was introduced thereinto and potassium carbonate was removed to obtain Compound 1B (26 g, yield 76%).

MS: $[M+H]^+=733$

3) Preparation of Compound 2-1-1

Compound 1B (26 g, 35.4 mmol), 4-cyanobiphenylboronic acid (7.9 g, 35.4 mmol), and potassium carbonate ($K_2CO_3$) (14.7 g, 106 mmol) were dissolved in tetrahydrofuran (THF) (500 mL) and $H_2O$ (150 ml), and the resulting solution was heated to 90° C. Tetrakis(triphenylphosphine) palladium ($Pd(PPh_3)_4$) (0.8 g, 0.71 mmol) was added thereto, and then the resulting mixture was refluxed for 4 hours. The mixture was cooled to room temperature, and then the aqueous layer was removed. Magnesium sulfate ($MgSO_4$) was put into the organic layer, and then the resulting product was filtered. The filtrate was concentrated, and then purified by column chromatography to obtain Compound 2-1-1 (16 g, yield 74%).

MS: $[M+H]^+=612$

Preparation Example 2. Preparation of Compound 2-1-2

[Compound 2-1-2]

Compound 2-1-2 (15 g, yield 79%) was obtained in the same manner as in 3) Preparation of Compound 2-1-1 in Preparation Example 1, except that 3-cyanophenylboronic acid was used instead of 4-cyanobiphenylboronic acid.

MS: $[M+H]+=536$

Preparation Example 3. Preparation of Compound 2-1-3

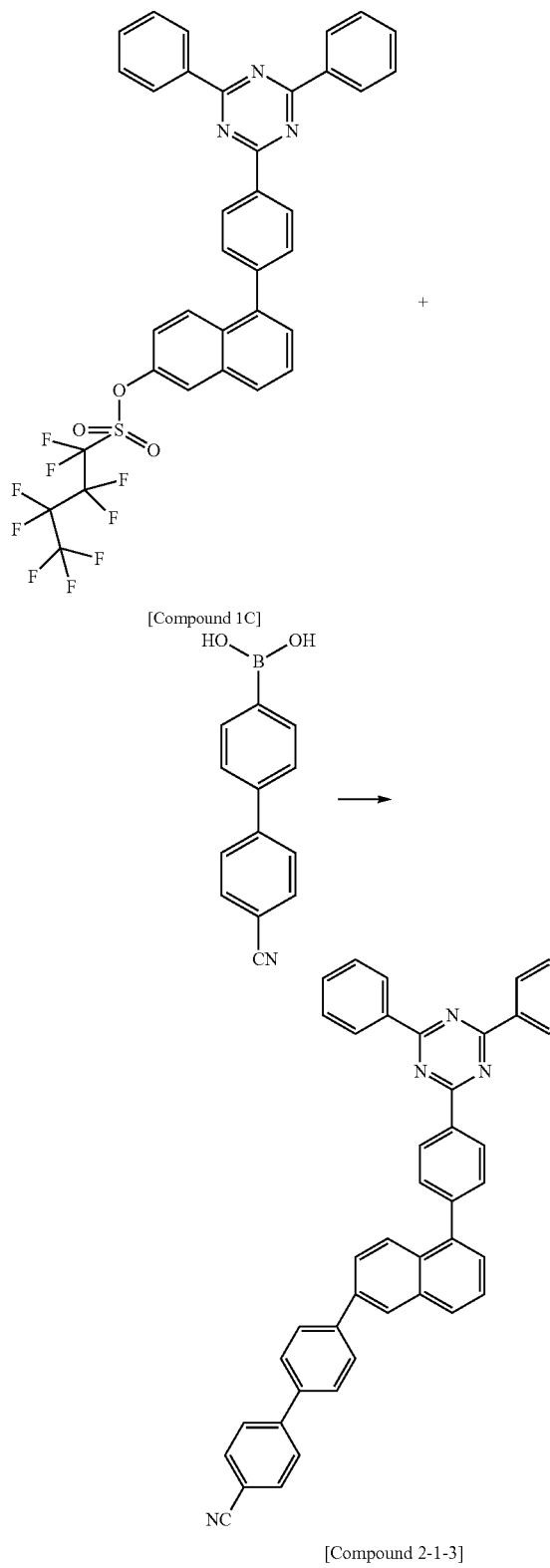

Compound 2-1-3 (17 g, yield 78%) was obtained in the same manner as in 3) Preparation of Compound 2-1-1 in Preparation Example 1, except that Compound 1C was used instead of Compound 1B.

MS: $[M+H]^+$=612

Preparation Example 4. Preparation of Compound 2-1-4

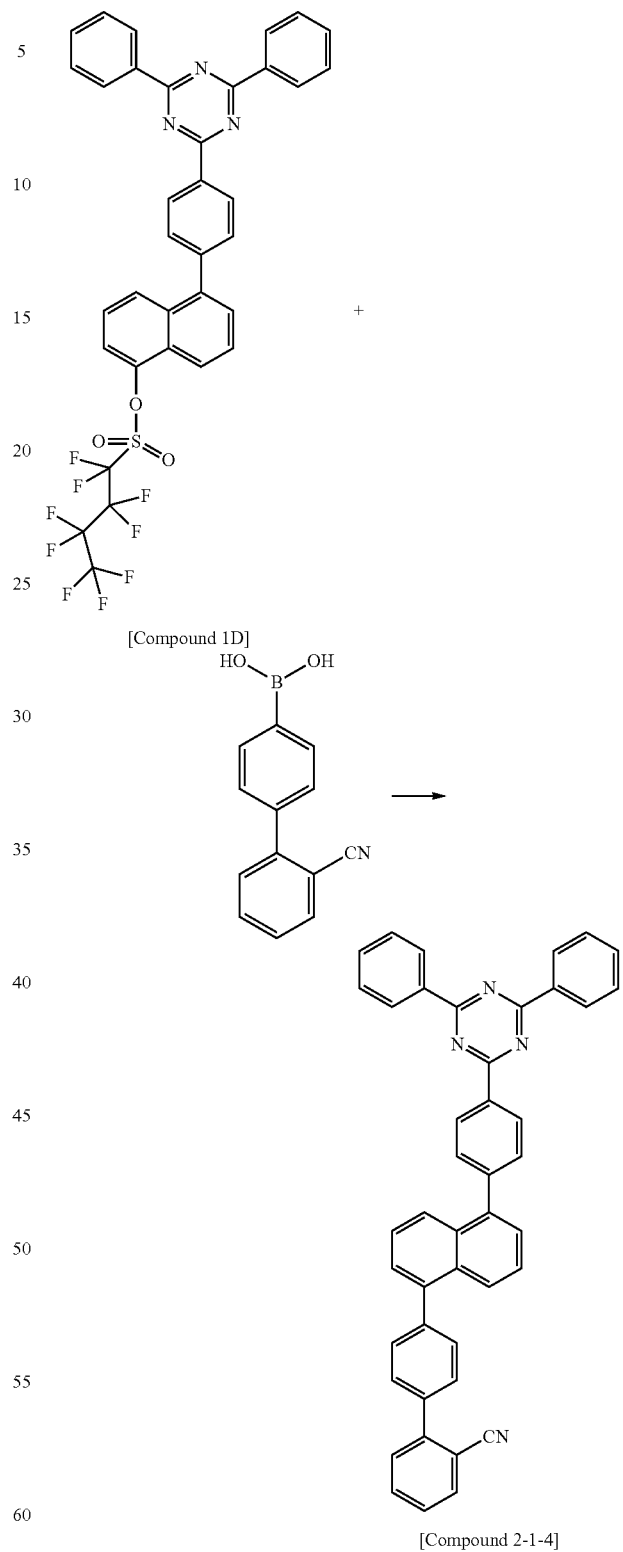

Compound 2-1-4 (19 g, yield 88%) was obtained in the same manner as in 3) Preparation of Compound 2-1-1 in Preparation Example 1, except that Compound 1D and 2-cyanobiphenyboronic acid were used instead of Compound 1B and 4-cyanobiphenylboronic acid.

MS: $[M+H]^+$=612

Preparation Example 5. Preparation of Compound 2-1-5

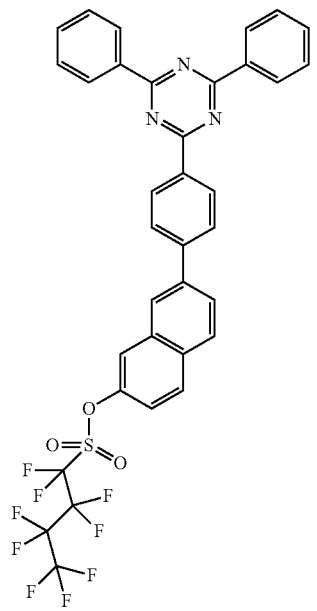

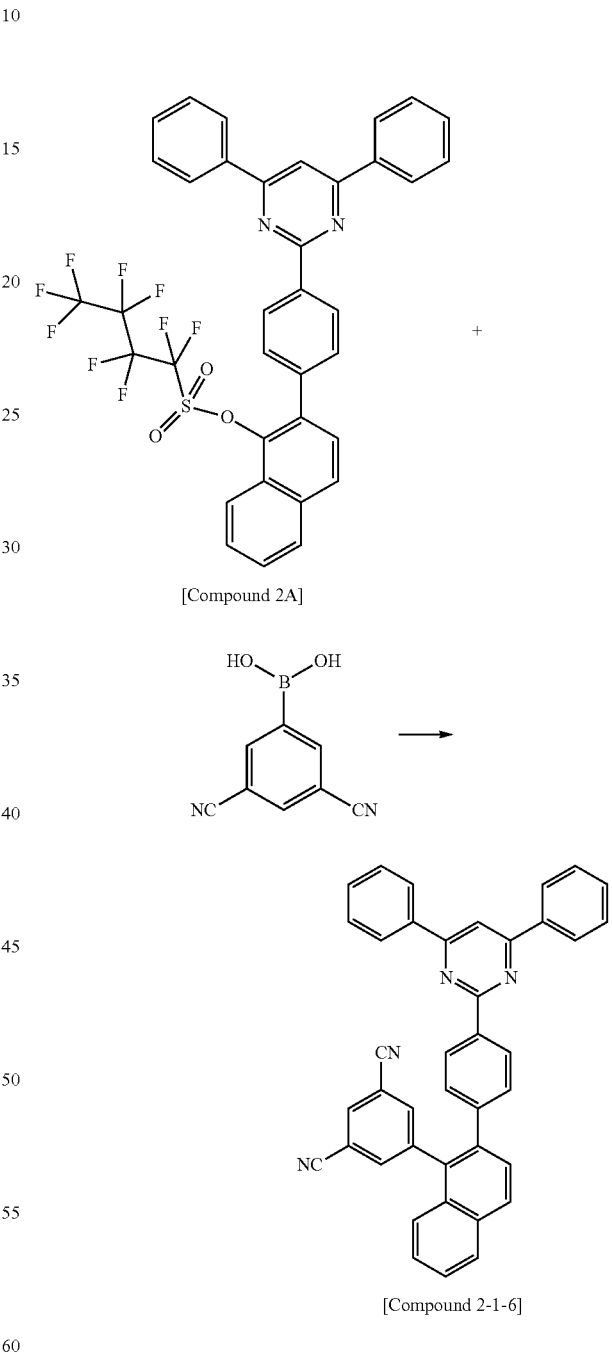

Compound 2-1-5 (14 g, yield 65%) was obtained in the same manner as in 3) Preparation of Compound 2-1-1 in Preparation Example 1, except that Compound 1E was used instead of Compound 1B.

MS: $[M+H]^+=612$

Preparation Example 6. Preparation of Compound 2-1-6

Compound 2-1-6 (15 g, yield 75%) was obtained in the same manner as in 3) Preparation of Compound 2-1-1 in Preparation Example 1, except that Compound 2A and 3,3-dicyanophenylboronic acid were used instead of Compound 1B and 4-cyanobiphenylboronic acid.

MS: $[M+H]^+=561$

Preparation Example 7. Preparation of Compound 2-1-7

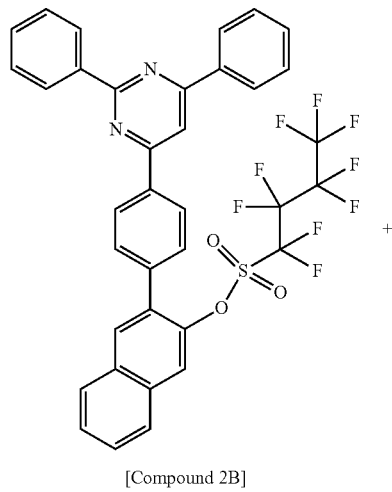

[Compound 2B]

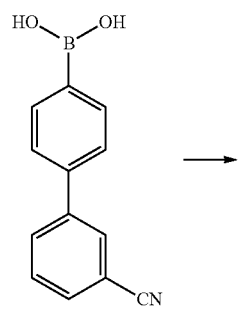

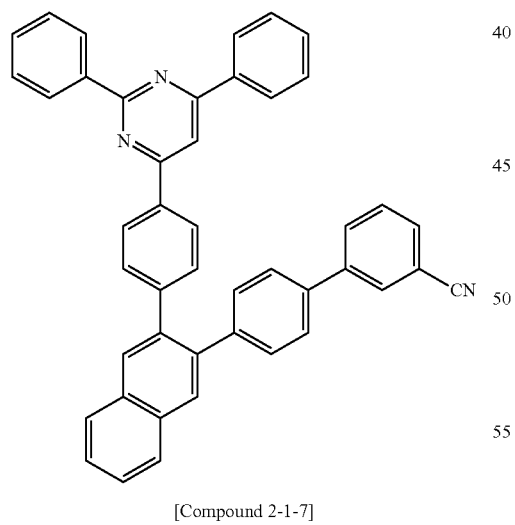

[Compound 2-1-7]

Compound 2-1-7 (14 g, yield 65%) was obtained in the same manner as in 3) Preparation of Compound 2-1-1 in Preparation Example 1, except that Compound 2B and 3-dicyanophenylboronic acid were used instead of Compound 1B and 4-cyanobiphenylboronic acid.

MS: $[M+H]^+$=611

Preparation Example 8. Preparation of Compound 2-2-1

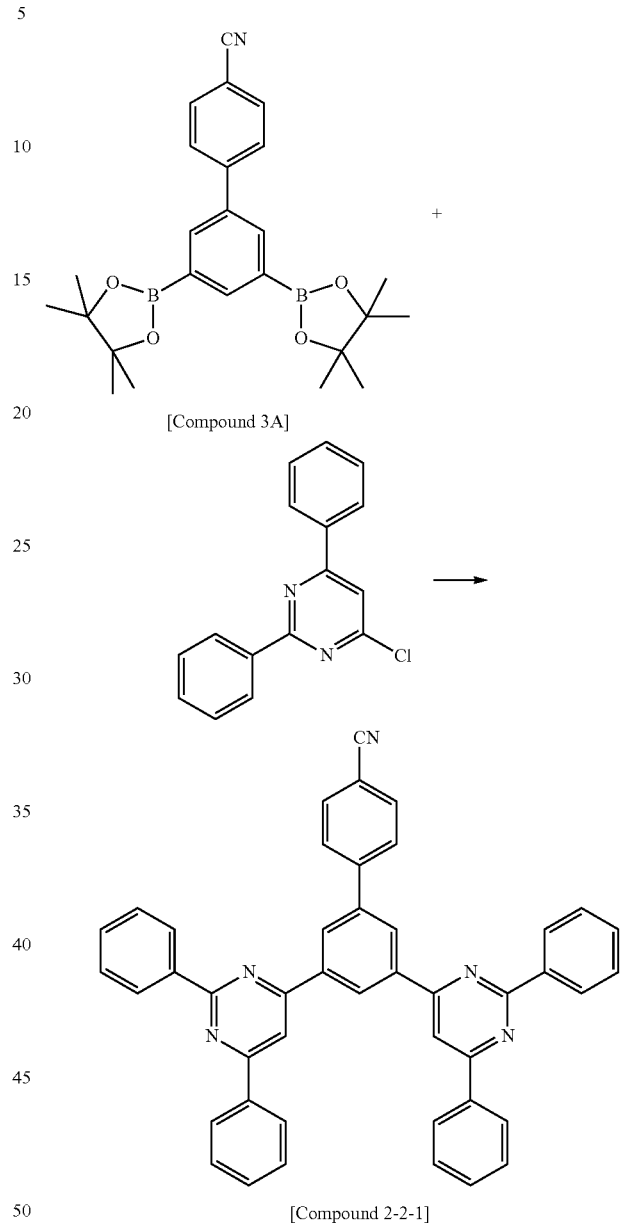

Compound 3A (15 g, 34.8 mmol), diphenylpyrimidine (18.5 g, 69.6 mmol), and potassium carbonate ($K_2CO_3$) (28.7 g, 208 mmol) were dissolved in tetrahydrofuran (THF) (500 mL) and $H_2O$ (150 ml), and the resulting solution was heated to 90° C. Tetrakis(triphenylphosphine) palladium ($Pd(PPh_3)_4$) (1.6 g, 1.4 mmol) was added thereto, and then the resulting mixture was refluxed for 12 hours. The mixture was cooled to room temperature, and then the aqueous layer was removed. Magnesium sulfate ($MgSO_4$) was put into the organic layer, and then the resulting product was filtered. The filtrate was concentrated, and then purified by column chromatography to obtain Compound 2-2-1 (20 g, yield 90%).

MS: $[M+H]^+$=639

Preparation Example 9. Preparation of Compound 2-2-2

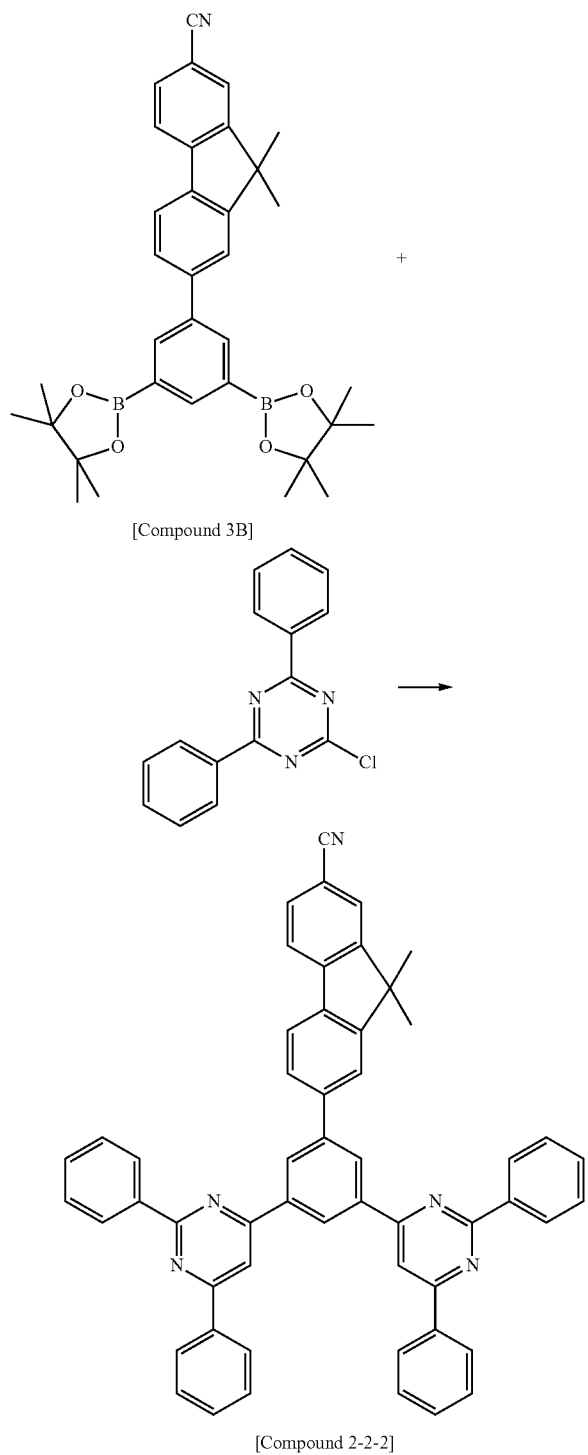

[Compound 3B]

[Compound 2-2-2]

Compound 3B (10 g, 18.3 mmol), diphenyltriazine (9.8 g, 36.6 mmol), and potassium carbonate ($K_2CO_3$) (15.2 g, 109 mmol) were dissolved in tetrahydrofuran (THF) (400 mL) and $H_2O$ (100 ml), and the resulting solution was heated to 90° C. Tetrakis(triphenylphosphine) palladium ($Pd(PPh_3)_4$) (0.85 g, 0.73 mmol) was added thereto, and then the resulting mixture was refluxed for 8 hours. The mixture was cooled to room temperature, and then the aqueous layer was removed. Magnesium sulfate ($MgSO_4$) was put into the organic layer, and then the resulting product was filtered. The filtrate was concentrated, and then purified by column chromatography to obtain Compound 2-2-2 (10 g, yield 72%).

MS: $[M+H]^+$=755

Preparation Example 10. Preparation of Compound 3-2-1

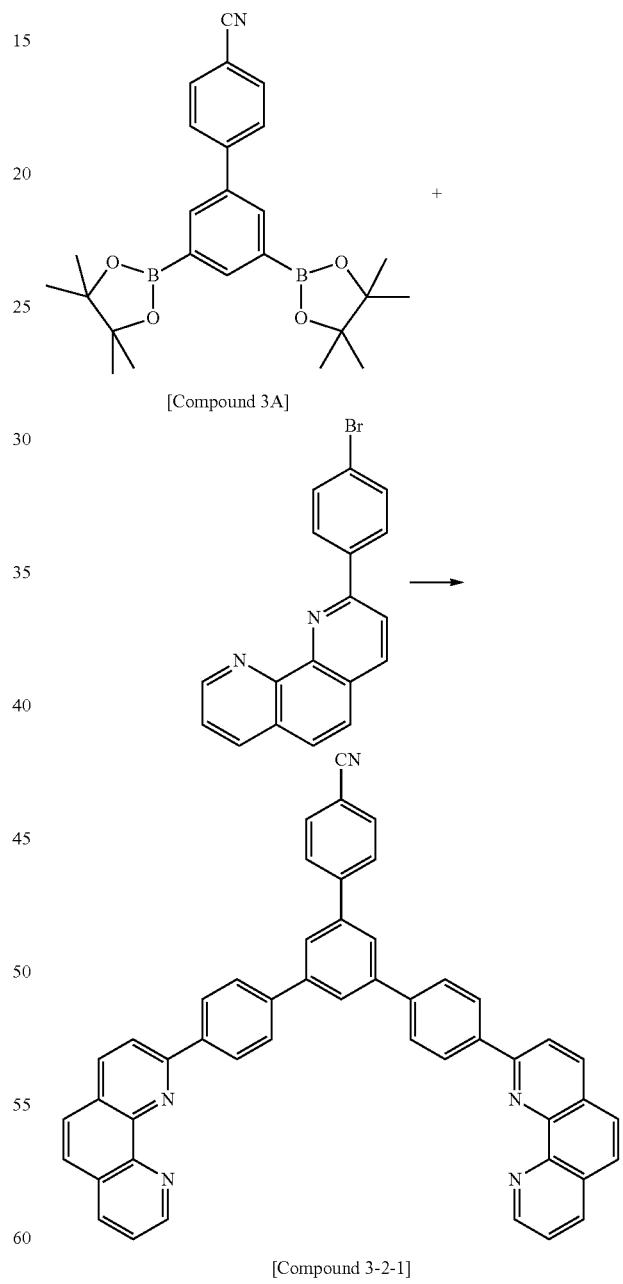

[Compound 3A]

[Compound 3-2-1]

Compound 3-2-1 (21 g, yield 87%) was obtained in the same manner as in Preparation Example 8, except that 2-bromophenyl phenanthroline was used instead of diphenylpyrimidine.

MS: $[M+H]^+$=687

Example 1

A glass substrate (Corning 7059 glass) thinly coated with ITO (indium tin oxide) to have a thickness of 1000 Å was put into distilled water in which a dispersant was dissolved, and ultrasonically washed. A product manufactured by Fischer Co. was used as the detergent, and distilled water twice filtered using a filter manufactured by Millipore Co. was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å by heating on a transparent ITO electrode, which was thus prepared, thereby forming a hole injection layer. HT1 (400 Å), which is a material transporting holes, was vacuum deposited thereon, and then the host H1 compound and the dopant D1 compound were vacuum deposited as a light emitting layer to have a thickness of 300 Å. Compound 2-1-1 prepared in Preparation Example 1 and LiQ (lithium quinolate) were vacuum deposited at a weight ratio of 1:1 on the light emitting layer, thereby forming an electron injection and transporting layer having a thickness of 350 Å. Lithium fluoride (LiF) and aluminum were sequentially deposited to have a thickness of 12 Å and 2,000 Å, respectively, on the electron injection and transporting layer, thereby forming a negative electrode. An organic light emitting device was manufactured.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

[Hexanitrile hexaazatriphenylene] [LiQ]

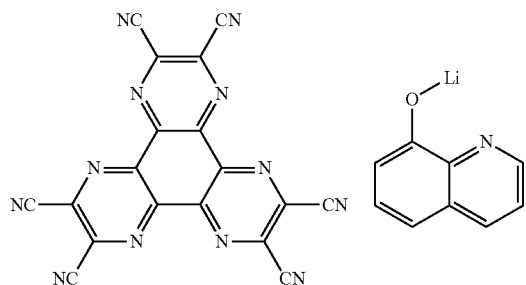

[HT1]

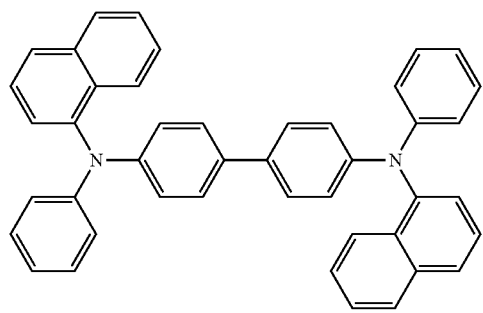

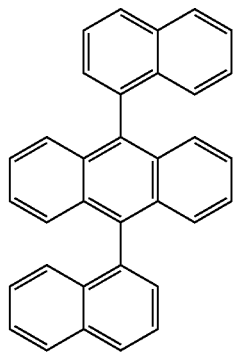

[H1]

[D1]

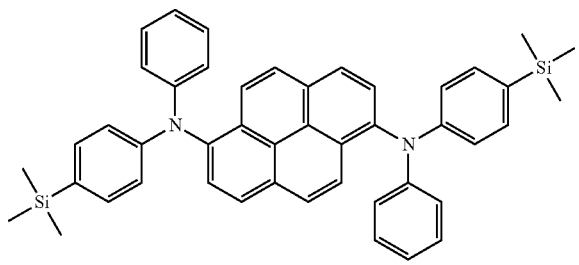

Example 2

An experiment was performed in the same manner as in Example 1, except that Compound 2-1-2 was used instead of Compound 2-1-1 as the electron transporting layer.

Example 3

An experiment was performed in the same manner as in Example 1, except that Compound 2-1-3 was used instead of Compound 2-1-1 as the electron transporting layer.

Example 4

An experiment was performed in the same manner as in Example 1, except that Compound 2-1-4 was used instead of Compound 2-1-1 as the electron transporting layer.

Example 5

An experiment was performed in the same manner as in Example 1, except that Compound 2-1-5 was used instead of Compound 2-1-1 as the electron transporting layer.

Example 6

An experiment was performed in the same manner as in Example 1, except that Compound 2-1-6 was used instead of Compound 2-1-1 as the electron transporting layer.

Example 7

An experiment was performed in the same manner as in Example 1, except that Compound 2-1-7 was used instead of Compound 2-1-1 as the electron transporting layer.

Example 8

An experiment was performed in the same manner as in Example 1, except that Compound 2-2-1 was used instead of Compound 2-1-1 as the electron transporting layer.

Example 9

An experiment was performed in the same manner as in Example 1, except that Compound 2-2-2 was used instead of Compound 2-1-1 as the electron transporting layer.

Example 10

An experiment was performed in the same manner as in Example 1, except that Compound 3-2-1 was used instead of Compound 2-1-1 as the electron transporting layer.

Comparative Example 1

An experiment was performed in the same manner as in Example 1, except that the following Compound ET1 was used instead of Compound 2-1-1 as the electron transporting layer.

[ET1]

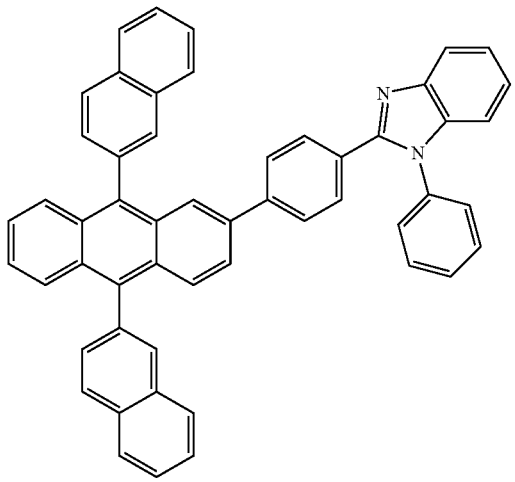

Comparative Example 2

An experiment was performed in the same manner as in Example 1, except that the following Compound ET2 was used instead of Compound 2-1-1 as the electron transporting layer.

[ET2]

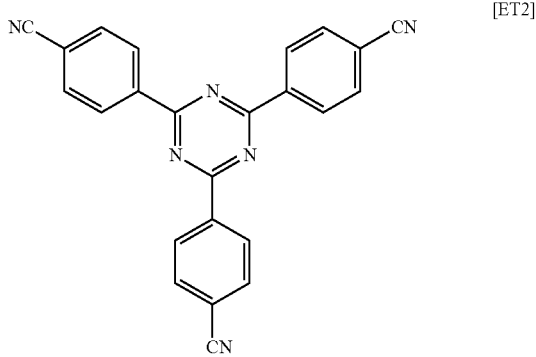 [SMILES: N#Cc1ccc(-c2nc(-c3ccc(C#N)cc3)nc(-c3ccc(C#N)cc3)n2)cc1]

Comparative Example 3

An experiment was performed in the same manner as in Example 1, except that the following Compound ET3 was used instead of Compound 2-1-1 as the electron transporting layer.

[ET3]

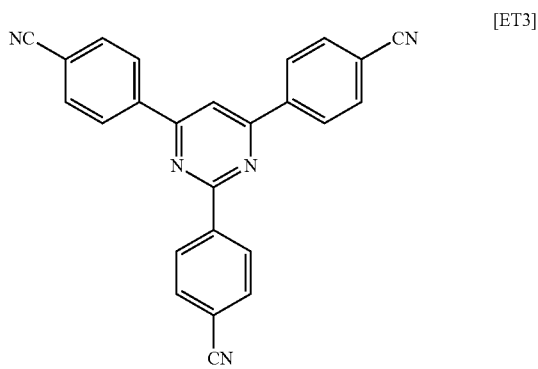 [SMILES: N#Cc1ccc(-c2cc(-c3ccc(C#N)cc3)nc(-c3ccc(C#N)cc3)n2)cc1]

For the organic light emitting devices of Examples 1 to 10 and Comparative Examples 1 to 3, the driving voltage and the light emitting efficiency were measured at a current density of 10 mA/cm$^2$, and a time (LT98) for reaching a 98% value compared to the initial luminance was measured at a current density of 20 mA/cm$^2$. The results are shown in the following Table 1.

TABLE 1

| Example 10 mA/cm$^2$ | Compound | Voltage (V) | Current efficiency (cd/A) | Color coordinate (x, y) | Life Time 98 at 20 mA/cm$^2$ |
|---|---|---|---|---|---|
| Example 1 | Compound 2-1-1 | 3.84 | 5.28 | (0.137, 0.126) | 44 |
| Example 2 | Compound 2-1-2 | 3.75 | 5.33 | (0.139, 0.127) | 46 |
| Example 3 | Compound 2-1-3 | 3.77 | 5.47 | (0.138, 0.126) | 41 |
| Example 4 | Compound 2-1-4 | 3.75 | 5.35 | (0.138, 0.129) | 42 |
| Example 5 | Compound 2-1-5 | 3.81 | 5.45 | (0.137, 0.126) | 44 |
| Example 6 | Compound 2-1-6 | 3.88 | 5.30 | (0.137, 0.124) | 41 |
| Example 7 | Compound 2-1-7 | 3.88 | 5.24 | (0.137, 0.126) | 38 |
| Example 8 | Compound 2-2-1 | 4.03 | 5.55 | (0.137, 0.126) | 49 |
| Example 9 | Compound 2-2-2 | 4.05 | 5.22 | (0.137, 0.126) | 50 |
| Example 10 | Compound 3-2-1 | 3.98 | 5.32 | (0.137, 0.126) | 48 |
| Comparative Example 1 | ET1 | 4.15 | 4.88 | (0.140, 0.129) | 25 |
| Comparative Example 2 | ET2 | 4.10 | 4.15 | (0.140, 0.129) | 12 |
| Comparative Example 3 | ET3 | 4.07 | 4.42 | (0.139, 0.129) | 10 |

In Table 1, it could be seen that the compounds in Examples 1 to 10 where the compound of Chemical Formula 1 according to an exemplary embodiment of the present specification was used as an electron transporting layer of an organic light emitting device had low driving voltage, high current efficiency, and a long service life compared to the compounds in Comparative Examples 1 to 3. In particular, it could be seen that Examples 1 to 10 where the light emitting device was manufactured by a compound in which HAr and a nitrile group in Chemical Formula 1 according to an exemplary embodiment of the present specification were linked by L1, L2, and Ar1 had low driving voltage, high current efficiency, and a long service life compared to the compound in which triazine or pyrimidine was linked by only a nitrile group and a phenylene group as in ET2 and ET3 in Comparative Examples 2 and 3.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transporting layer
80: Electron transporting layer
90: Electron injection layer

The invention claimed is:

1. An organic light emitting device comprising:
a first electrode;
a second electrode provided to face the first electrode; and
one or two or more organic material layers provided between the first electrode and the second electrode,
wherein one or more layers of the organic material layers comprise a compound represented by the following Chemical Formula 1:

(HAr)$_a$[L1-Ar1-L2-(CN)$_b$]$_c$     [Chemical Formula 1]

in Chemical Formula 1,
a to c are each an integer of 1 to 3,
when a to c are each 2 or more, two or more structures in the parenthesis are the same as or different from each other,
L1 and L2 are the same as or different from each other, and are each independently a substituted or unsubstituted divalent to tetravalent aromatic ring group,
Ar1 is a direct bond; or a substituted or unsubstituted arylene group, and
HAr is a heteroaryl group represented by the following Chemical Formula A or B;

[Chemical Formula A]

[Chemical Formula B]

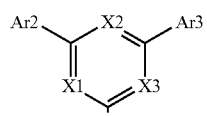

in Chemical Formulae A and B,
X1 to X3 are the same as or different from each other, and are each independently N, CH or CD,
at least two of X1 to X3 is N,
Ar2, Ar3, and R1 are the same as or different from each other, and are each independently hydrogen; or a substituted or unsubstituted aryl group, or combine with an adjacent group to form a substituted or unsubstituted ring,
n is an integer of 1 to 7,
when n is 2 or more, two or more R1's are the same as or different from each other, and
--- is a moiety linked to L1,
wherein in Chemical Formula 1, when HAr is Chemical Formula A, and b is 2, Ar1 is not a direct bond, and when HAr is Chemical Formula B, c is 1.

2. The organic light emitting device of claim 1, wherein Chemical Formula 1 is represented by the following Chemical Formula 2 or 3:

[Chemical Formula 2]

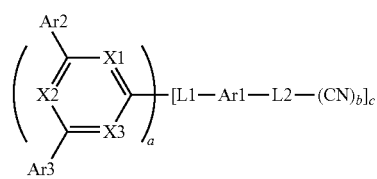

[Chemical Formula 3]

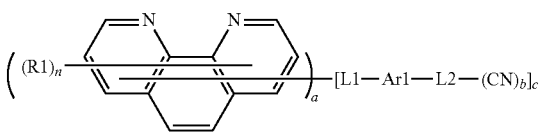

in Chemical Formulae 2 and 3,
the definitions of a, b, c, L1, L2, and Ar1 are the same as those in Chemical Formula 1,
the definitions of X1 to X3, Ar2, Ar3, R1 and n are the same as those in Chemical Formulae A and B.

3. The organic light emitting device of claim 1, wherein Chemical Formula 1 is represented by any one of the following Chemical Formulae 2-1 to 2-3:

[Chemical Formula 2-1]

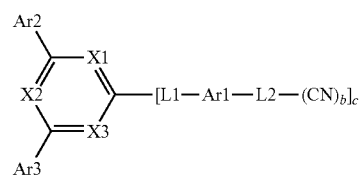

[Chemical Formula 2-2]

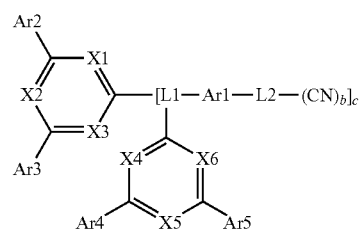

[Chemical Formula 2-3]

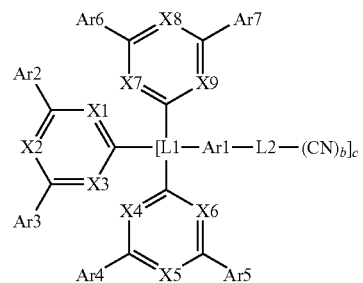

in Chemical Formulae 2-1 to 2-3,
the definitions of b, c, L1, L2, and Ar1 are the same as those in Chemical Formula 1, the definitions of X1 to X3, Ar2, and Ar3 are the same as those in Chemical Formula A, X4 to X9 are the same as or different from each other, and are each independently N, CH or CD, at least two of X4 to X6 is N, at least two of X7 to X9 is N, and Ar4 to Ar7 are the same as or different from each other, and are each independently hydrogen; or a substituted or unsubstituted aryl group, or combine with an adjacent group to form a substituted or unsubstituted ring.

4. The organic light emitting device of claim 1, wherein Chemical Formula 1 is represented by any one of the following Chemical Formulae 3-1 to 3-3:

[Chemical Formula 3-1]

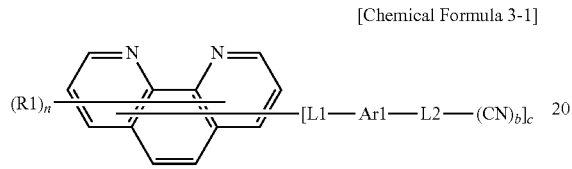

[Chemical Formula 3-2]

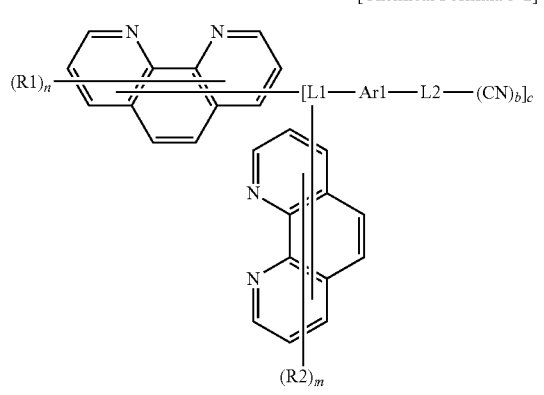

[Chemical Formula 3-3]

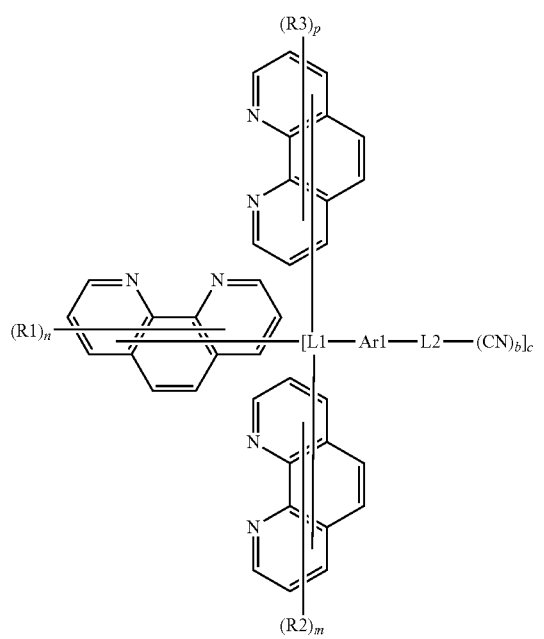

in Chemical Formulae 3-1 to 3-3, the definitions of b, c, L1, L2, and Ar1 are the same as those in Chemical Formula 1, the definitions of R1 and n are the same as those in Chemical Formula B, R2 and R3 are the same as or different from each other, and are each independently hydrogen; or a substituted or unsubstituted aryl group, or combine with an adjacent group to form a substituted or unsubstituted ring, m and p are each an integer of 1 to 7, and when m and p are each 2 or more, two or more structures in the parenthesis are the same as or different from each other.

5. The organic light emitting device of claim 1, wherein Chemical Formula A is represented by any one of the following Chemical Formulae A-4 to A-7:

[Chemical Formula A-4]

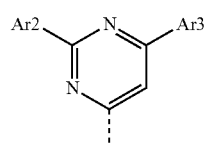

[Chemical Formula A-5]

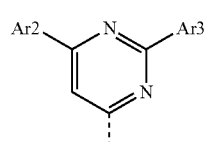

[Chemical Formula A-6]

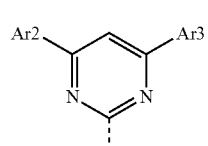

[Chemical Formula A-7]

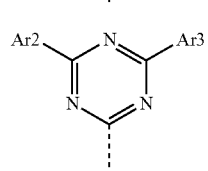

in Chemical Formulae A-4 to A-7, the definitions of Ar2 and Ar3 are the same as those in Chemical Formula A, and --- is a moiety linked to L1.

6. The organic light emitting device of claim 1, wherein Chemical Formula B is represented by any one of the following Chemical Formulae B-1 to B-4:

[Chemical Formula B-1]

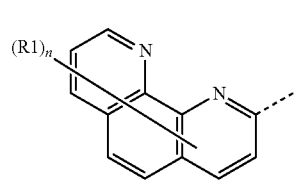

[Chemical Formula B-2]

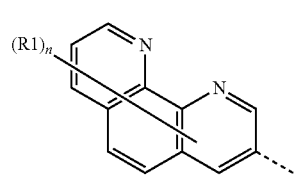

[Chemical Formula B-3]

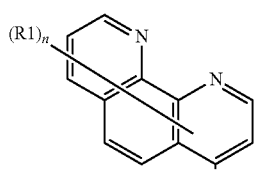

[Chemical Formula B-4]

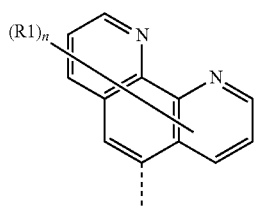

in Chemical Formulae B-1 to B-4,
the definitions of R1 and n are the same as those in Chemical Formula B, and
--- is a moiety linked to L1.

7. The organic light emitting device of claim 1, wherein L1 and L2 are the same as or different from each other, and are each independently a substituted or unsubstituted divalent to tetravalent phenyl group; a substituted or unsubstituted divalent to tetravalent biphenyl group; a substituted or unsubstituted divalent to tetravalent terphenyl group; or a substituted or unsubstituted divalent to tetravalent fluorenyl group.

8. The organic light emitting device of claim 1, wherein Ar1 is a direct bond; a substituted or unsubstituted phenylene group; a substituted or unsubstituted biphenylylene group; or a substituted or unsubstituted naphthylene group.

9. The organic light emitting device of claim 1, wherein Ar2 and Ar3 are the same as or different from each other, and are each independently a substituted or unsubstituted phenyl group; or a substituted or unsubstituted biphenyl group.

10. The organic light emitting device of claim 1, wherein Ar2 and Ar3 are the same as or different from each other, and are each independently a phenyl group; or a biphenyl group.

11. The organic light emitting device of claim 1, wherein Chemical Formula 1 is selected from any one of the following compounds

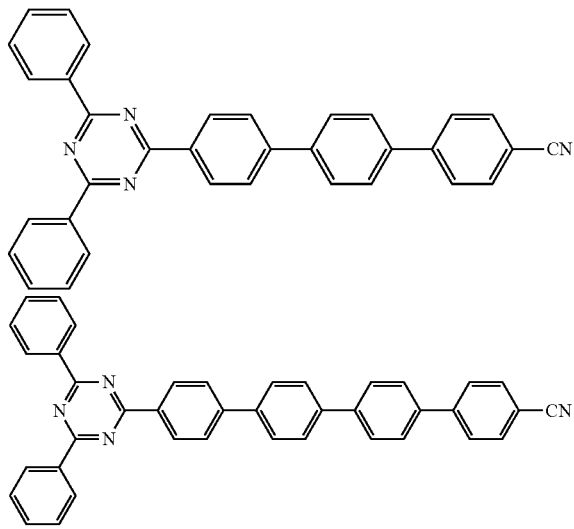

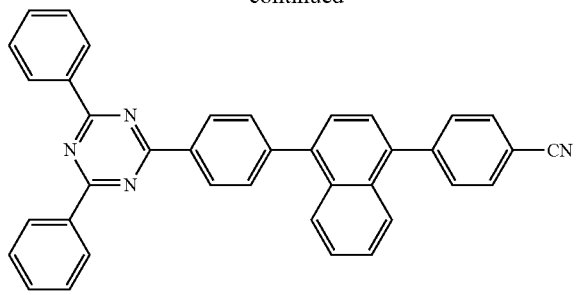

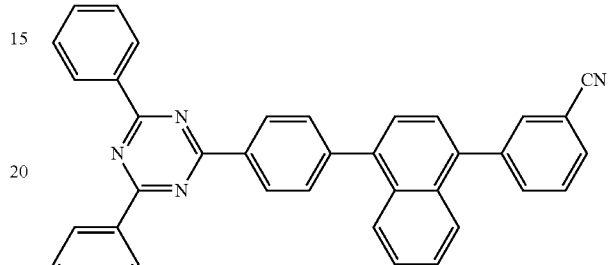

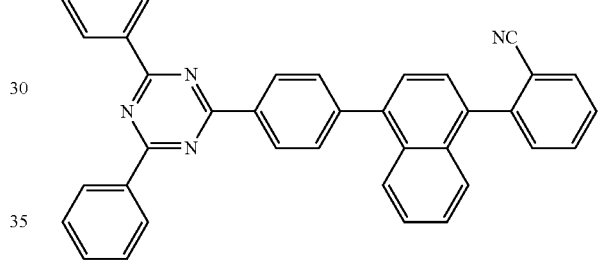

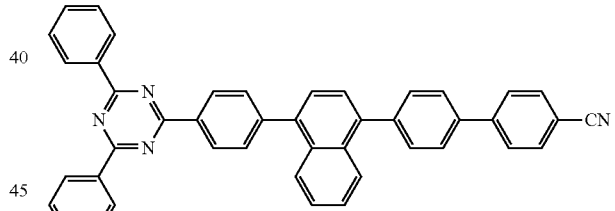

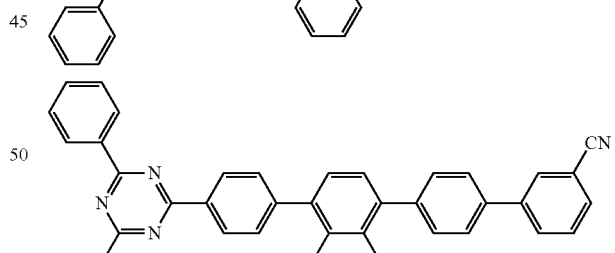

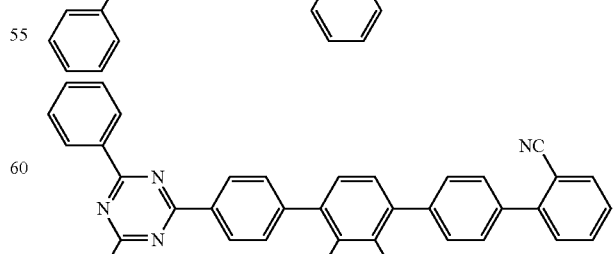

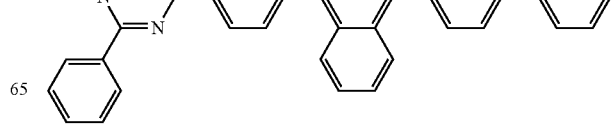

91
-continued
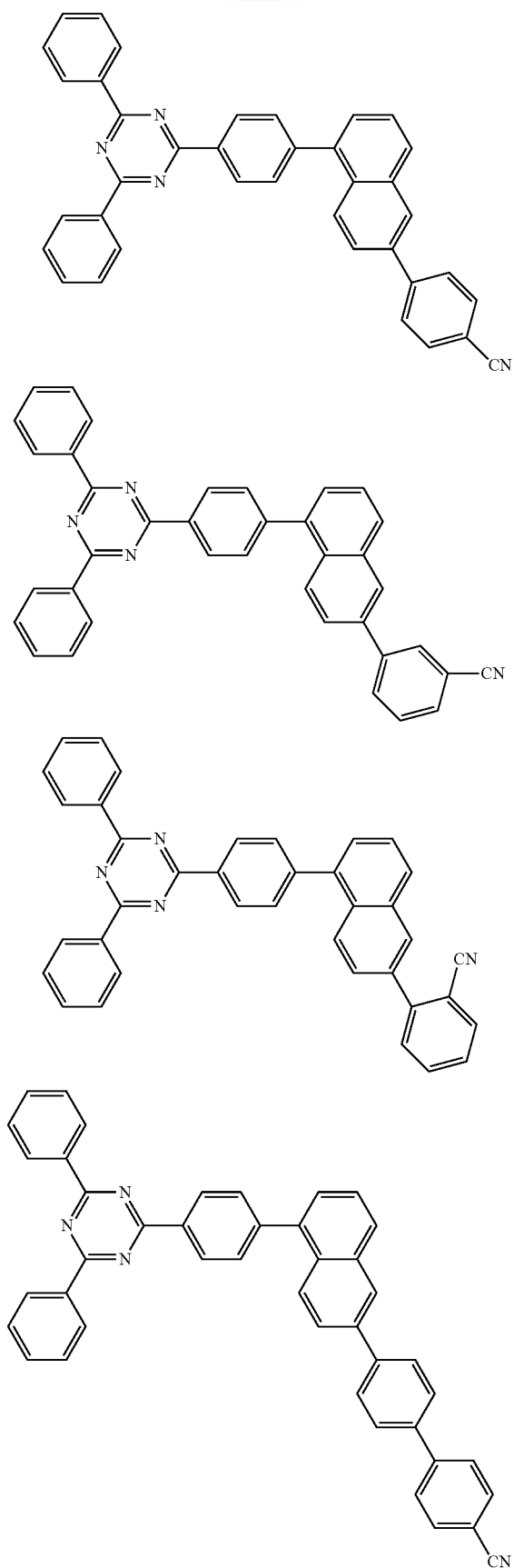
92
-continued
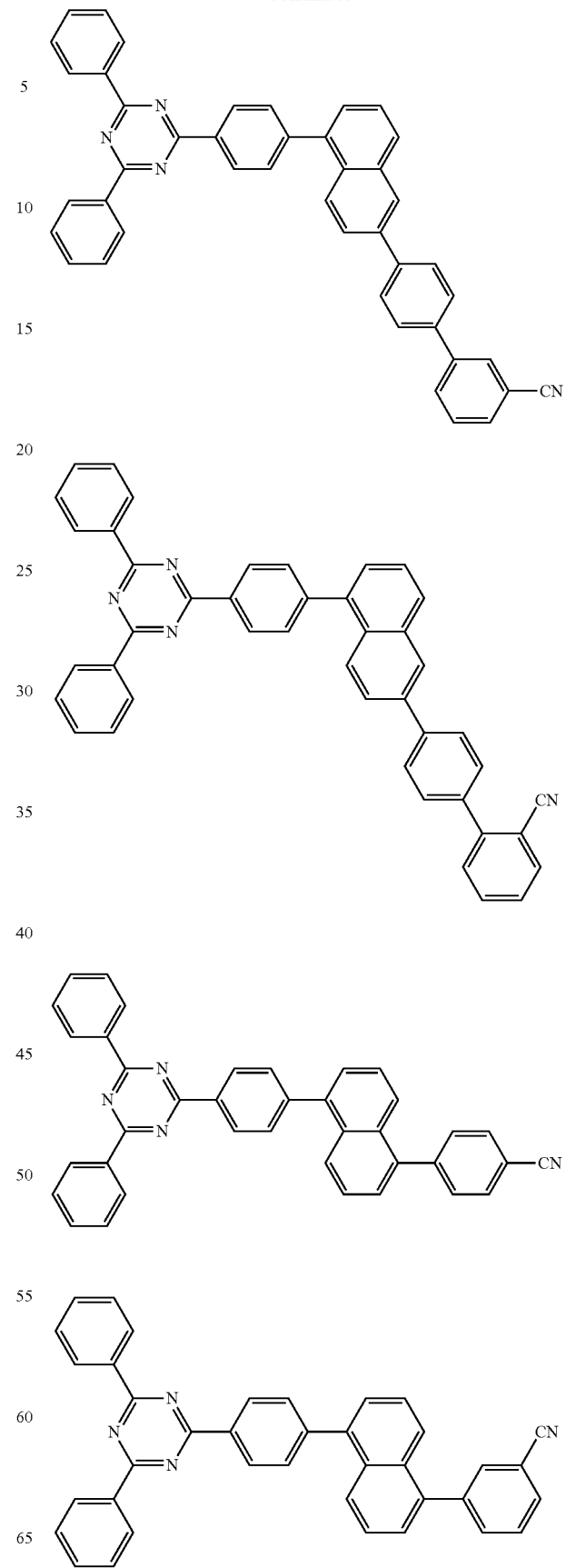

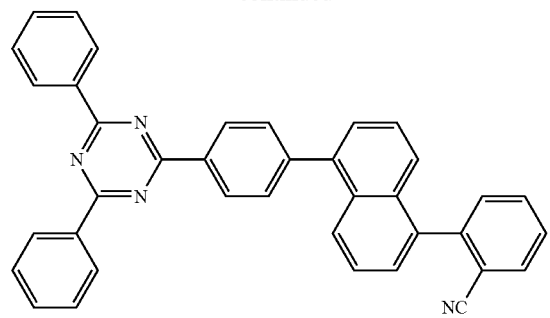
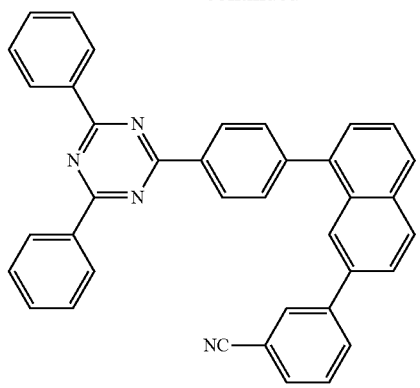
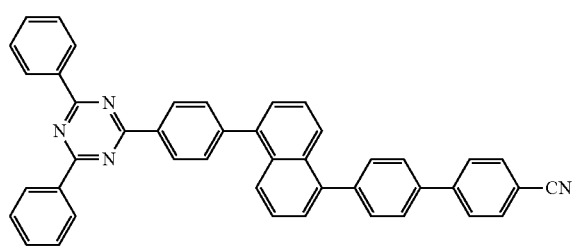
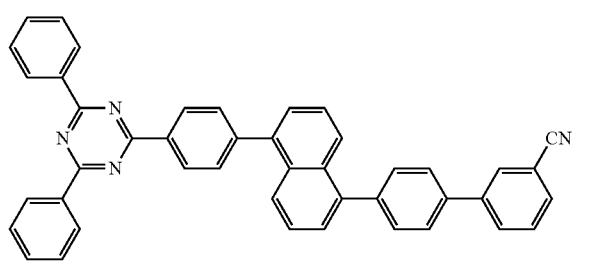
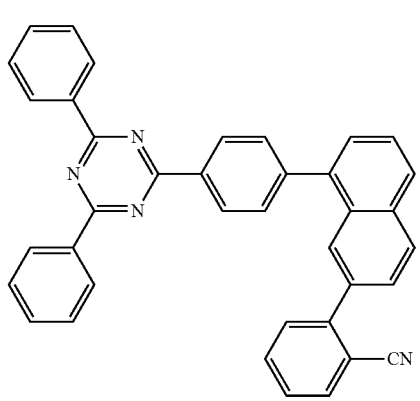
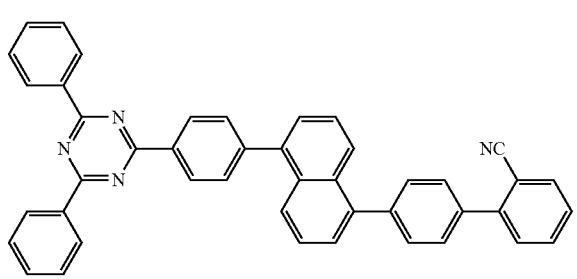
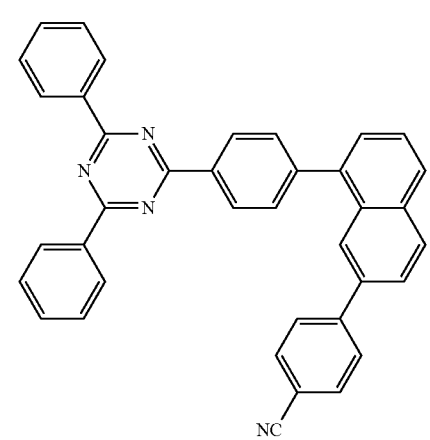
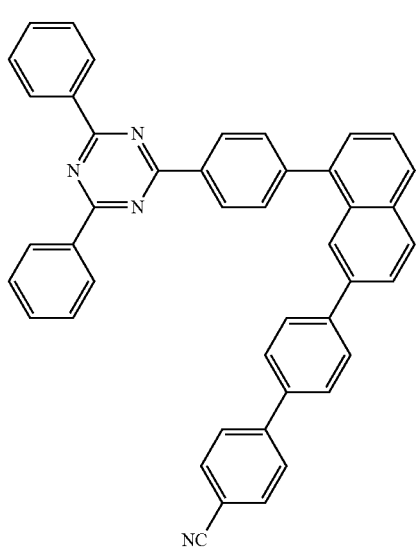

95
-continued
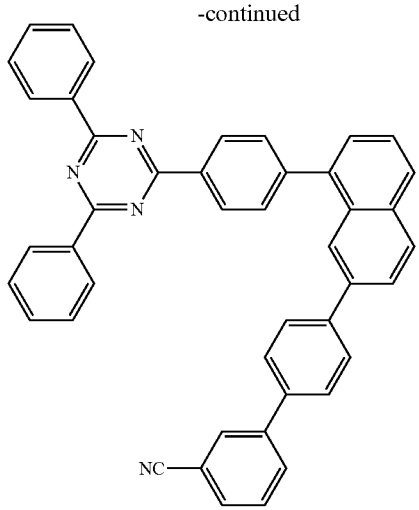
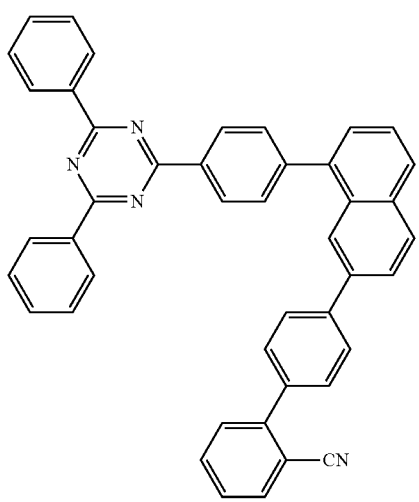
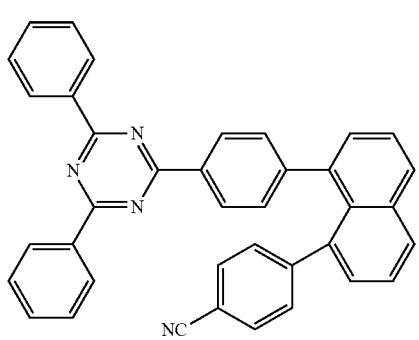
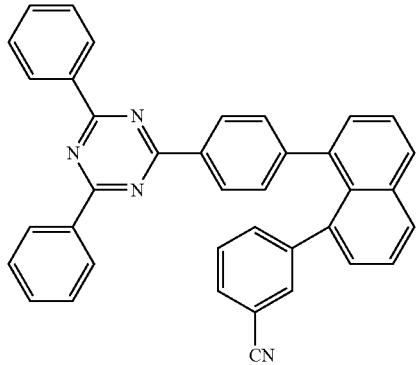
96
-continued
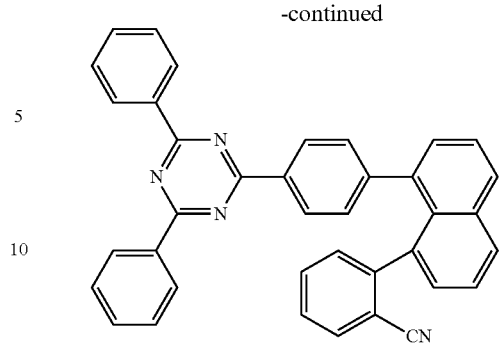
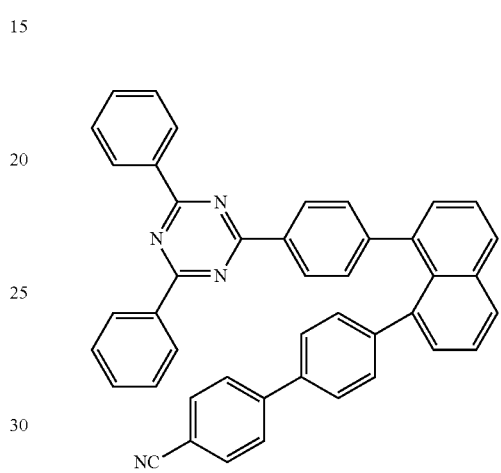
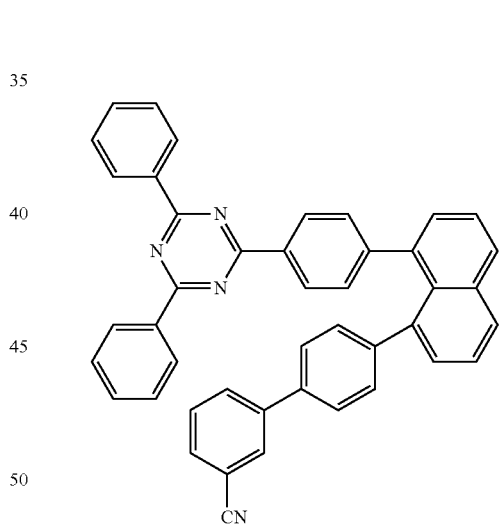
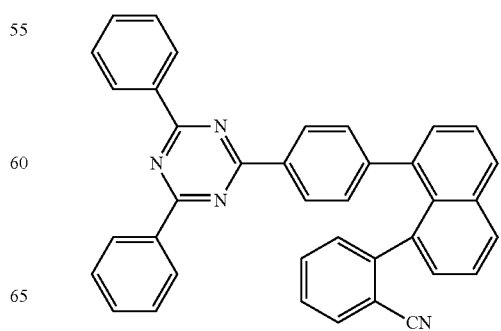

-continued
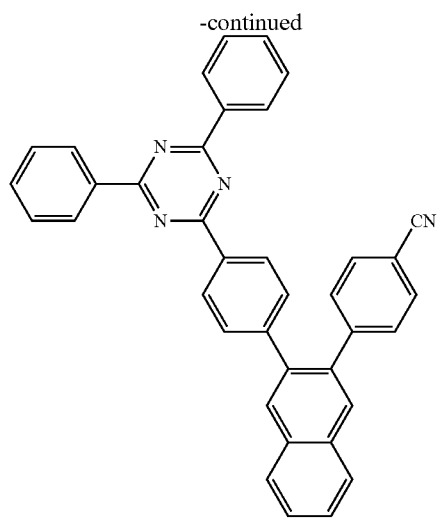
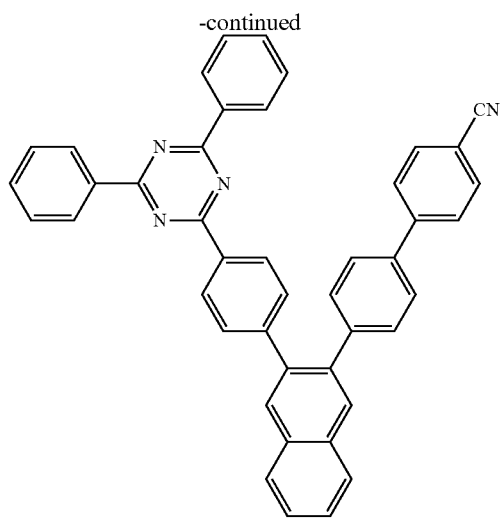
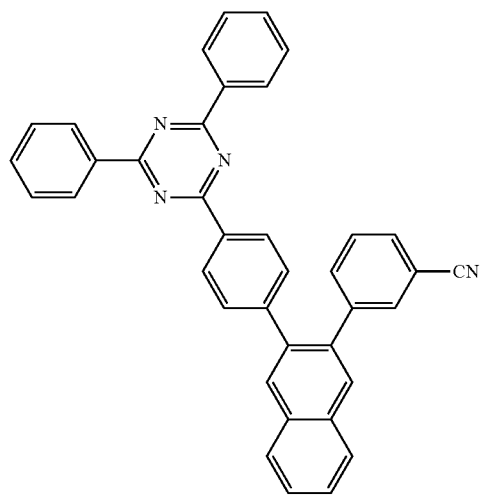
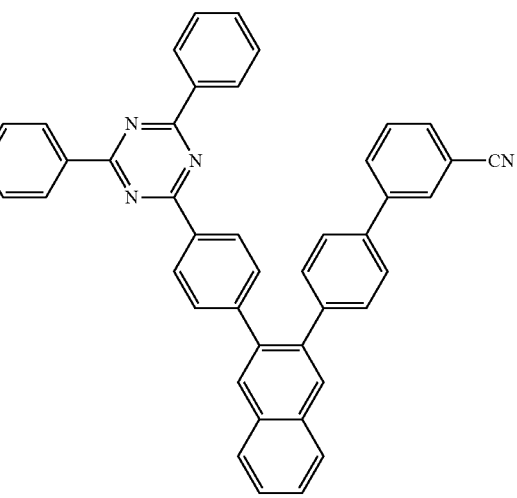
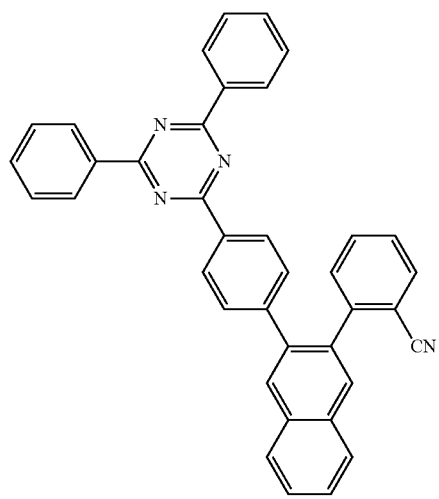
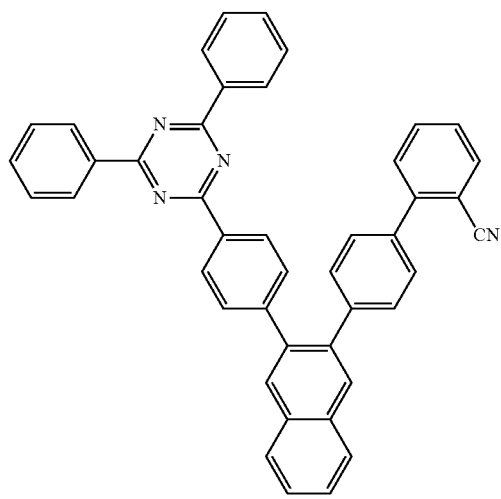

99
-continued
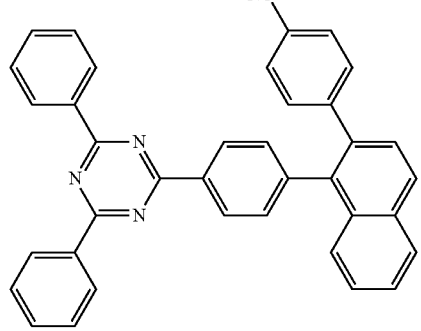
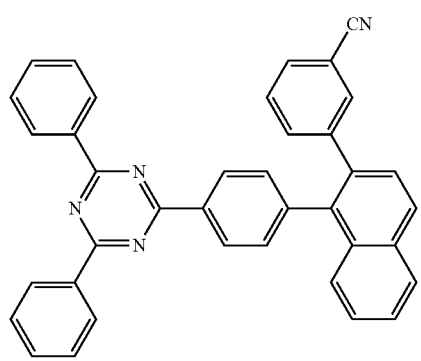
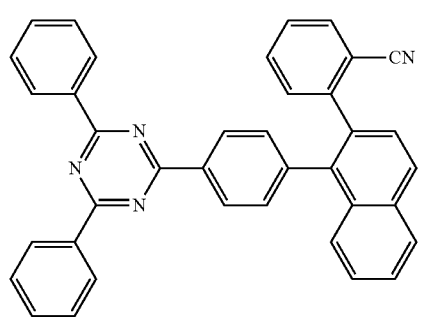
100
-continued
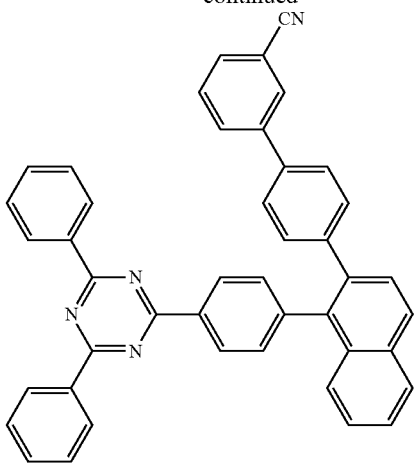
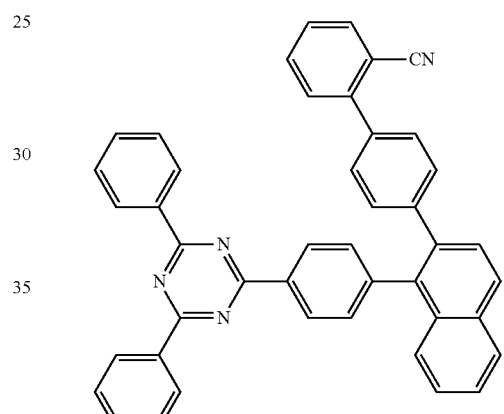
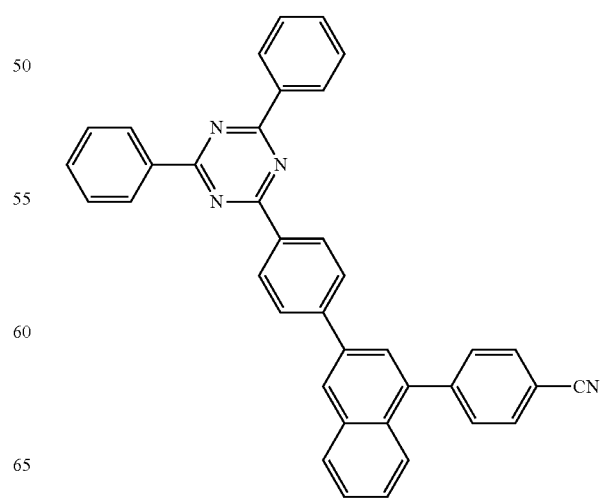
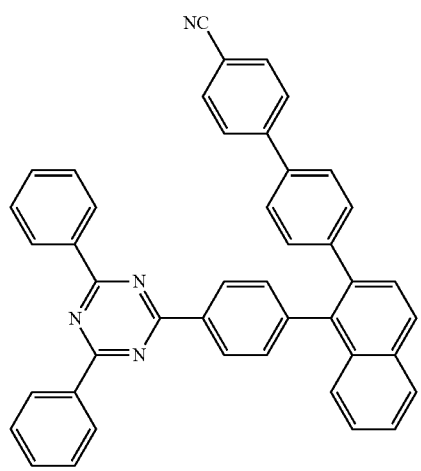

101
-continued
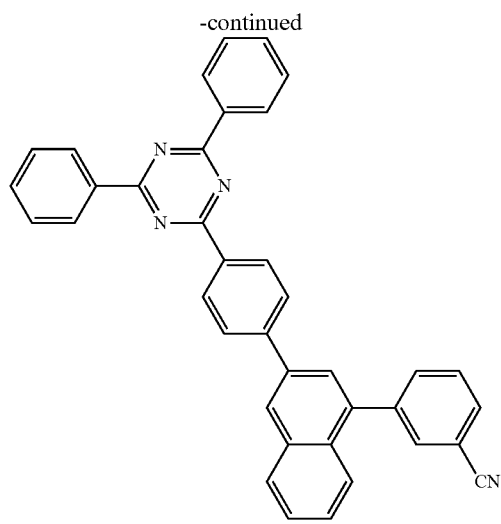
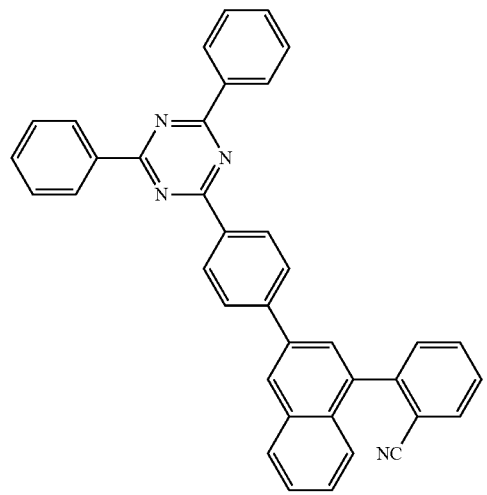
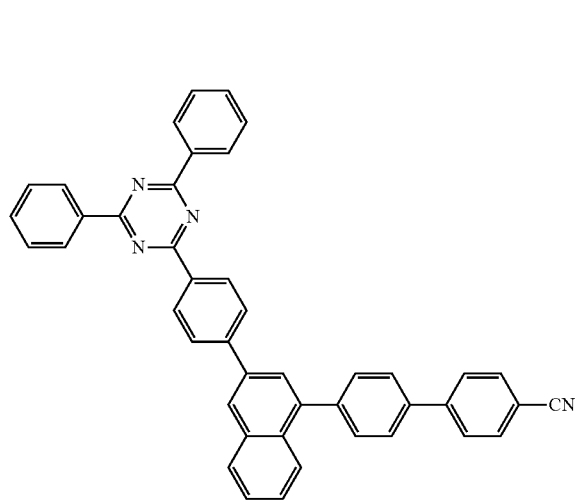
102
-continued
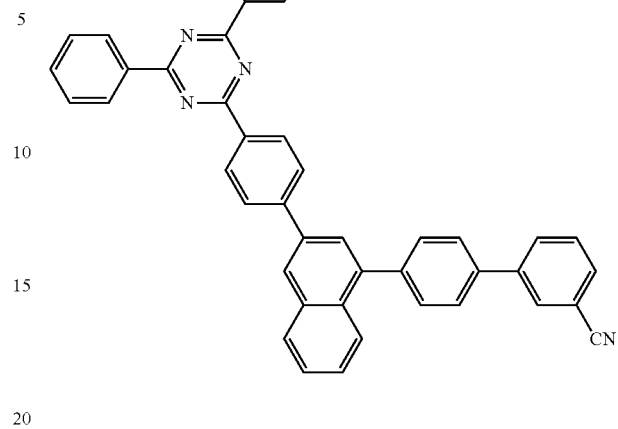
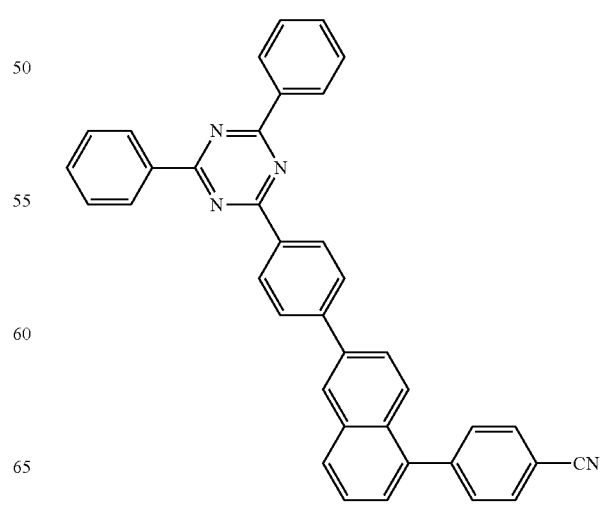

-continued
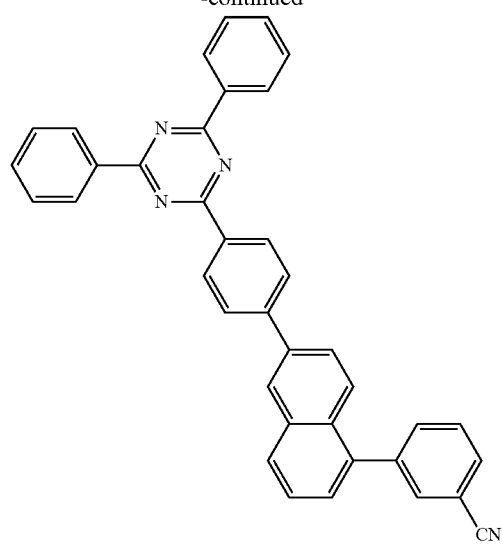
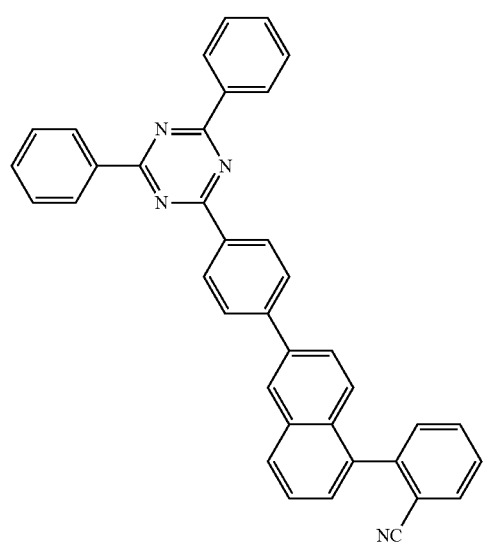
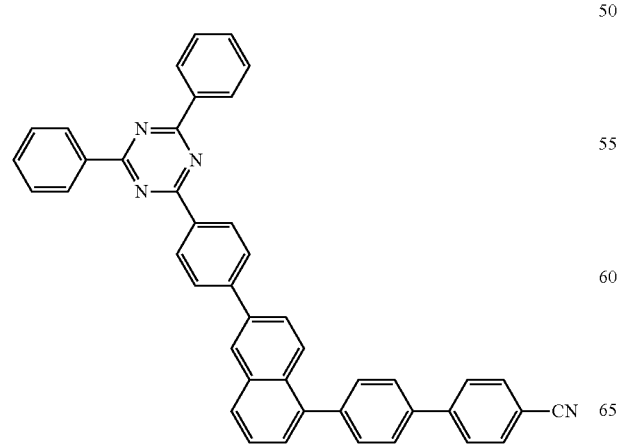
-continued
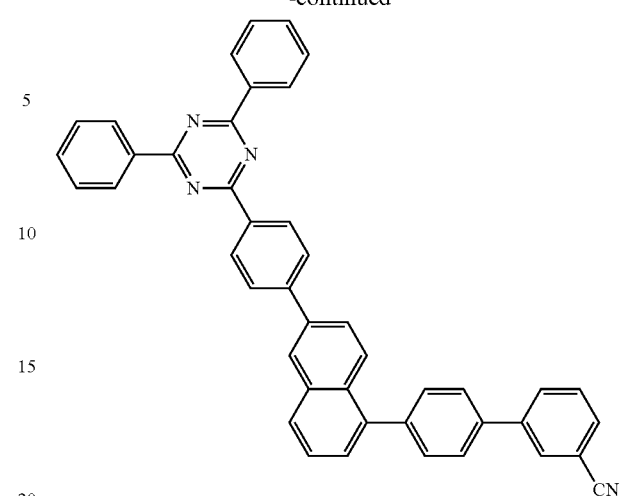
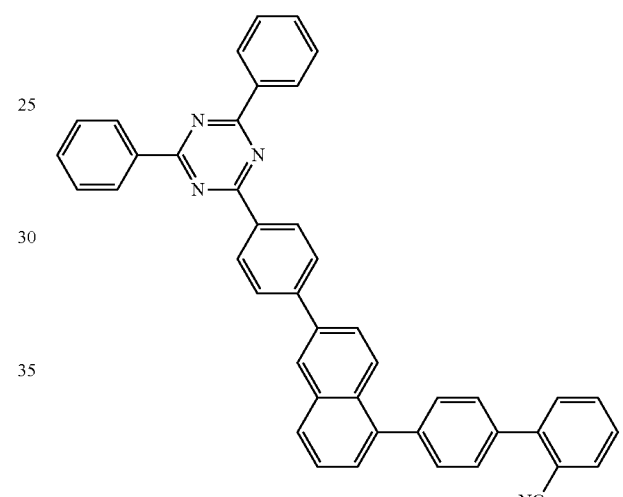

105
-continued
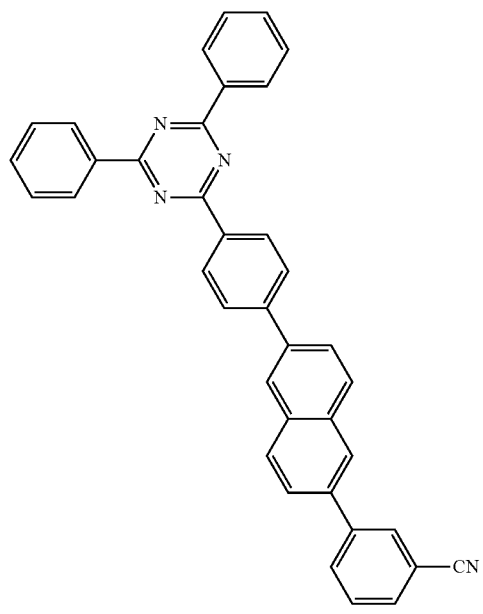
106
-continued
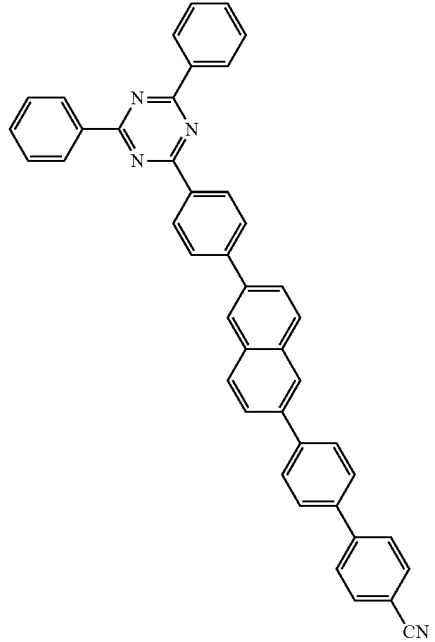
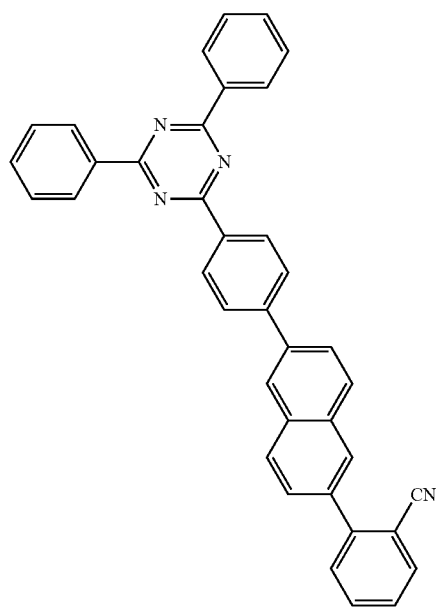
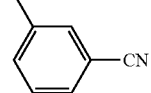

107
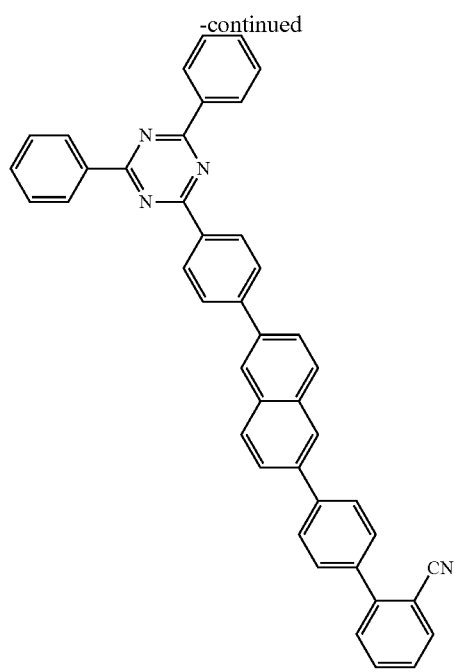
108
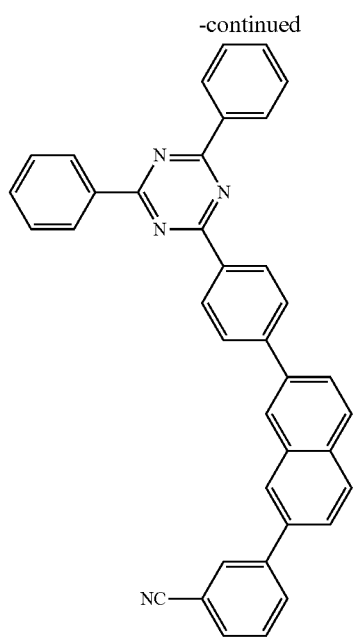
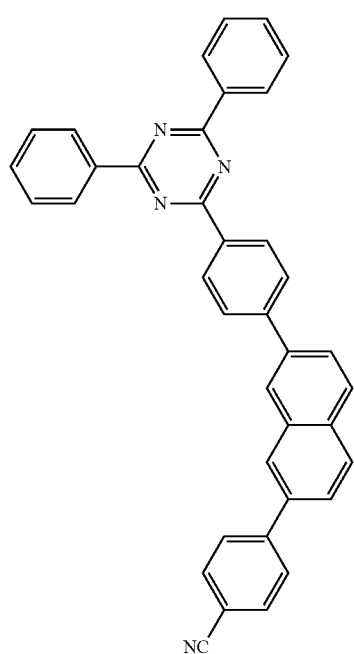
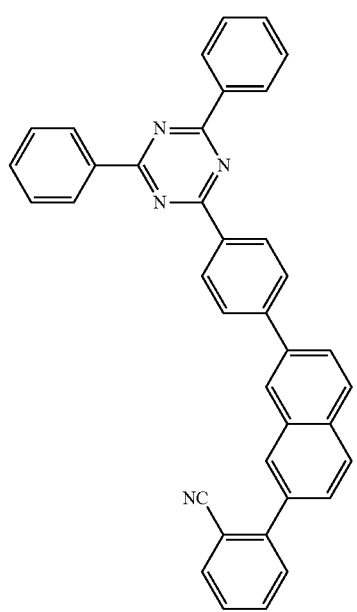 [SMILES: N#Cc1ccccc1-c1ccc2ccc(-c3ccc(-c4nc(-c5ccccc5)nc(-c5ccccc5)n4)cc3)cc2c1]

109
-continued
110
-continued
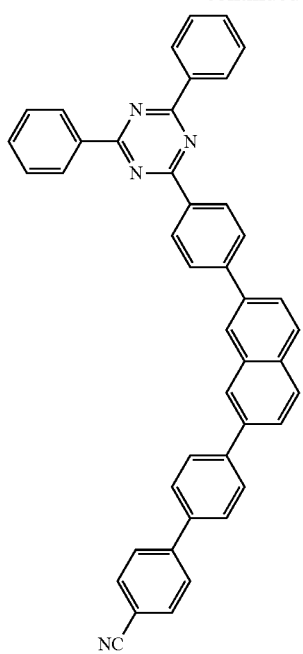
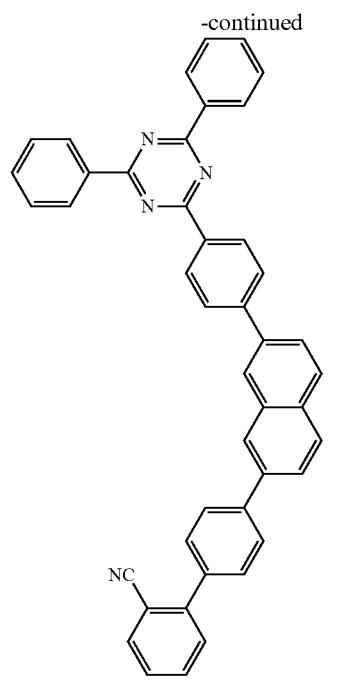
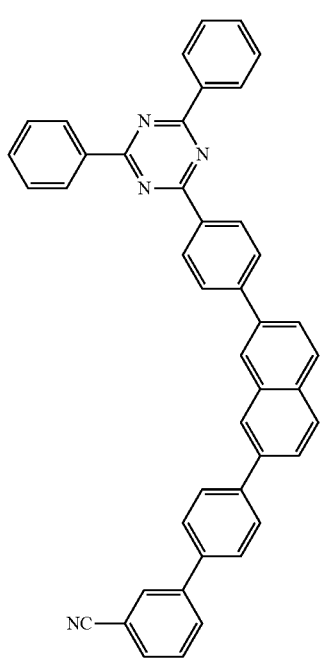
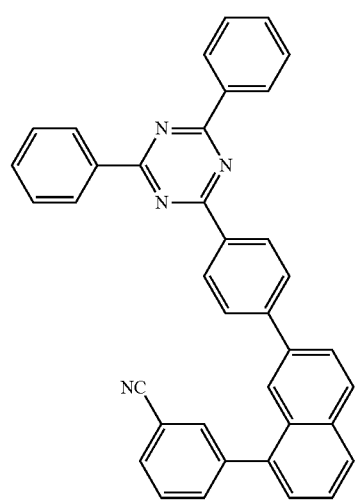

111 | 112
---|---
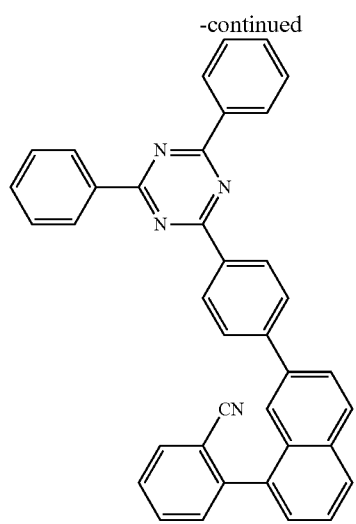 | 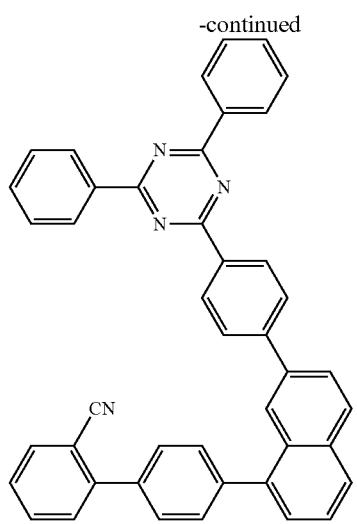
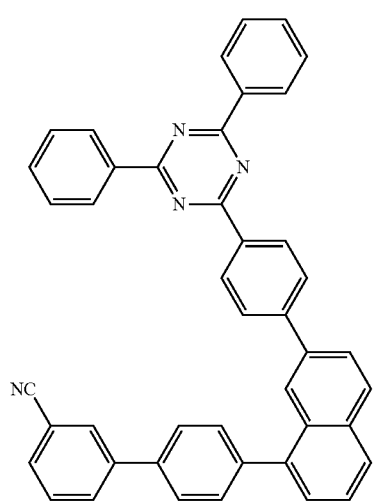 | 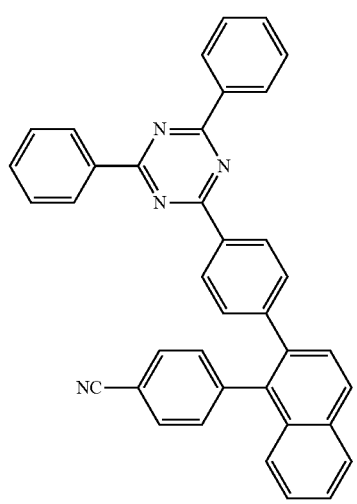

113
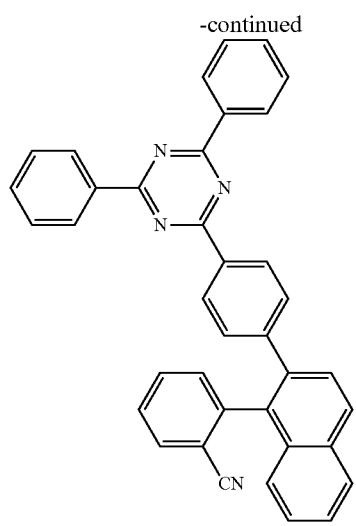
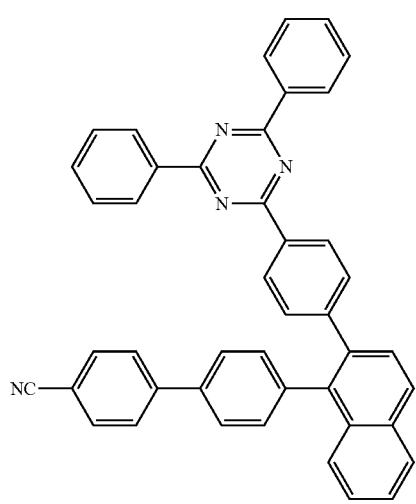
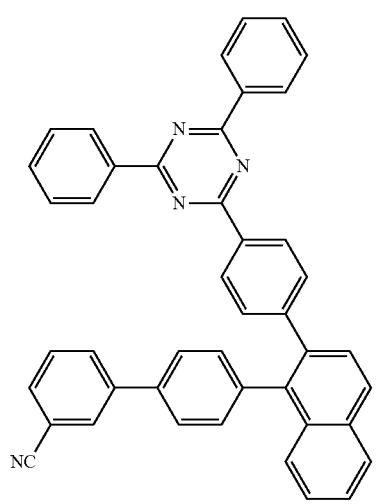
114
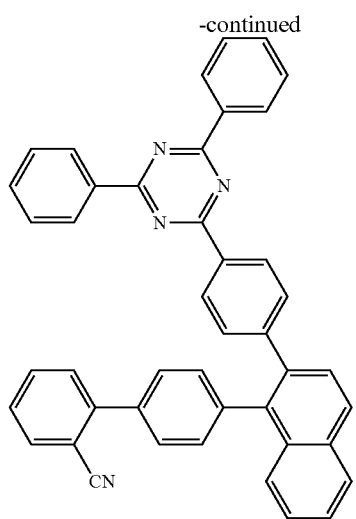
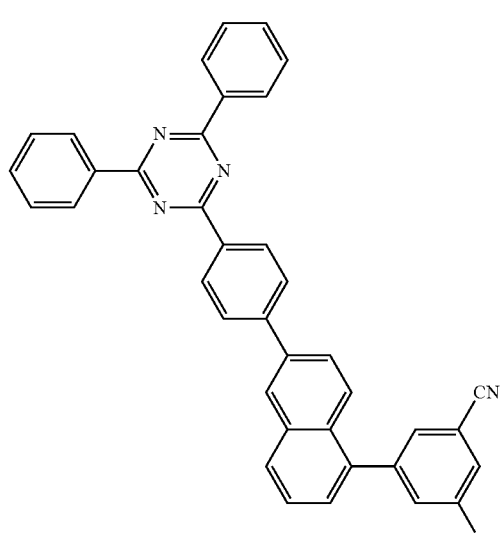

115
-continued
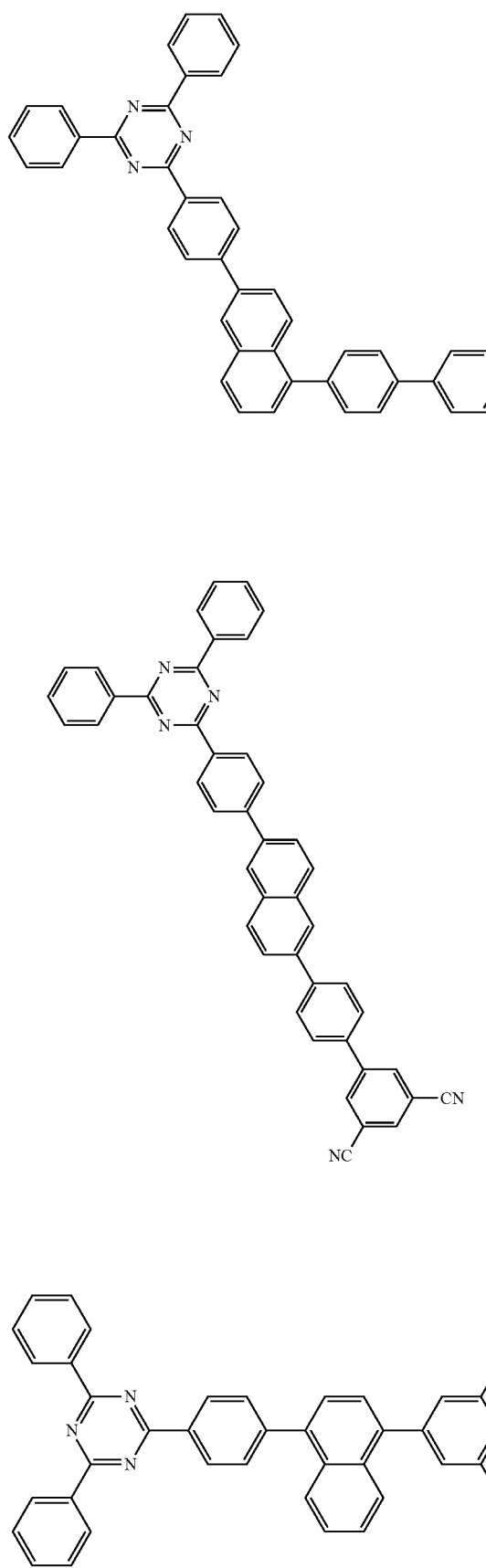
116
-continued
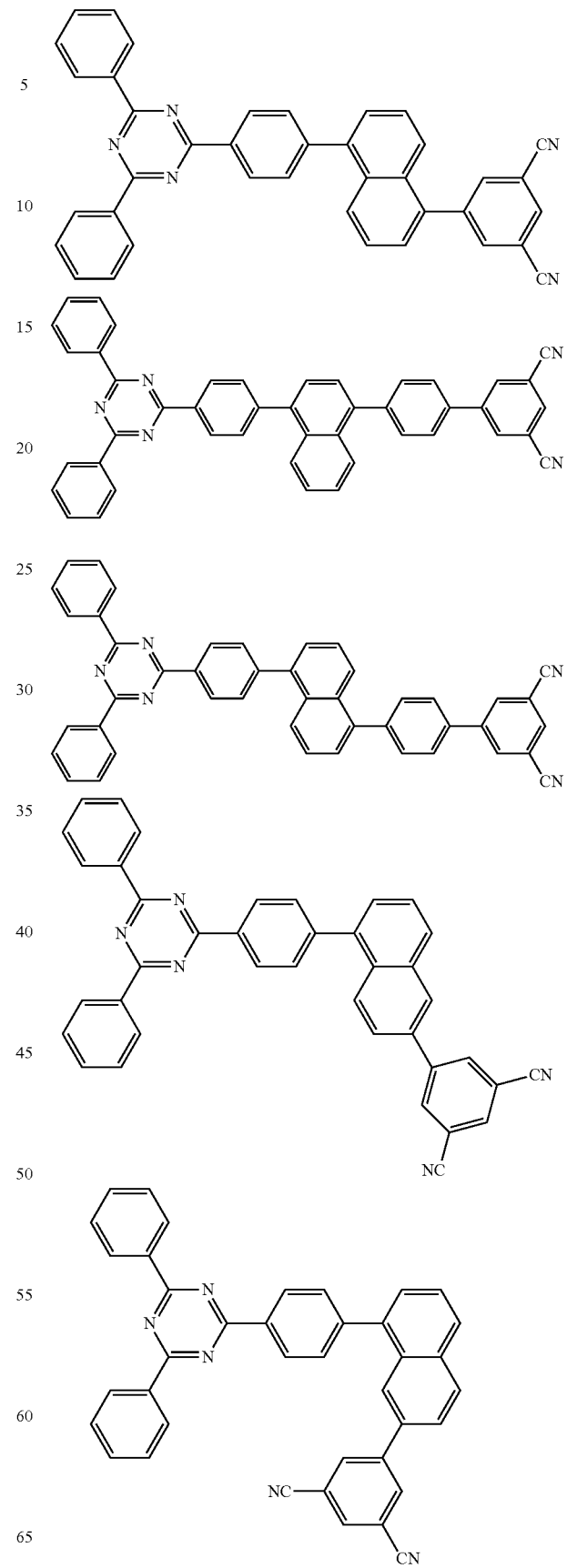

117
-continued
118
-continued
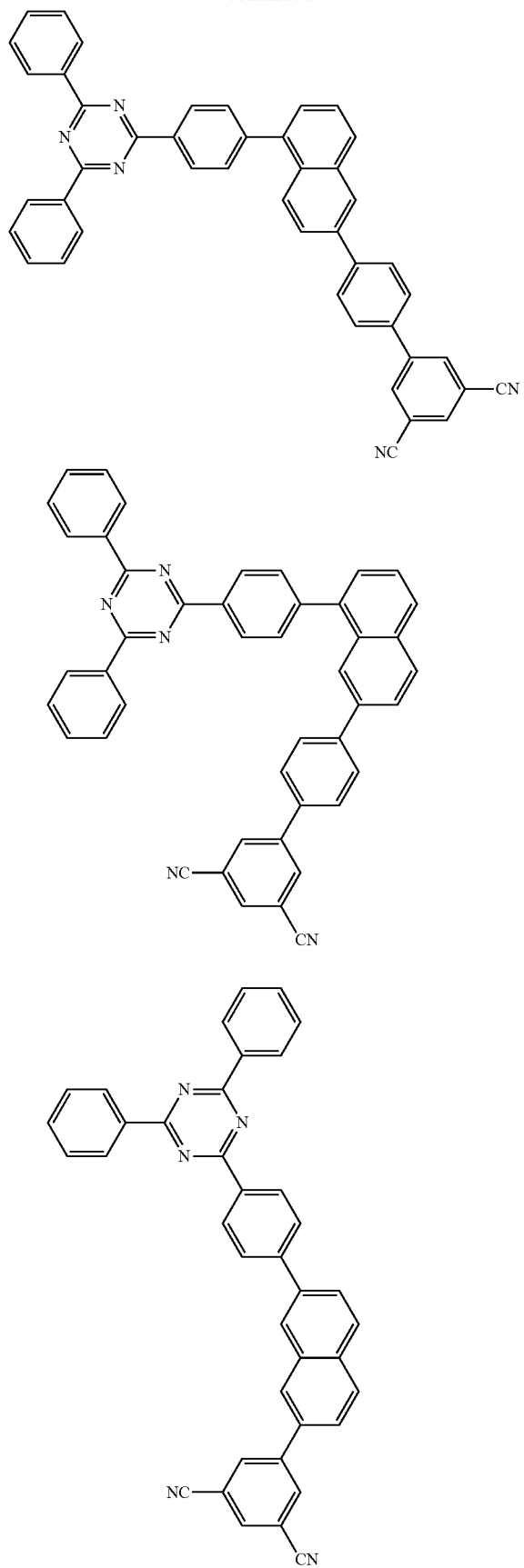
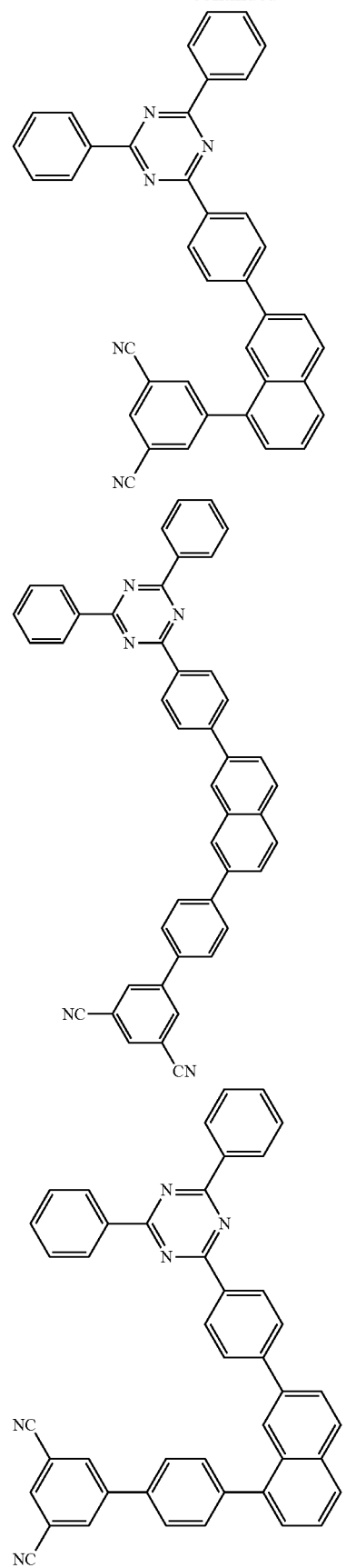 [SMILES: N#Cc1cc(C#N)cc(-c2cccc3ccc(-c4ccc(-c5nc(-c6ccccc6)nc(-c6ccccc6)n5)cc4)cc23)c1 ; N#Cc1cc(C#N)cc(-c2ccc(-c3ccc4ccc(-c5ccc(-c6nc(-c7ccccc7)nc(-c7ccccc7)n6)cc5)cc4c3)cc2)c1 ; N#Cc1cc(C#N)cc(-c2ccc(-c3cccc4ccc(-c5ccc(-c6nc(-c7ccccc7)nc(-c7ccccc7)n6)cc5)cc34)cc2)c1]

119
-continued
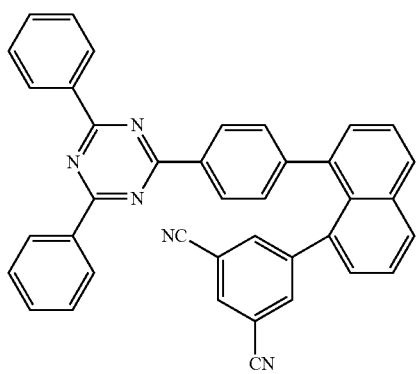
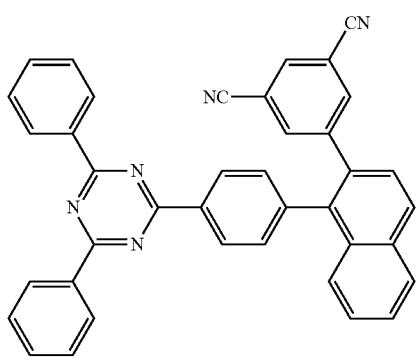
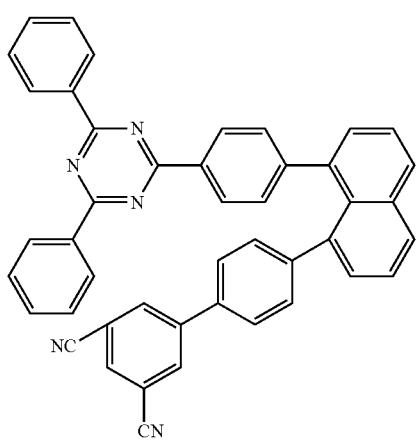
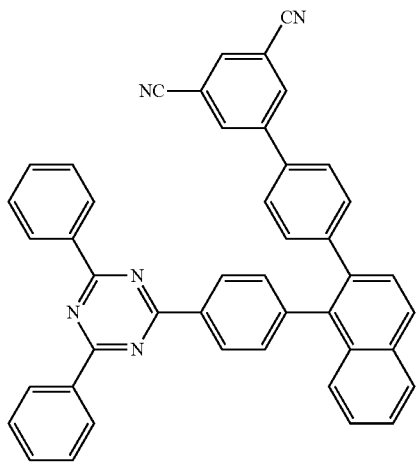
120
-continued
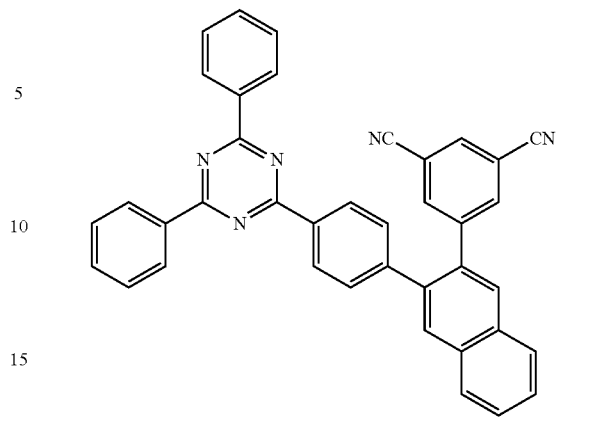
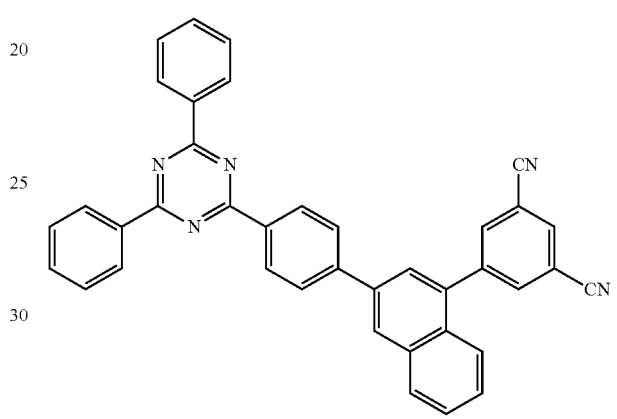
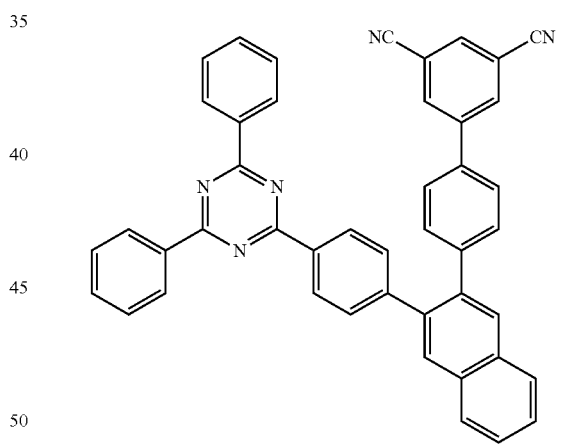
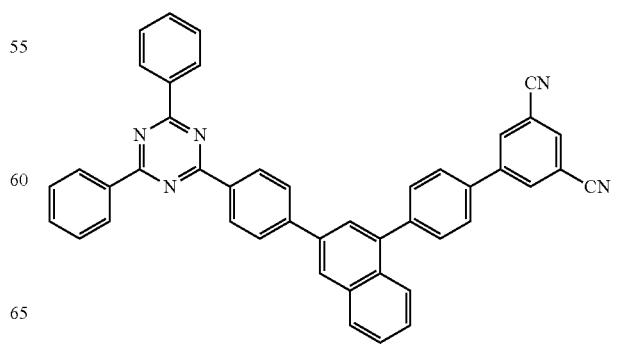

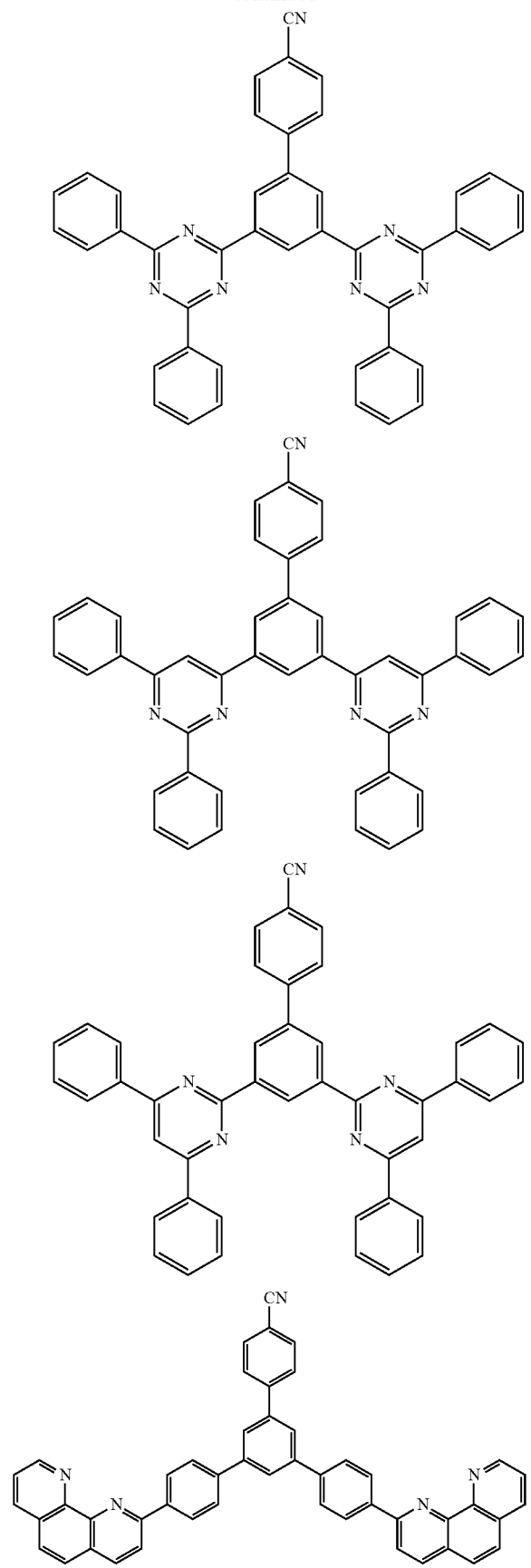
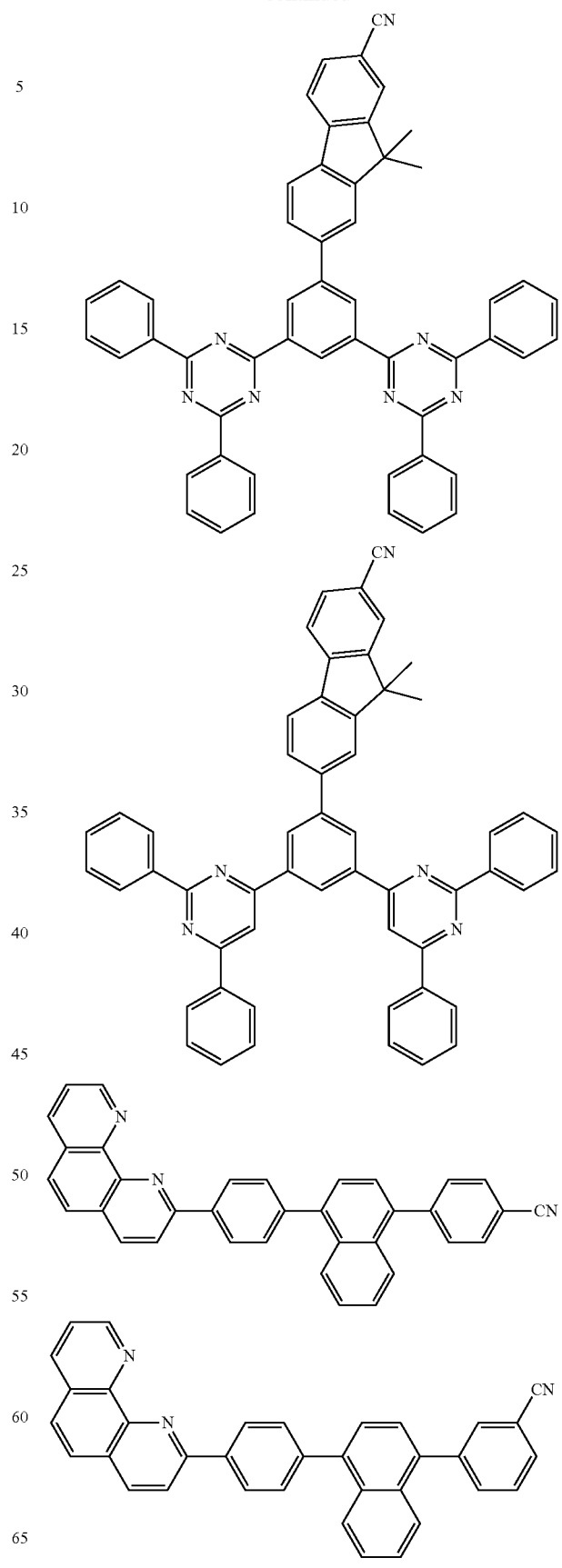

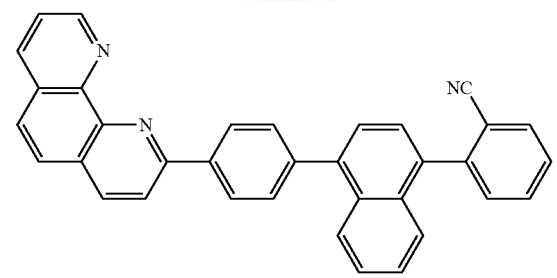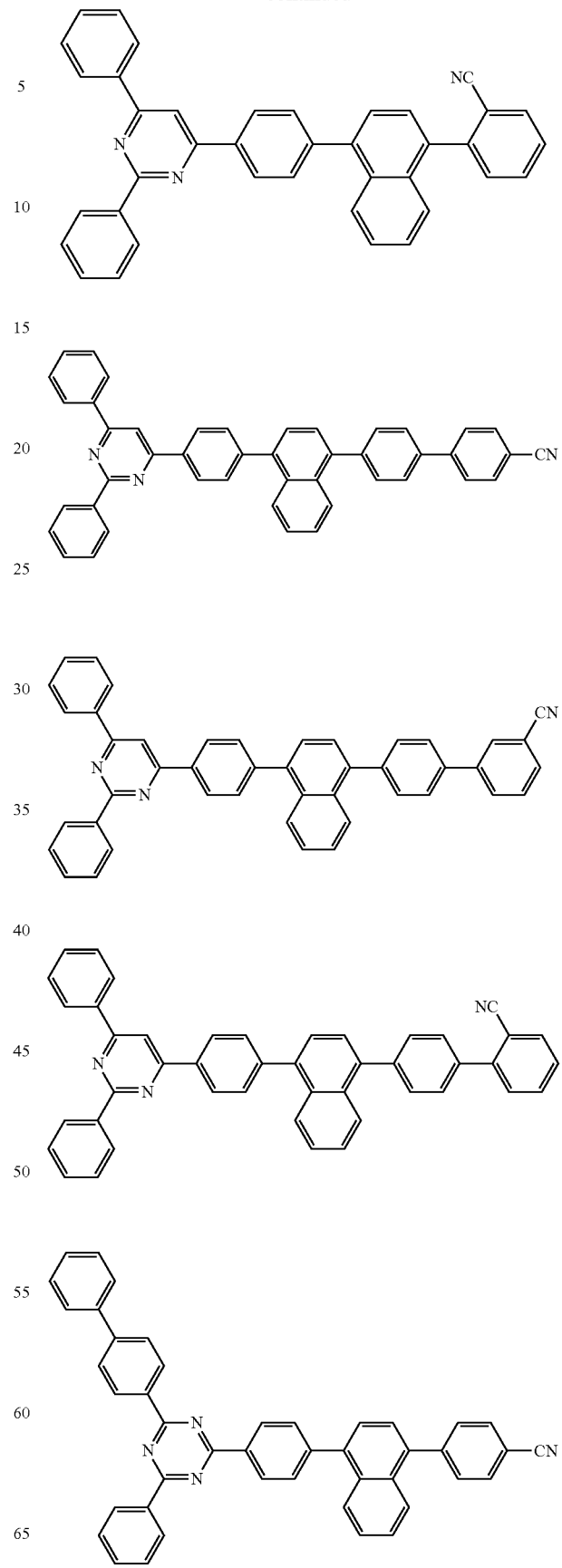

125
-continued
126
-continued
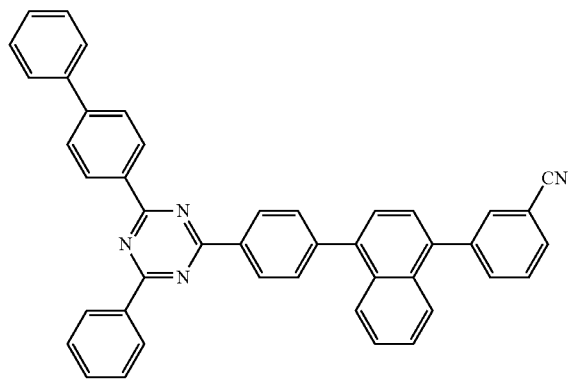
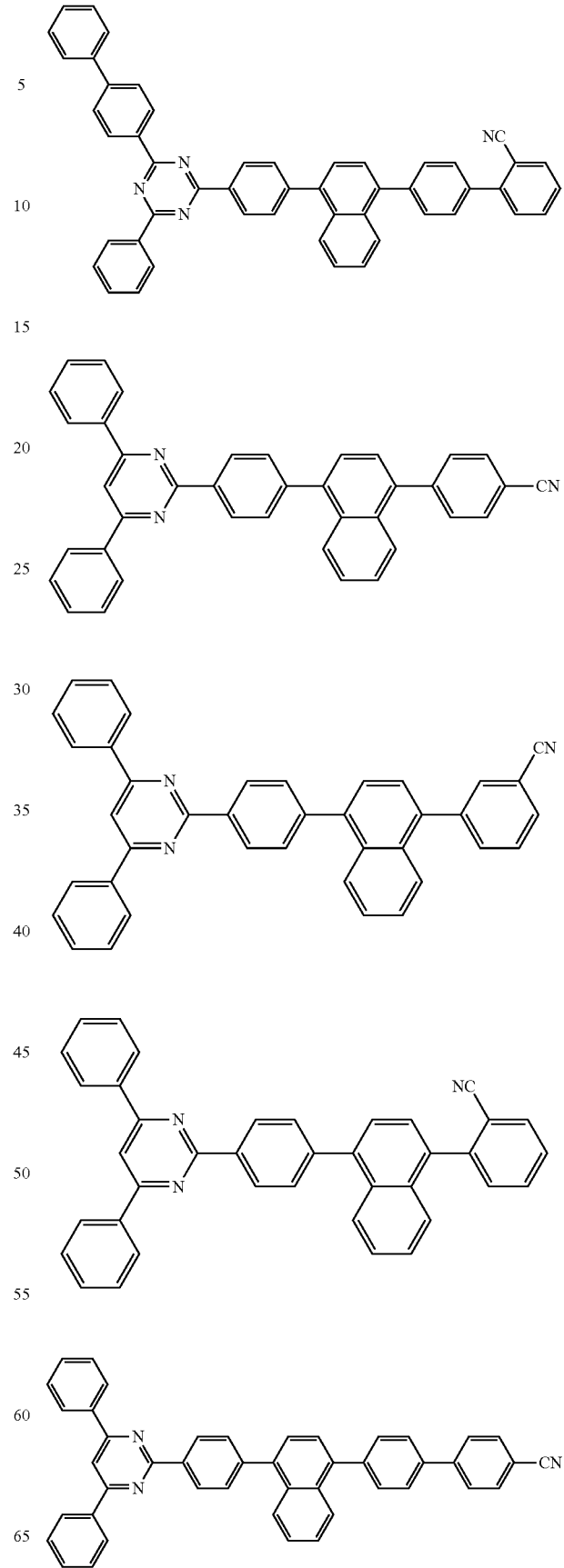

-continued

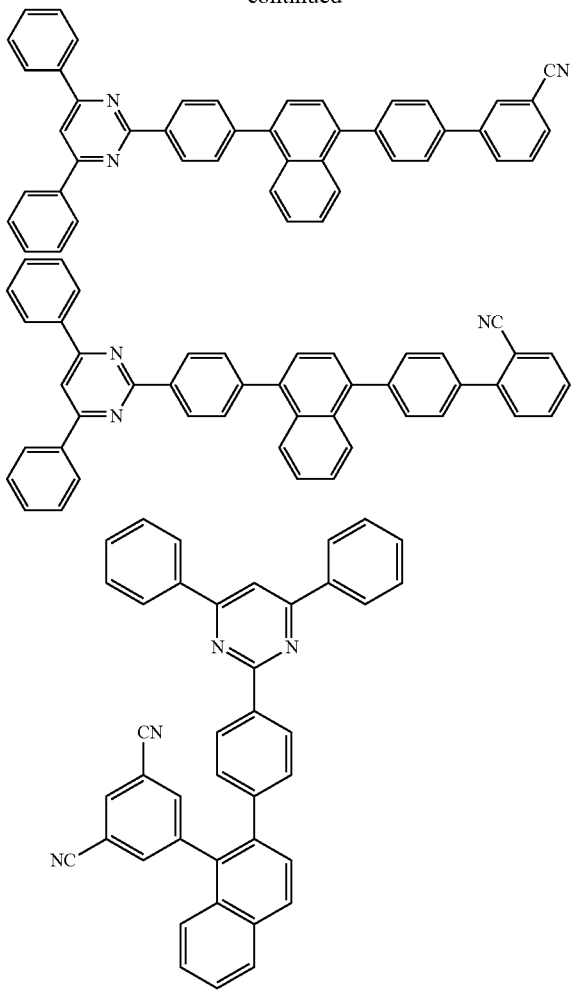

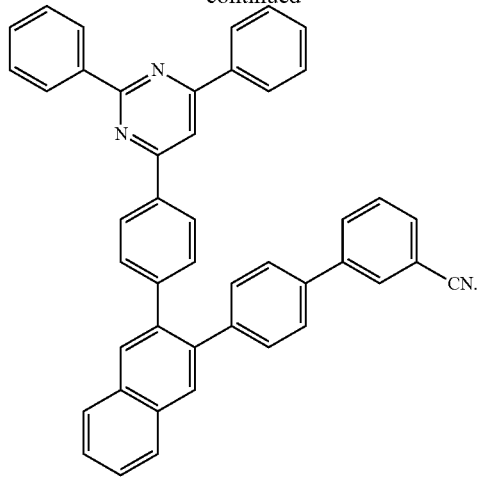

12. The organic light emitting device of claim 1, wherein the organic material layer comprises a light emitting layer, and the light emitting layer comprises the compound.

13. The organic light emitting device of claim 1, wherein the organic material layer comprises a hole blocking layer, and the hole blocking layer comprises the compound.

14. The organic light emitting device of claim 1, wherein the organic material layer comprises an electron transporting layer, an electron injection layer, or a layer which simultaneously transports and injects electrons, and the electron transporting layer, the electron injection layer, or the layer which simultaneously transports and injects electrons comprises the compound.

* * * * *